(12) United States Patent
Fan

(10) Patent No.: US 7,906,633 B2
(45) Date of Patent: Mar. 15, 2011

(54) REAGENTS AND METHODS FOR PREPARING LPS ANTAGONIST B1287 AND STEREOISOMERS THEREOF

(75) Inventor: RuLin Fan, North Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/546,132

(22) PCT Filed: Feb. 18, 2004

(86) PCT No.: PCT/US2004/004921

§ 371 (c)(1),
(2), (4) Date: Dec. 12, 2005

(87) PCT Pub. No.: WO2004/074303

PCT Pub. Date: Sep. 2, 2004

(65) Prior Publication Data

US 2006/0160999 A1    Jul. 20, 2006

Related U.S. Application Data

(60) Provisional application No. 60/448,839, filed on Feb. 20, 2003.

(51) Int. Cl.
*A61K 31/7008* (2006.01)
*A61K 31/7036* (2006.01)
*C07H 15/10* (2006.01)
*C07H 15/12* (2006.01)
*C07H 5/06* (2006.01)

(52) U.S. Cl. .......................... 536/18.7; 514/25; 514/62; 536/4.1; 536/18.4; 536/55.2

(58) Field of Classification Search .................. 514/53; 536/17.2

See application file for complete search history.

(56) References Cited

U.S. PATENT DOCUMENTS 6,184,366 B1 * 2/2001 Christ et al. ................ 536/17.2
6,809,195 B1 * 10/2004 Sanghvi et al. ............. 536/25.3

FOREIGN PATENT DOCUMENTS

WO    WO 96/39411    12/1996

OTHER PUBLICATIONS

Protective groups in Organic synthesis, by Greene and Wuts, published 1999 by John Wiley and Sons, pp. 183-185.*

* cited by examiner

*Primary Examiner* — Eric S Olson
(74) *Attorney, Agent, or Firm* — McCarter & English, LLP

(57) ABSTRACT

The present invention provides methods for preparing LPS antagonist lipodisaccharide B1287 and stereoisomers thereof, which compounds are useful as in the prophylactic and affirmative treatment of endotoxemia including sepsis, septicemia and various forms of septic shock. Also provided are synthetic intermediates useful for implementing the inventive methods.

14 Claims, No Drawings

REAGENTS AND METHODS FOR PREPARING LPS ANTAGONIST B1287 AND STEREOISOMERS THEREOF

PRIORITY CLAIM

The present application claims the benefit under 35 U.S.C. §371 of International Application No.: PCT/US2004/004921 (published PCT application No. WO 2004/074303), filed Feb. 18, 2004, which claims priority to U.S. Provisional Application No. 60/448,839, filed Feb. 20, 2003. Each of the above cited applications is incorporated herein by reference in its entirety.

BACKGROUND OF THE INVENTION

The incidence of gram negative bacteria in the United States has been estimated to be approximately 100,000 to 300,000 cases per year, with a mortality rate of 30-60%. Antibiotics are commonly used as the primary chemotherapy for this disease; however, their bactericidal action can result in disruption of the bacterium and concomitant release of endotoxin, i.e., the lipopolysaccharide (LPS) moiety of the bacterial outer membrane. The liberated LPS induces a number of pathophysiological events in mammals (collectively referred to as gram-negative endotoxemia or sepsis syndrome). These include fever, generalized inflammation, disseminated intravascular coagulation (DIC), hypotension, acute renal failure, acute respiratory distress syndrome (ARDS), hepatocellular destruction and cardiac failure.

It has previously been established that, for infections caused by gram-negative bacteria, sepsis is related to the toxic components of the bacteria. Specifically, among the well-described bacterial toxins are the endotoxins or lipopolysaccharides (LPS), a cell-wall structure of the gram-negative bacteria. These molecules are glycolipids that are ubiquitous in the outer membrane of all gram-negative bacteria. While the chemical structure of most of the LPS molecule is complex and diverse, a common feature is the lipid A region of LPS (Rietschel, et al., in the Handbook of Endotoxins, 1: 187-214 eds. R. A. Proctor and E. Th. Rietschel, Elsevier, Amsterdam (1984)); recognition of lipid A in biologic systems initiates many, if not all, of the pathophysiologic changes of sepsis. Because lipid A structure is highly conserved among all types of gram-negative organisms, common pathophysiologic changes characterize gram-negative sepsis. It is also generally thought that the distinct cell wall substances of gram-positive bacteria and fungi trigger a similar cascade of events, although the structures involved are not as well studied as gram-negative endotoxin.

Although endotoxin initiates septic shock, it has little or no direct toxic effect on tissues; instead, it triggers an immunobiological response leading to a cascade of release of cytokines such as tumor-necrosis factor (TNF), interleukin-1, interleukin-6 and interleukin-8, and other biological mediators such as nitric oxide, as well as an array of secondary mediators (e.g., prostaglandins, leukotrienes, interferons, platelet-activating factor, endorphins and colony-stimulating factors).

Therapies for endotoxin-related diseases have generally been directed towards controlling the inflammatory response. Such therapies include corticosteriod treatment, suggested to ameliorate endotoxin-mediated cell membrane injury and to reduce production of certain biological mediators; administration of antibodies designed to neutralize bacterial LPS; treatment with agents to suppress hypotension or with naloxone which apparently blocks the hypotensive effects associated with sepsis syndrome; and treatment with nonsteroidal anti-inflammatory drugs, purported to block cyclooxygenases and thereby decrease the production of certain secondary mediators such as prostaglandins and thromboxane.

However, none of these therapies to date has resulted in significant reduction in the morbidity and mortality resulting from sepsis and septic shock syndrome. Thus there is a long felt need for agents to affirmatively treat this disorder.

Certain lipodisaccharides are disclosed in Macher et al., Great Britain patent 2,179,945, Meyers et al., Great Britain patent 2,220,211, Shiba et al., European patent 172,581, Anderson et al., U.S. Pat. No. 4,495,346 and Shiba et al., U.S. Pat. No. 5,066,794.

Christ, et al., "Anti-Endotoxin Compounds," U.S. Pat. No. 5,530,113, filed Aug. 25, 1992, the contents of which are included by reference, also disclose certain disaccharide compounds, such as B531 shown below, useful for the treatment of endotoxemia.

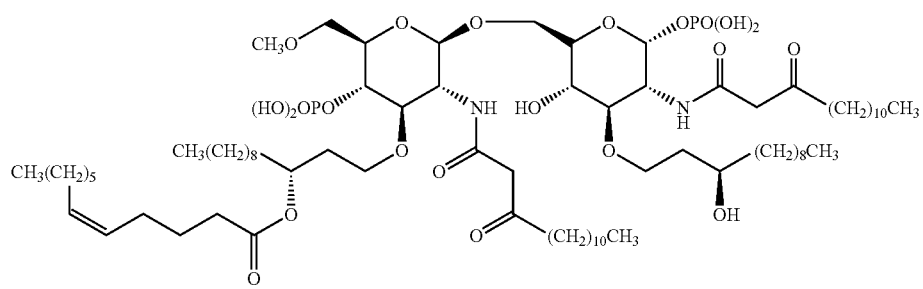

Lipodisaccharides with enhanced pharmacological selectivity, efficacy and increased persistence in action were disclosed in U.S. Pat. No. 5,935,938, the entire contents of which are incorporated herein by reference. Specifically, lipodisaccharide B1287 was identified as having a better pharmacological profile than some of its congeners, and thus shows great promise for the treatment of LPS-mediated disorders.

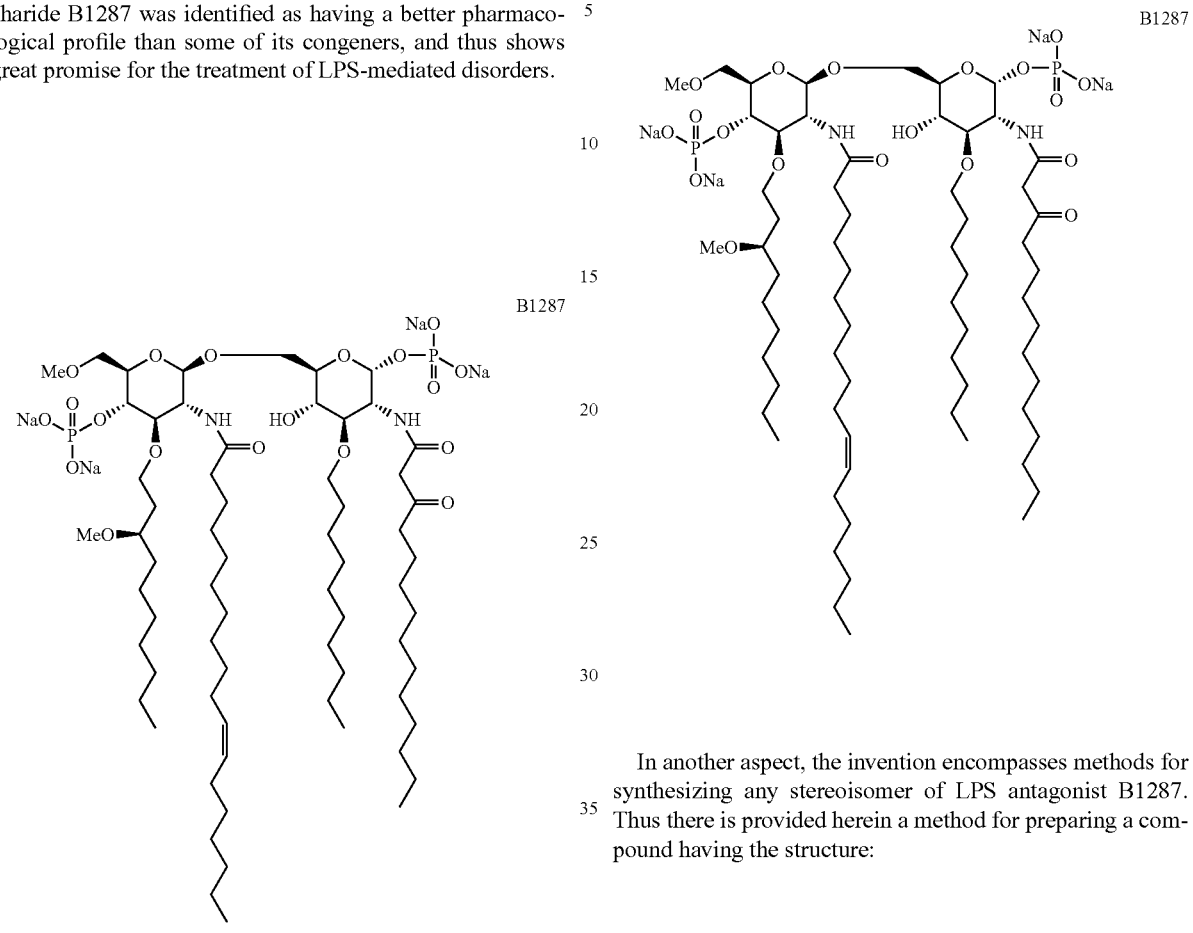

However, existing methods for its preparation typically involve >36 synthetic steps, and are thus not well suited for industrial applicability. Specifically, the synthetic approaches for preparing B1287 that are disclosed in U.S. Pat. No. 5,935,938 are lengthy, hazardous (e.g., involve azide chemistry) and thus inadequate for large-scale syntheses.

Clearly, there remains a need to develop efficient and high yielding synthetic methodologies to access a variety of analogues of Lipid A, particularly B1287 and stereoisomers thereof, which compounds are useful as in the prophylactic and affirmative treatment of endotoxin exposure including sepsis, septicemia, endotoxemia, various forms of septic shock and related disorders using novel liposaccharide analogs.

SUMMARY OF THE INVENTION

In one aspect, the present invention provides a method for synthesizing LPS agonist B1287 having the structure:

In another aspect, the invention encompasses methods for synthesizing any stereoisomer of LPS antagonist B1287. Thus there is provided herein a method for preparing a compound having the structure:

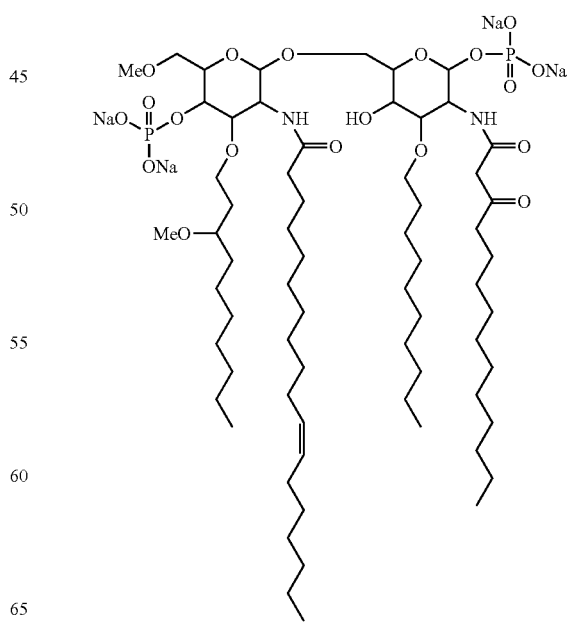

In certain embodiments, the inventive method comprises steps of:

(d) effecting glycosylation of a monosaccharide having the structure:

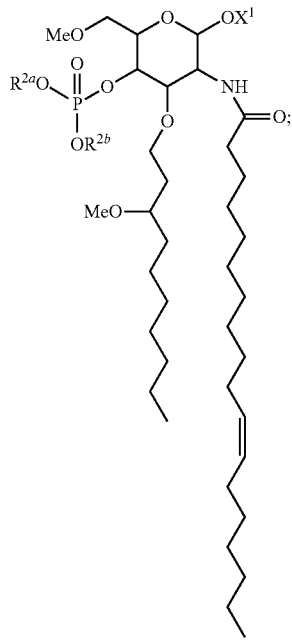

wherein $OX^1$ represents a suitable leaving group for effecting the glycosylation; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

with a monosaccharide having the structure:

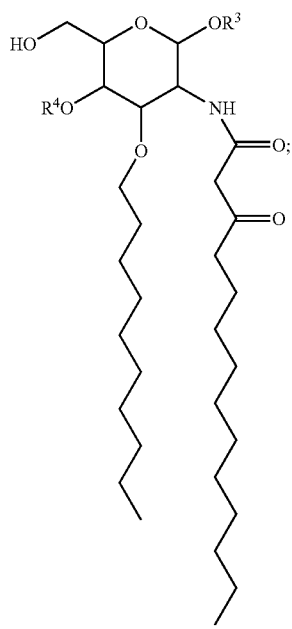

wherein $R^3$ and $R^4$ are each independently a suitable oxygen protecting group;

under suitable conditions to effect formation of a disaccharide having the structure:

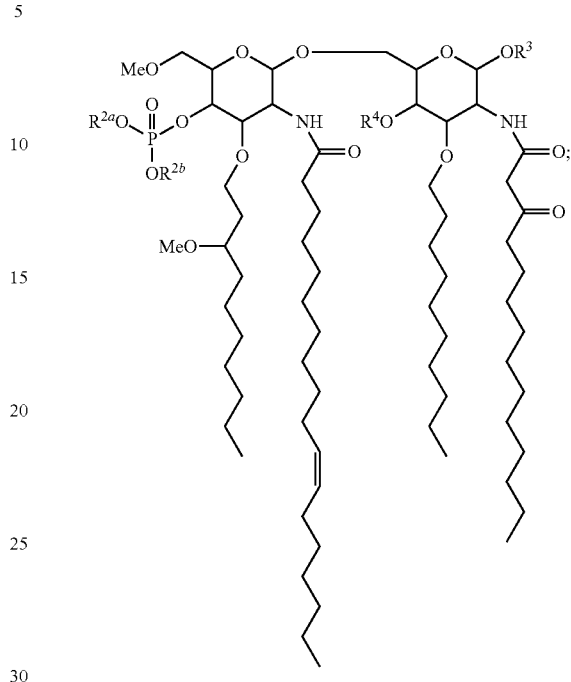

(e) deprotecting the disaccharide formed in step (a) under suitable conditions to effect formation of a partially deprotected disaccharide having the structure:

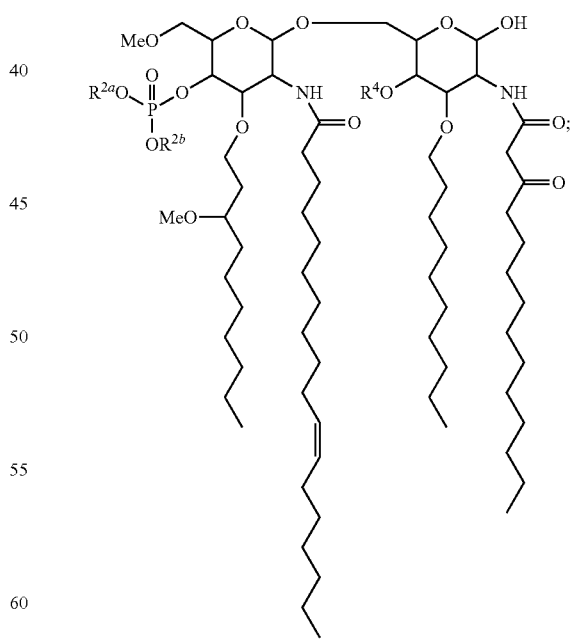

(f) reacting the partially deprotected disaccharide formed in step (b) with a suitable reagent under suitable conditions to effect formation of a diphosphorylated disaccharide having the structure:

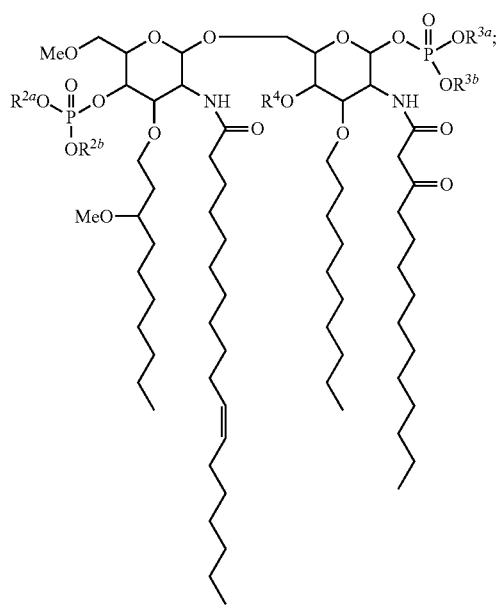

wherein $R^{3a}$ and $R^{3b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (g) treating the diphosphorylated disaccharide formed in step (c) with one or more suitable reagents under suitable conditions to effect formation of a disaccharide having the structure:

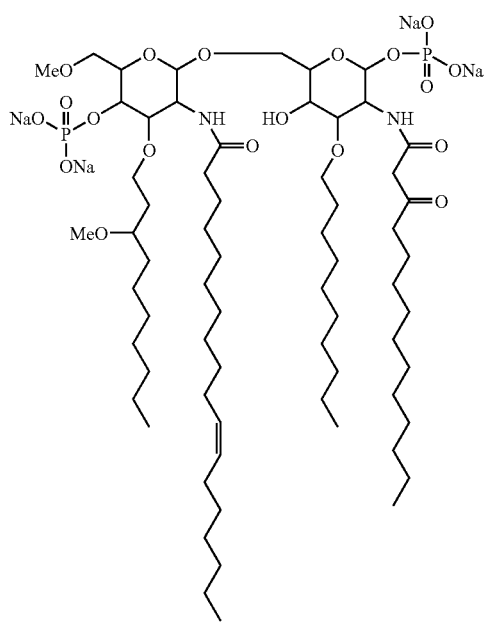

In yet other embodiments, the step of treating the diphosphorylated disaccharide formed in step (c) with one or more suitable reagents under suitable conditions leads to the formation of a compound having the structure:

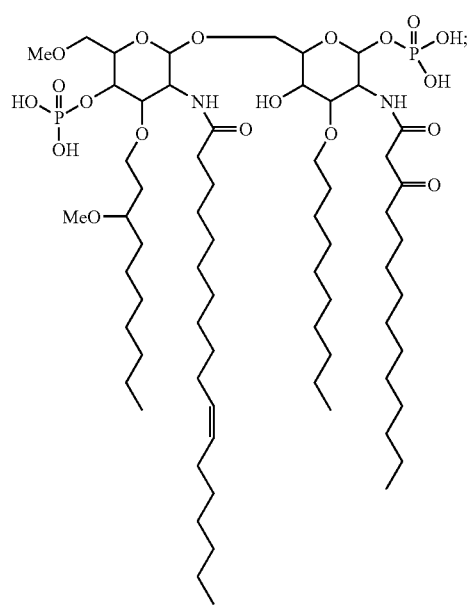

which is then purified to yield the corresponding tetrasodium salt:

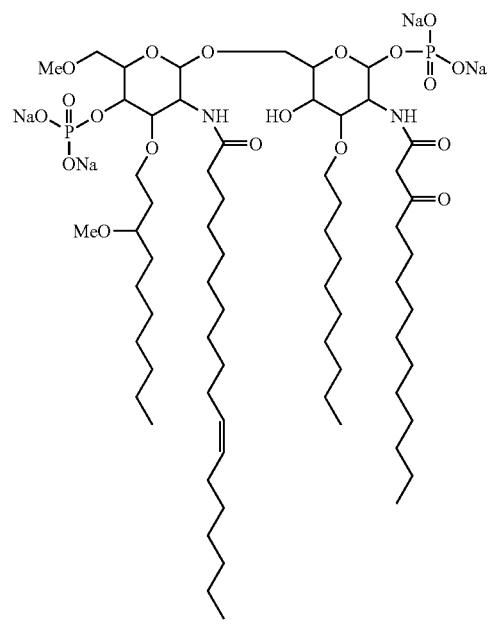

In still other embodiments, the purification process comprises chromatographic separation and treatment with a base. In certain exemplary embodiments, the purification process comprises (i) ion exchange chromatography, (ii) POROS 50 R2, methanol, and (iii) treatment with aqueous NaOH.

In certain exemplary embodiments, the sacharide having the structure:

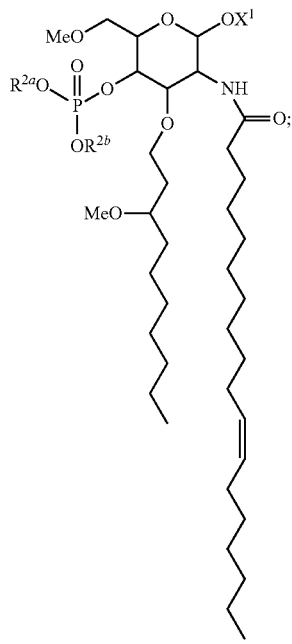

wherein $OX^1$ represents a suitable leaving group for effecting a glycosylation reaction; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

is prepared by a process comprising steps of:

(a) reacting an amine having the structure:

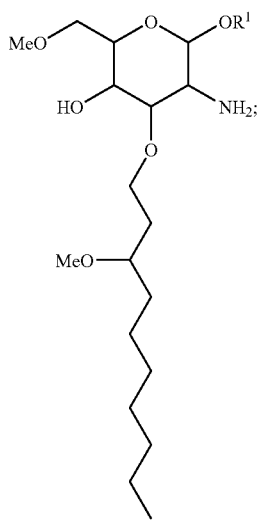

wherein $R^1$ is a suitable oxygen protecting group;

with a suitable vaccenoyl acid derivative to effect formation of an amide intermediate having the structure:

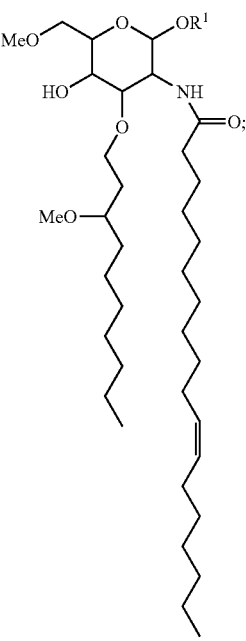

(b) reacting the amide intermediate formed in step (a) with a suitable reagent to effect formation of a phosphorylated saccharide having the structure:

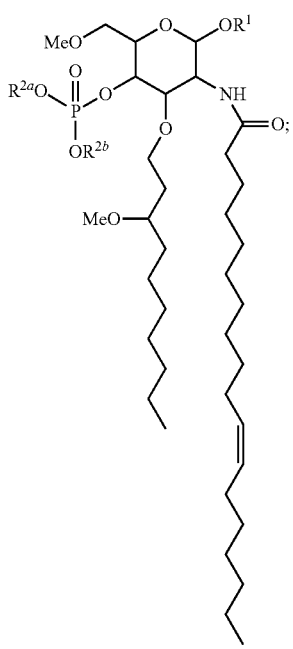

wherein $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (c) deprotecting the phosphorylated saccharide formed in step (b) under suitable conditions to effect formation of an alcohol intermediate having the structure:

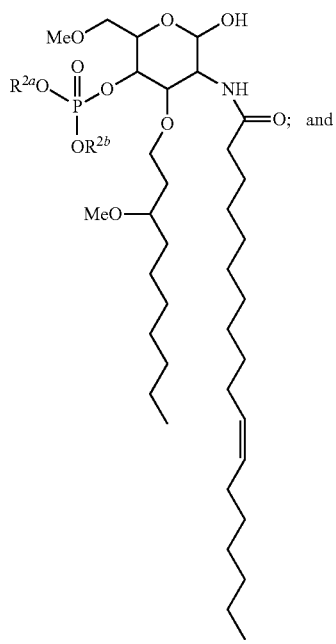

(d) reacting the alcohol intermediate formed in step (c) under suitable conditions to effect formation of a saccharide having the structure:

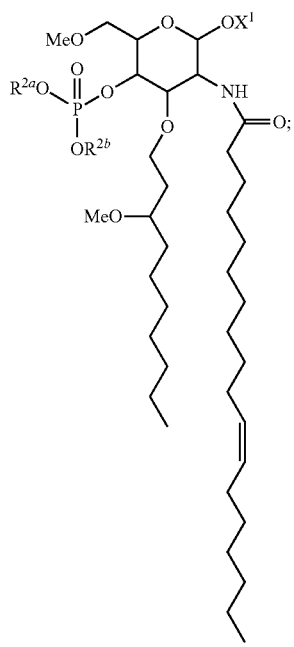

wherein $OX^1$ represents a suitable leaving group for effecting a glycosylation reaction.

In yet other embodiments, the saccharide having the structure:

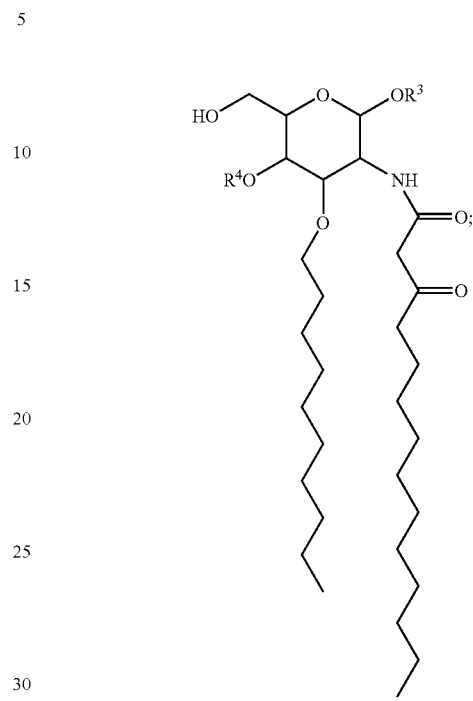

wherein $R^3$ and $R^4$ are each independently a suitable oxygen protecting group;

is prepared by a process comprising steps of:

(a) reacting a saccharide having the structure:

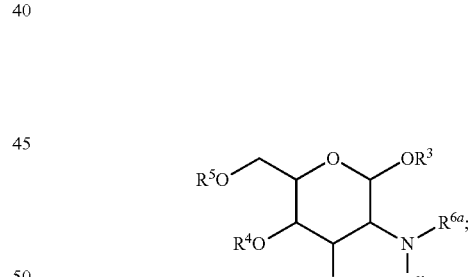

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and $R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;

with a suitable decanyl derivative to effect formation of a decanyl ether having the structure:

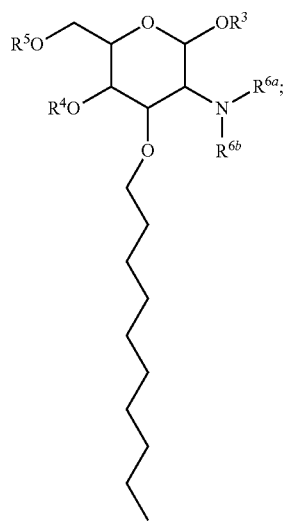

(b) deprotecting the decanyl ether formed in step (a) under suitable conditions to effect formation of a partially deprotected intermediate having the structure:

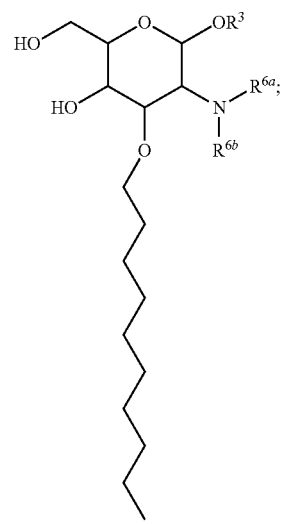

(c) deprotecting the amide moiety of the intermediate formed in step (b) under suitable conditions to give an amine intermediate having the structure:

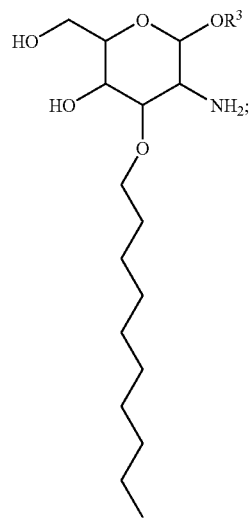

(d) reacting the amine intermediate formed in step (c) with a suitable 3-Oxo-tetradecanoic acid derivative under suitable conditions to effect formation of an amide intermediate having the structure:

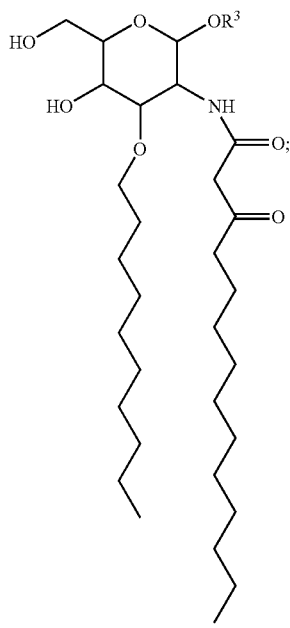

(e) selectively protecting the amide intermediate formed in step (d) under suitable conditions to effect formation of a protected intermediate having the structure:

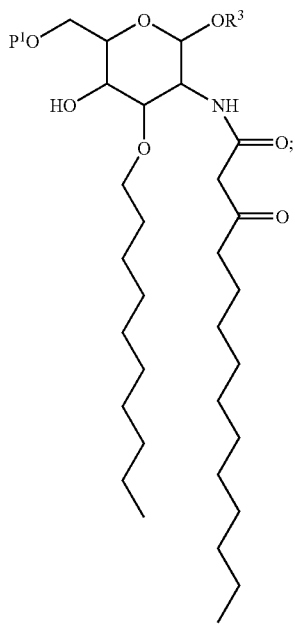

wherein P¹ is a suitable oxygen protecting group;

(f) reacting the protected intermediate formed in step (e) with a suitable reagent under suitable conditions to effect formation of a carbonic acid allyl ester intermediate having the structure:

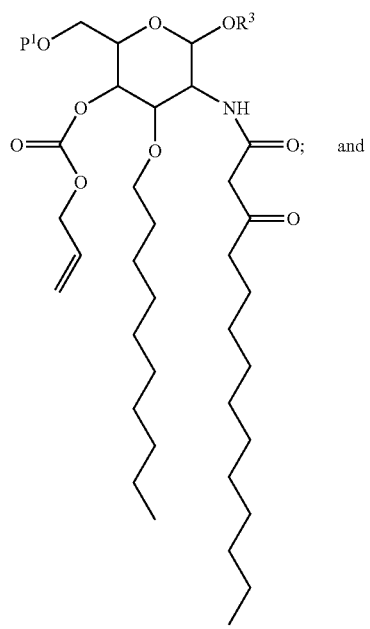 and (g) deprotecting the intermediate formed in step (f) under suitable conditions to effect formation of the saccharide having the structure:

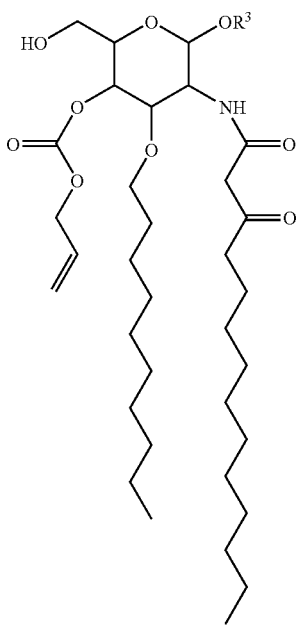

In certain other exemplary embodiments, the saccharide having the structure:

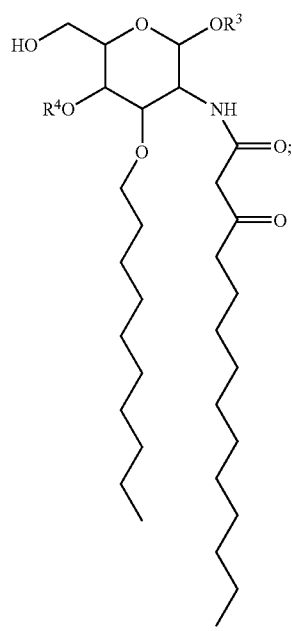

wherein $R^3$ and $R^4$ are each independently a suitable oxygen protecting group;

is prepared by a process comprising steps of:

(a) reacting a saccharide having the structure:

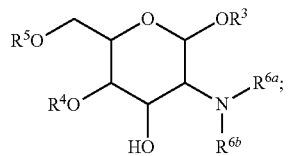

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and $R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;

with a suitable decanyl derivative to effect formation of a decanyl ether having the structure:

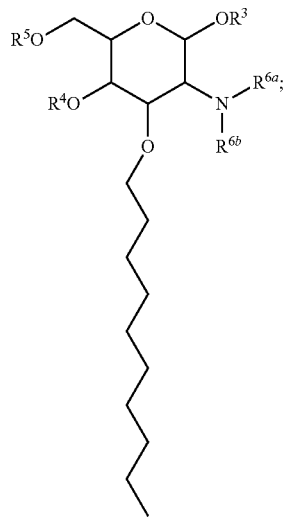

(b) deprotecting the amide moiety of the decanyl ether intermediate formed in step (a) under suitable conditions to effect formation of an amine having the structure:

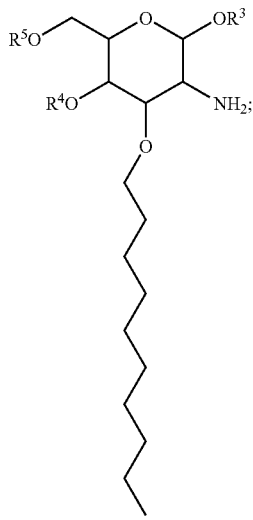

(c) reacting the amine intermediate formed in step (b) with a suitable 3-Oxo-tetradecanoic acid derivative under suitable conditions to effect formation of an amide intermediate having the structure:

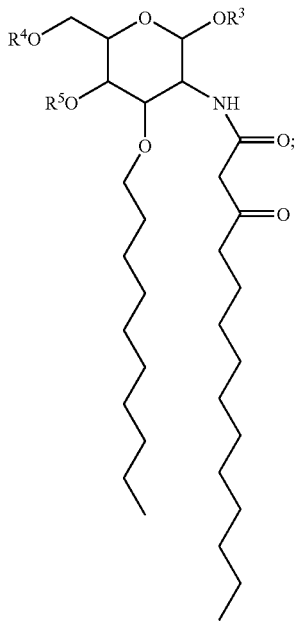

(d) deprotecting the intermediate formed in step (c) under suitable conditions to effect formation of a partially deprotected amide intermediate having the structure:

(e) selectively protecting the amide intermediate formed in step (d) under suitable conditions to effect formation of a protected intermediate having the structure:

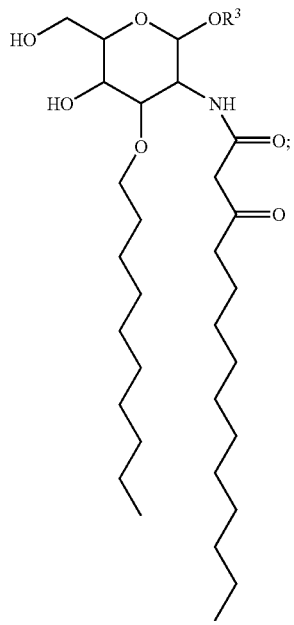

wherein P¹ is a suitable oxygen protecting group;

(f) reacting the protected intermediate formed in step (e) with a suitable reagent under suitable conditions to effect formation of a carbonic acid allyl ester intermediate having the structure:

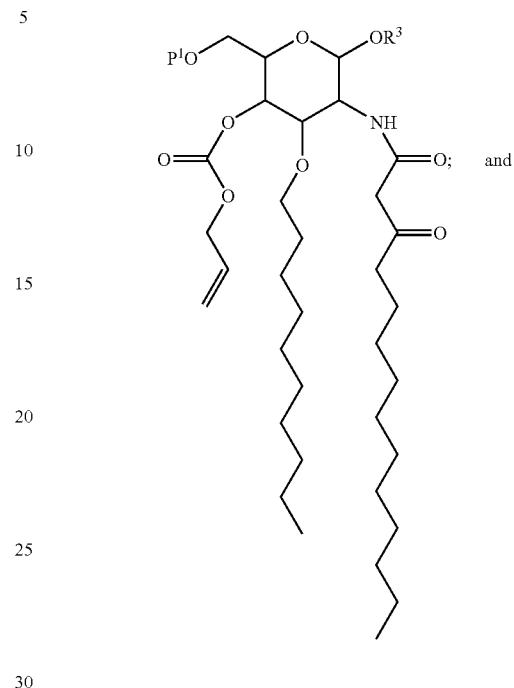

(g) deprotecting the intermediate formed in step (f) under suitable conditions to effect formation of the saccharide having the structure:

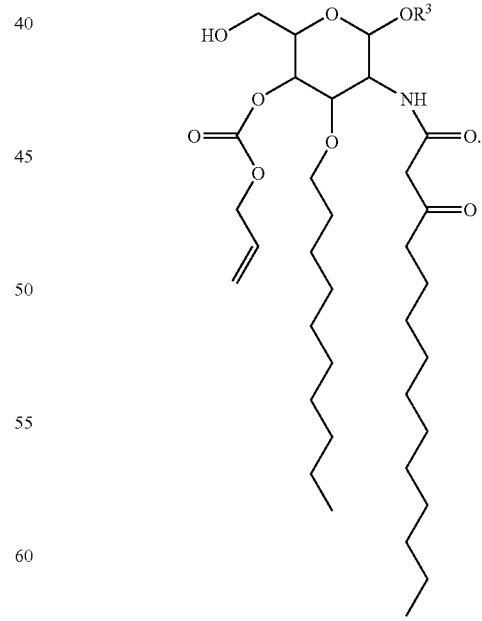

In certain embodiments, the invention provides a method for preparing B1287 and the method comprises steps of:

(a) effecting glycosylation of a monosaccharide having the structure:

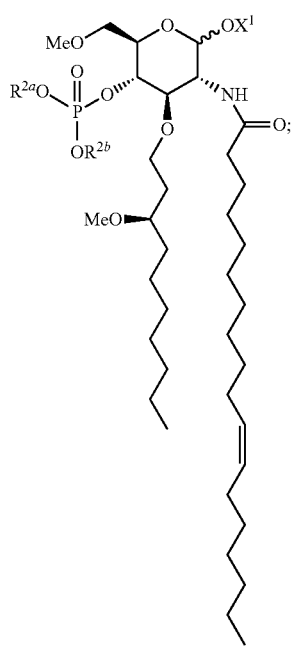

wherein $OX^1$ represents a suitable leaving group for effecting the glycosylation; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

with a monosaccharide having the structure:

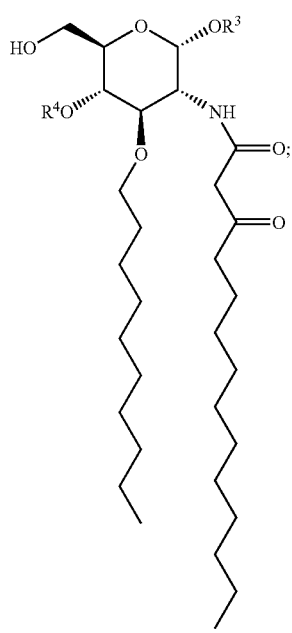

wherein $R^3$ and $R^4$ are each independently a suitable oxygen protecting group;

under suitable conditions to effect formation of a disaccharide having the structure:

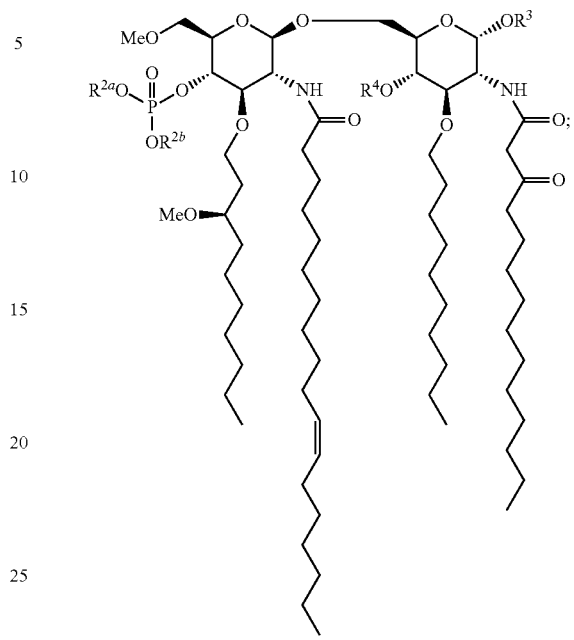

(b) deprotecting the disaccharide formed in step (a) under suitable conditions to effect formation of a partially deprotected disaccharide having the structure:

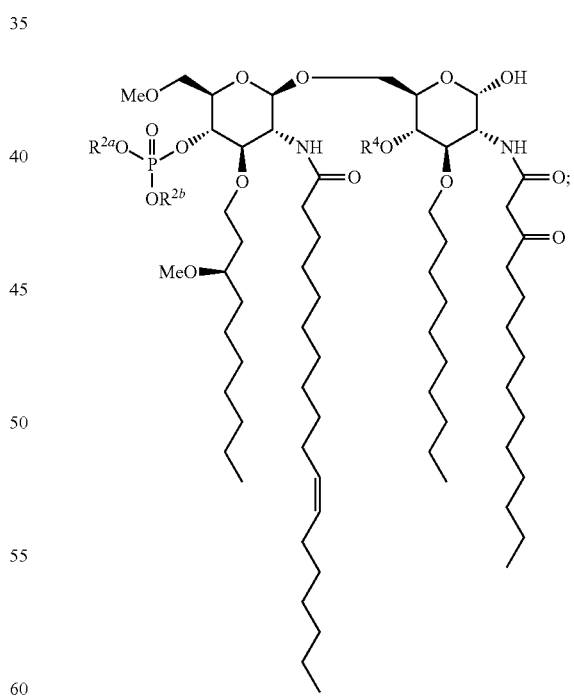

(c) reacting the partially deprotected disaccharide formed in step (b) with a suitable reagent under suitable conditions to effect formation of a diphosphorylated disaccharide having the structure:

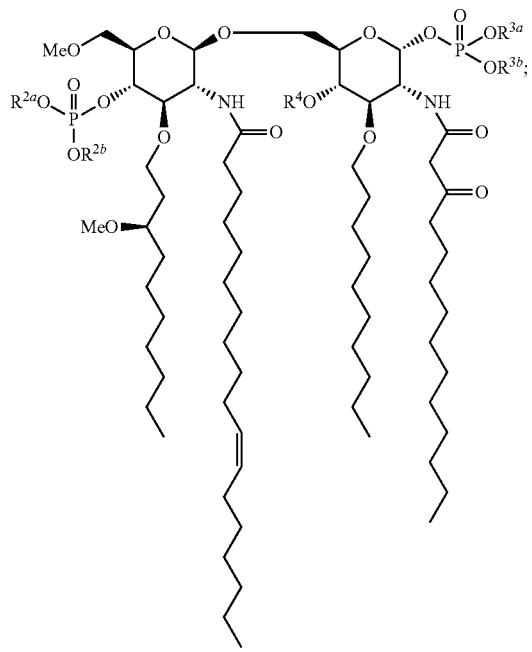

wherein $R^{3a}$ and $R^{3b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (d) treating the diphosphorylated disaccharide formed in step (c) with one or more suitable reagents under suitable conditions to effect formation of a disaccharide having the structure:

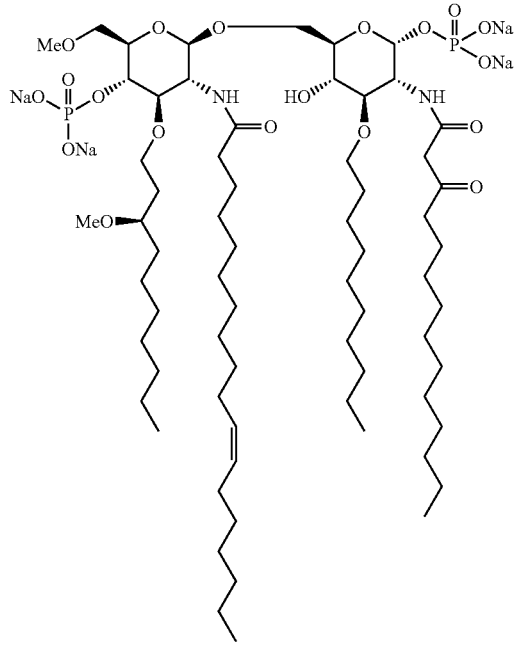

In yet other embodiments, the step of treating the diphosphorylated disaccharide formed in step (c) with one or more suitable reagents under suitable conditions leads to the formation of a compound having the structure:

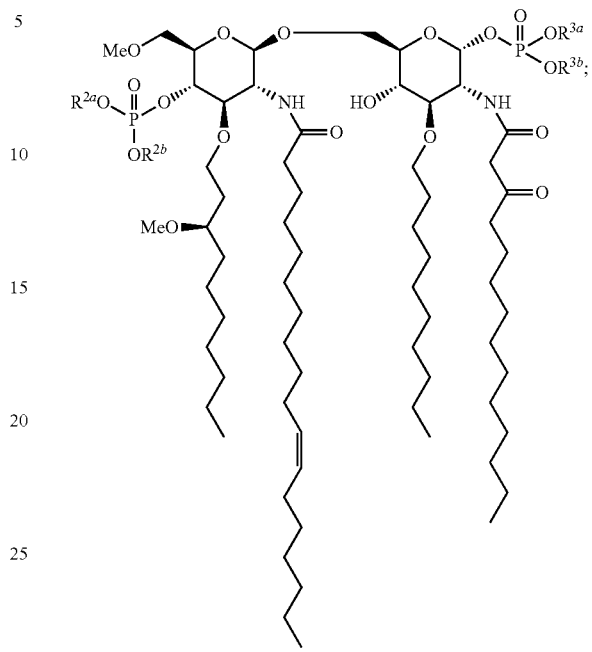

which is then purified to yield the corresponding tetrasodium salt:

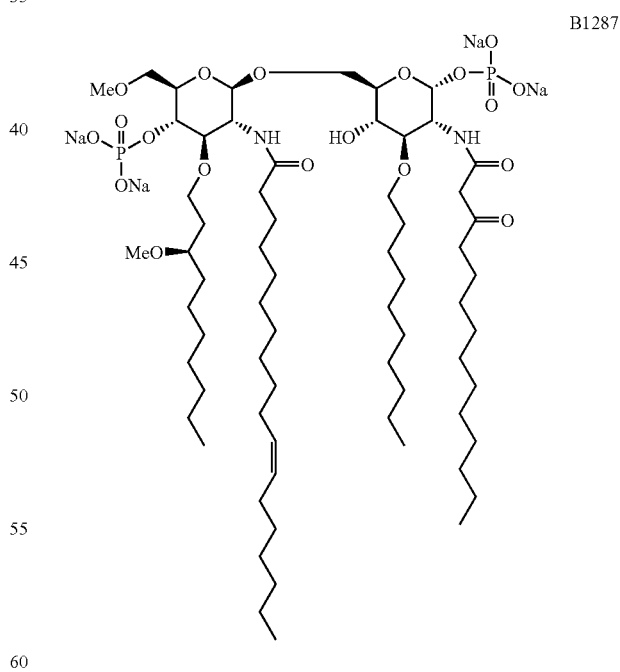

In still other embodiments, the purification process comprises chromatographic separation and treatment with a base. In certain exemplary embodiments, the purification process comprises (i) ion exchange chromatography, (ii) POROS 50 R2, methanol, and (iii) treatment with aqueous NaOH.

In certain exemplary embodiments, the saccharide having the structure:

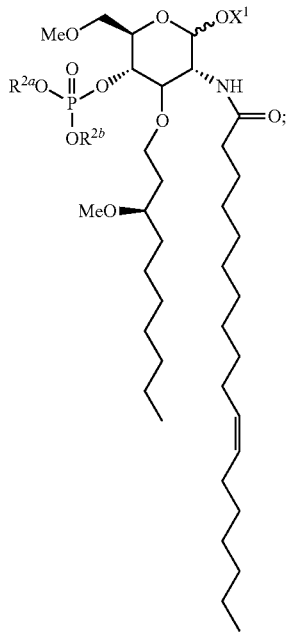

wherein $OX^1$ represents a suitable leaving group for effecting a glycosylation reaction; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

is prepared by a process comprising steps of:

(a) reacting an amine having the structure:

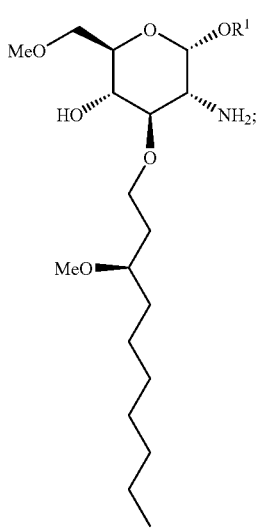

wherein $R^1$ is a suitable oxygen protecting group;

with a suitable vaccenoyl acid derivative to effect formation of an amide intermediate having the structure:

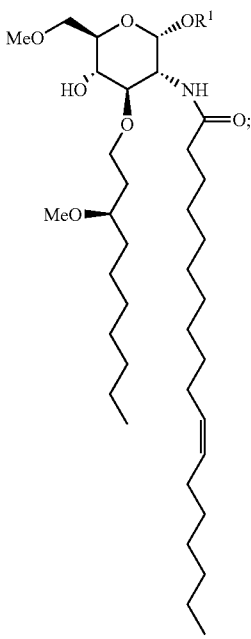

(b) reacting the amide intermediate formed in step (a) with a suitable reagent to effect formation of a phosphorylated saccharide having the structure:

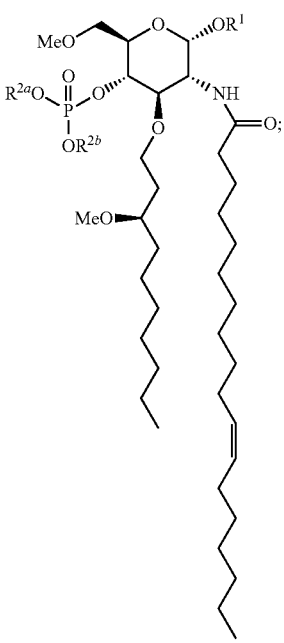

wherein $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (c) deprotecting the phosphorylated saccharide formed in step (b) under suitable conditions to effect formation of an alcohol intermediate having the structure:

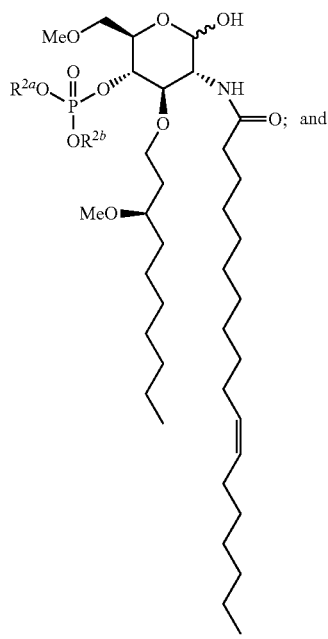

(d) reacting the alcohol intermediate formed in step (c) under suitable conditions to effect formation of a saccharide having the structure:

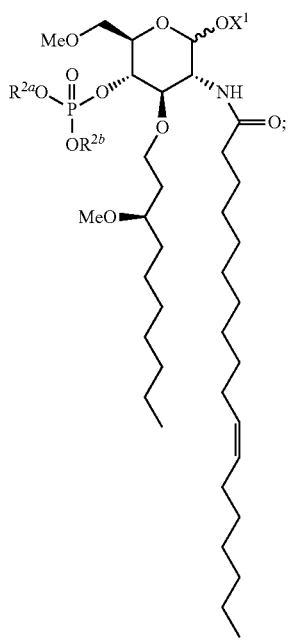

wherein OX¹ represents a suitable leaving group for effecting a glycosylation reaction.

In yet other embodiments, the saccharide having the structure:

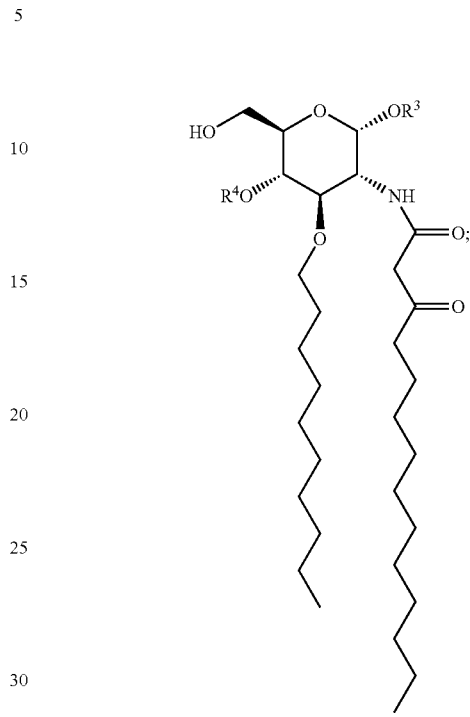

wherein $R^3$ and $R^4$ are each independently a suitable oxygen protecting group;

is prepared by a process comprising steps of:

(a) reacting a saccharide having the structure:

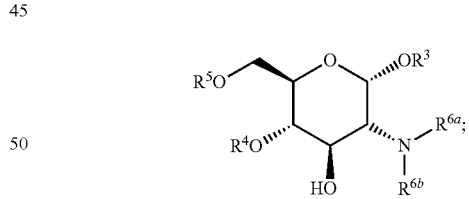

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and $R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;

with a suitable decanyl derivative to effect formation of a decanyl ether having the structure:

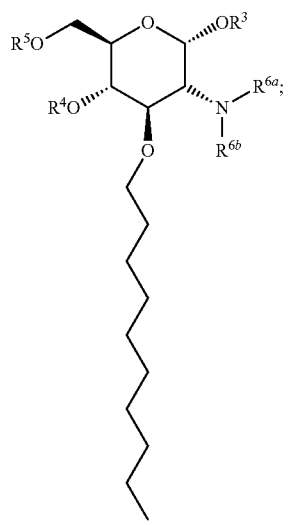

(b) deprotecting the decanyl ether formed in step (a) under suitable conditions to effect formation of a partially deprotected intermediate having the structure:

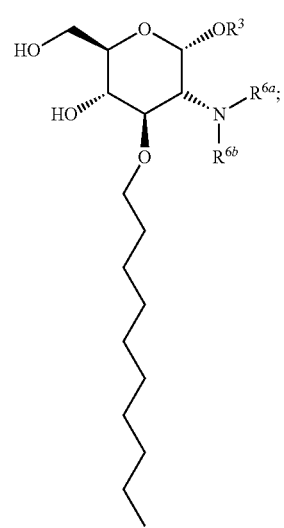

(c) deprotecting the amide moiety of the intermediate formed in step (b) under suitable conditions to give an amine intermediate having the structure:

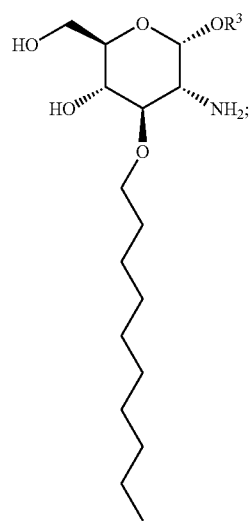

(d) reacting the amine intermediate formed in step (c) with a suitable 3-Oxo-tetradecanoic acid derivative under suitable conditions to effect formation of an amide intermediate having the structure:

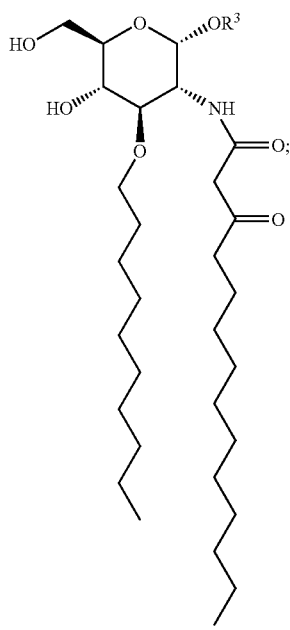

(e) selectively protecting the amide intermediate formed in step (d) under suitable conditions to effect formation of a protected intermediate having the structure:

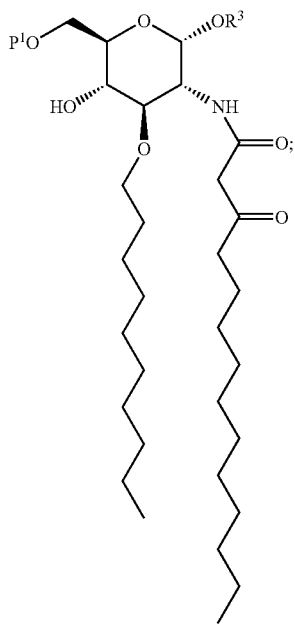

wherein $P^1$ is a suitable oxygen protecting group;

(f) reacting the protected intermediate formed in step (e) with a suitable reagent under suitable conditions to effect formation of a carbonic acid allyl ester intermediate having the structure:

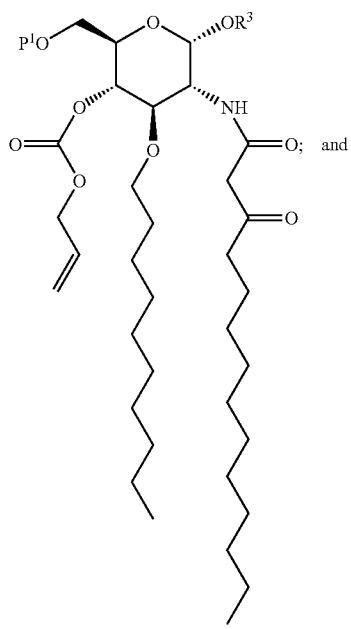

(g) deprotecting the intermediate formed in step (f) under suitable conditions to effect formation of the saccharide having the structure:

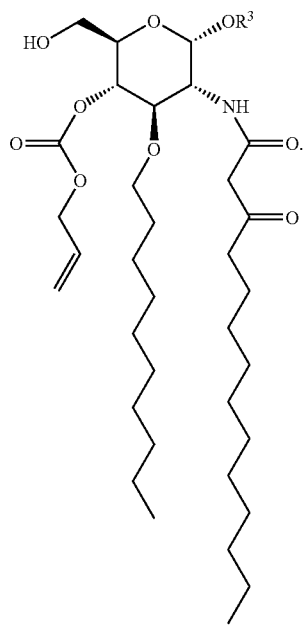

In certain other exemplary embodiments, the saccharide having the structure:

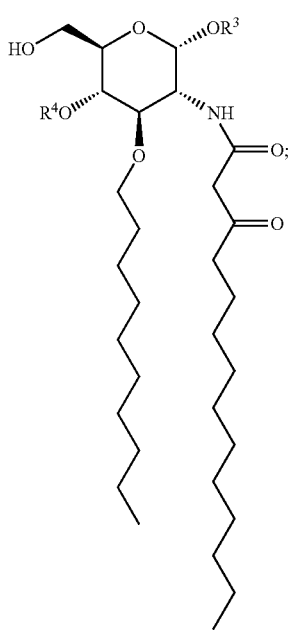

wherein $R^3$ and $R^4$ are each independently a suitable oxygen protecting group;

is prepared by a process comprising steps of:

(a) reacting a saccharide having the structure:

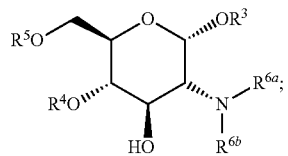

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and $R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen; with a suitable decanyl derivative to effect formation of a decanyl ether having the structure:

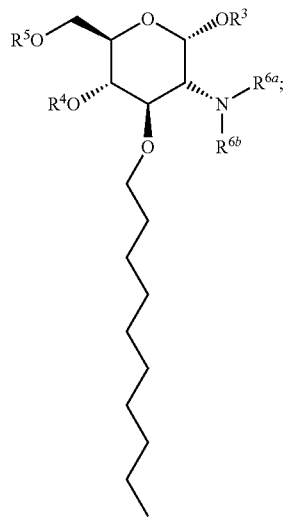

(b) deprotecting the amide moiety of the decanyl ether intermediate formed in step (a) under suitable conditions to effect formation of an amine having the structure:

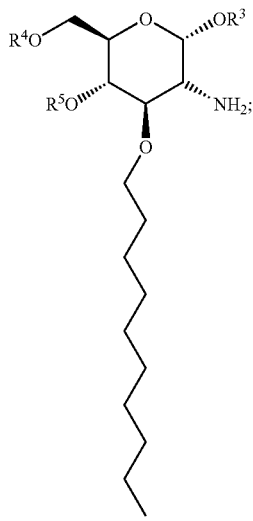

(c) reacting the amine intermediate formed in step (b) with a suitable 3-Oxo-tetradecanoic acid derivative under suitable conditions to effect formation of an amide intermediate having the structure:

(d) deprotecting the intermediate formed in step (c) under suitable conditions to effect formation of a partially deprotected amide intermediate having the structure:

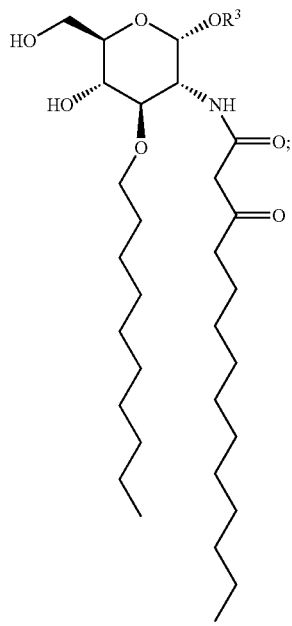

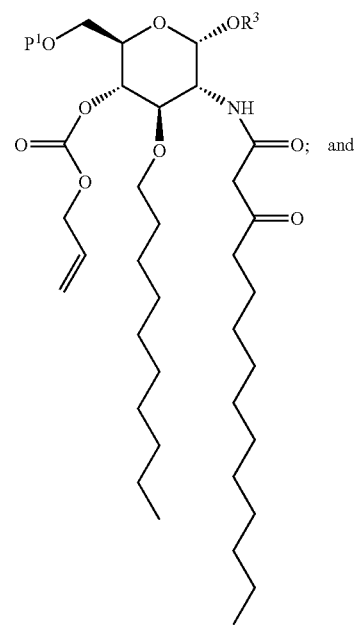

(e) selectively protecting the amide intermediate formed in step (d) under suitable conditions to effect formation of a protected intermediate having the structure:

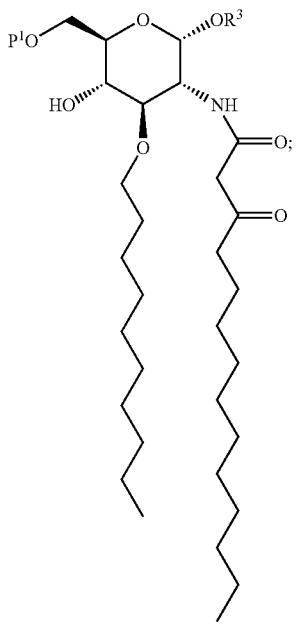

wherein $P^1$ is a suitable oxygen protecting group;

(f) reacting the protected intermediate formed in step (e) with a suitable reagent under suitable conditions to effect formation of a carbonic acid allyl ester intermediate having the structure:

(g) deprotecting the intermediate formed in step (f) under suitable conditions to effect formation of the saccharide having the structure:

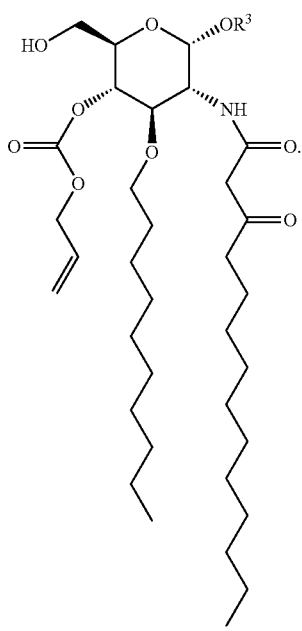

DEFINITIONS

In accordance with the present invention and as used herein, the following terms, are defined with the following meanings, unless explicitly stated otherwise.

Certain compounds disclosed in the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g. O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether)), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

The term "silyl protecting group", as used herein, refers to any silicon-containing oxygen protecting group. Typically, a silyl protecting group is one that forms a silyl ether upon reaction with the hydroxyl group that it is meant to protect. Silyl protecting groups include, but are not limited to, trialkylsilyl, dialkylarylsilyl, heteroalkyldiarylsilyl, alkyldiarylsilyl, dialkylheteroarylsilyl, alkyldiheteroarylsilyl, triarylsilyl, triheteroarylsilyl protecting groups. See, for example, "Protective Groups in Organic Synthesis" Third Ed. Greene, T. W. and Wuts, P. G., Eds., John Wiley & Sons, New York: 1999, pp. 113-148.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl or cycloalkyl group, as previously defined, attached to the parent molecular moiety through an oxygen atom or through a sulfur atom. In certain embodiments, the alkyl or cycloalkyl group contains 1-20 aliphatic or alicyclic carbon atoms. In certain other embodiments, the alkyl or cycloalkyl group contains 1-10 aliphatic or alicyclic carbon atoms. In yet other embodiments, the alkyl, alkenyl, and alkynyl groups employed in the invention contain 1-8 aliphatic or alicyclic carbon atoms. In still other embodiments, the alkyl group contains 1-6 aliphatic or alicyclic carbon atoms. In yet other embodiments, the alkyl group contains 1-4 aliphatic or alicyclic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure NHR' wherein R' is alkyl or cycloalkyl, as defined herein. The term "dialkylamino" refers to a group having the structure —N(R')$_2$, wherein each occurrence of R' is independently alkyl or cycloalkyl, as defined herein. The term "aminoalkyl" refers to a group having the structure NH$_2$R'—, wherein R' is alkyl or cycloalkyl, as defined herein. In certain embodiments, the alkyl group: contains 1-20 aliphatic or alicyclic carbon atoms. In certain other embodiments, the alkyl or cycloalkyl group contains 1-10 aliphatic or alicyclic carbon atoms. In yet other embodiments, the alkyl, alkenyl, and alkynyl groups employed in the invention contain 1-8 aliphatic or alicyclic carbon atoms. In still other embodiments, the alkyl or cycloalkyl group contains 1-6 aliphatic or alicyclic carbon atoms. In yet other embodiments, the alkyl or cycloalkyl group contains 1-4 aliphatic or alicyclic carbon atoms. Examples of alkylamino include, but are not limited to, methylamino, ethylamino, isopropylamino and the like.

Some examples of substituents of the above-described aliphatic (and other) moieties of compounds disclosed in the present invention include, but are not limited to aliphatic; alicyclic; heteroaliphatic; heteroalicyclic; aryl; heteroaryl; alkylaryl; alkylheteroaryl; alkoxy; alkylamino, dialkylamino, aminoalkyl, aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an alkyl or heteroalkyl moiety and thus also include -(alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(alkyl)aryl, -(heteroalkyl) aryl, -(heteroalkyl)aryl, and -(heteroalkyl)heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic, rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additionally, it will be appreciated, that any two adjacent groups taken together may represent a 4, 5, 6, or 7-membered, substituted or unsubstituted alicyclic or heteroalicyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other alicyclic, heteroalicyclic or heterocyclic moieties, may optionally be substituted with substituents including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. An analogous convention applies to other generic terms such as "cycloalkenyl", "cycloalkynyl" and the like. Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g. in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroalicyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a substituted or unsubstituted aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more of the hydrogen atoms thereon with but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples that are described herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

Further, B1287 contains asymmetric carbon atoms and hence can exist as stereoisomers, both enantiomers and diastereomers. One of ordinary skill in the art will recognize that the inventive method may be adapted to the preparation of any of all possible stereoisomers of B1287. While the examples provided herein disclose the preparation of a particular isomer, methods for preparing other stereoisomers of B1287 are considered to fall within the scope of the present invention.

DETAILED DESCRIPTION OF CERTAIN PREFERRED EMBODIMENTS OF THE INVENTION

In one aspect, the present invention provides a method for synthesizing LPS antagonist B1287 having the structure:

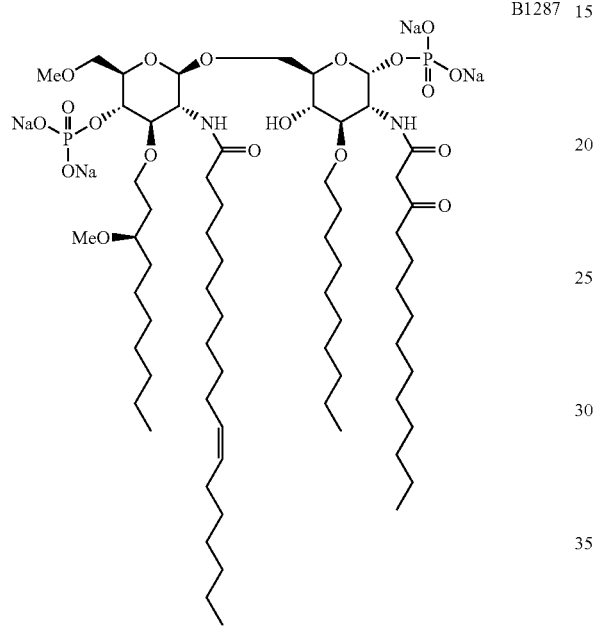

B1287

B1287 is a potent LPS antagonist, and thus the compound is useful for the prophylactic and affirmative treatment of any LPS-mediated disorder. These disorders include, but are not limited to, sepsis, septicemia (including but not limited to endotoxemia), endotoxemia resulting from gram negative bacteremia (with its accompanying symptoms of fever, generalized inflammation, disseminated intravascular coagulation, hypotension, acute renal failure, acute respiratory distress syndrome, adult respiratory distress syndrome (ARDS), hepatocellular destruction and/or cardiac failure) and various forms of septic shock (including but not limited to endotoxic shock). In addition, the title compound may be useful in the prophylactic or affirmative treatment of localized or systemic inflammatory response to infection by different types of organisms, including gram negative bacteria, and in diseases related to translocation of gram negative bacteria or endotoxin from the gut. Together these disorders are termed systemic inflammatory response syndrome or SIRS (For a discussion of these terms, see Bone, et al., Chest 1992; 101: 1644-55).

In another aspect, the invention encompasses methods for synthesizing any stereoisomer of LPS antagonist B1287. Thus there is provided herein a method for preparing a compound having the structure:

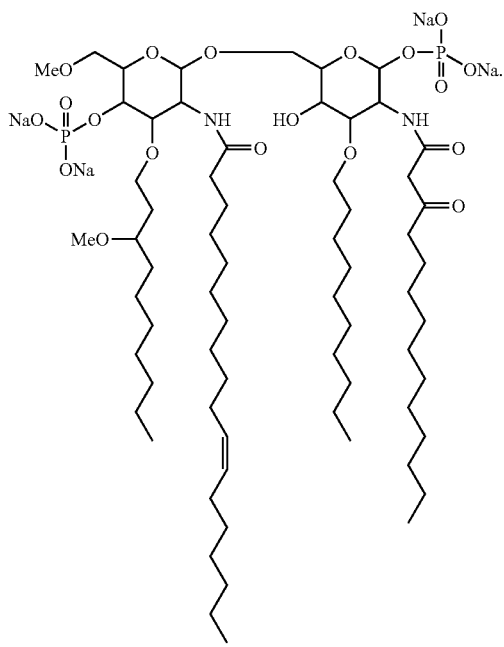

In certain embodiments, the inventive method comprises steps of:

(a) effecting glycosylation of a monosaccharide having the structure:

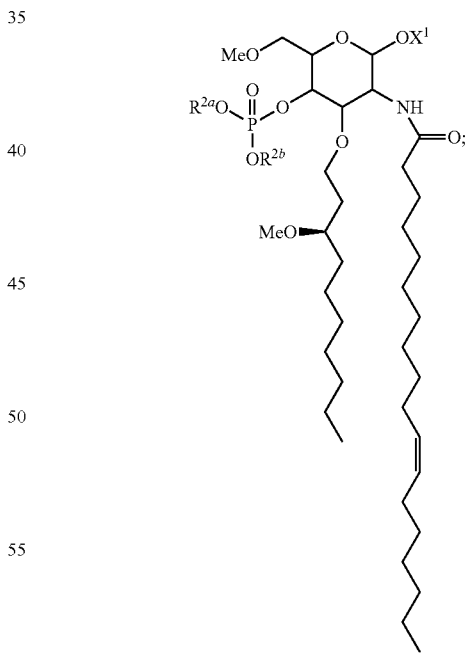

wherein $OX^1$ represents a suitable leaving group for effecting the glycosylation; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

with a monosaccharide having the structure:

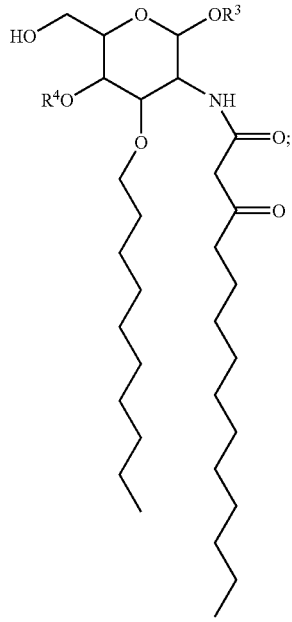

wherein $R^3$ and $R^4$ are each independently a suitable oxygen protecting group;

under suitable conditions to effect formation of a disaccharide having the structure:

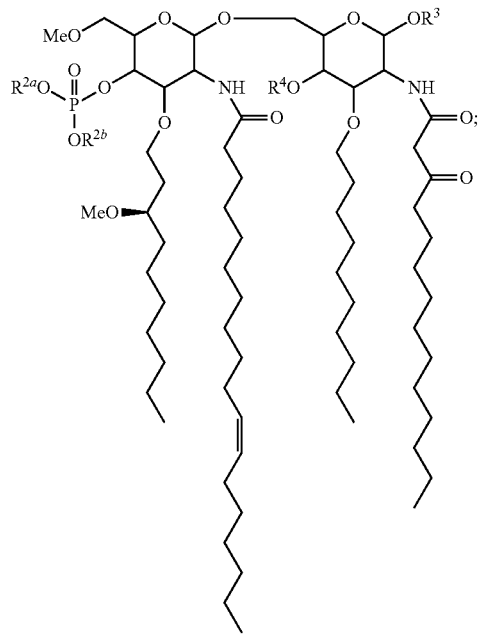

(b) deprotecting the disaccharide formed in step (a) under suitable conditions to effect formation of a partially deprotected disaccharide having the structure:

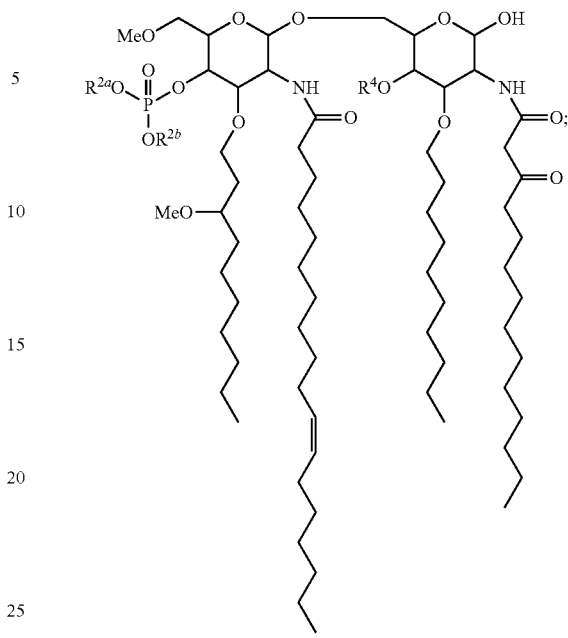

(c) reacting the partially deprotected disaccharide formed in step (b) with a suitable reagent under suitable conditions to effect formation of a diphosphorylated disaccharide having the structure:

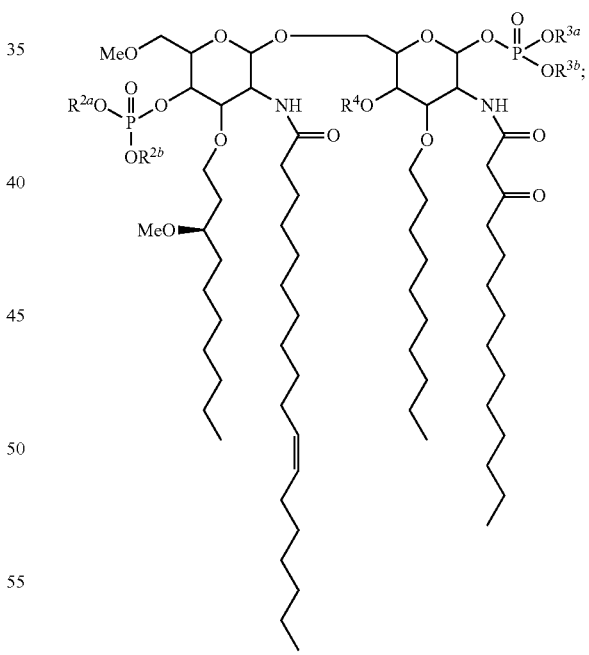

wherein $R^{3a}$ and $R^{3b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (d) treating the diphosphorylated disaccharide formed in step (c) with one or more suitable reagents under suitable conditions to effect formation of a disaccharide having the structure:

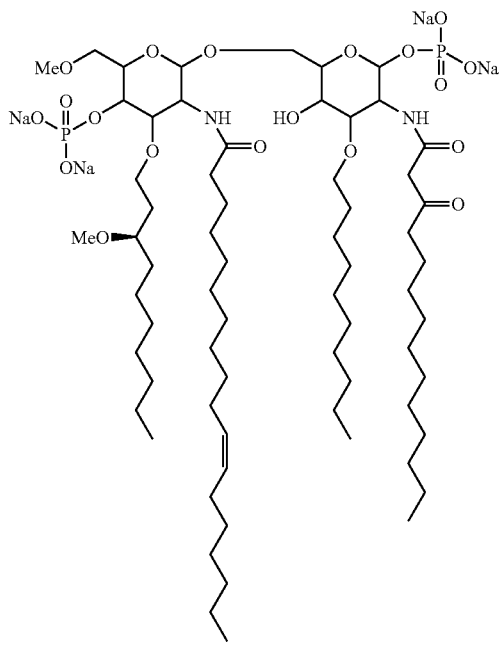

In yet other embodiments, the step of treating the diphosphorylated disaccharide formed in step (c) with one or more suitable reagents under suitable conditions leads to the formation of a compound having the structure:

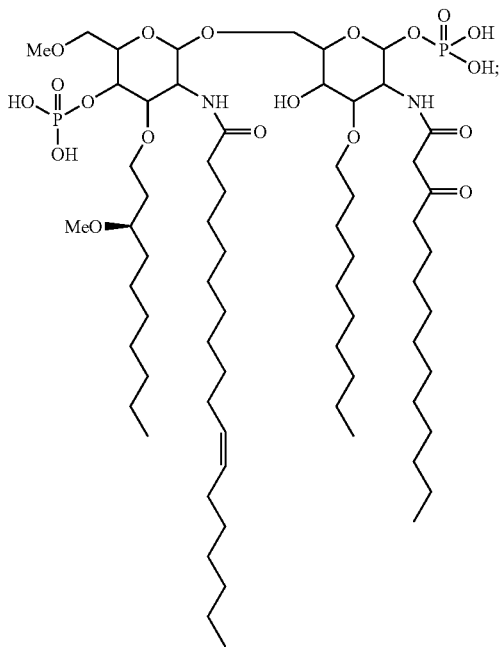

which is then purified to yield the corresponding tetrasodium salt:

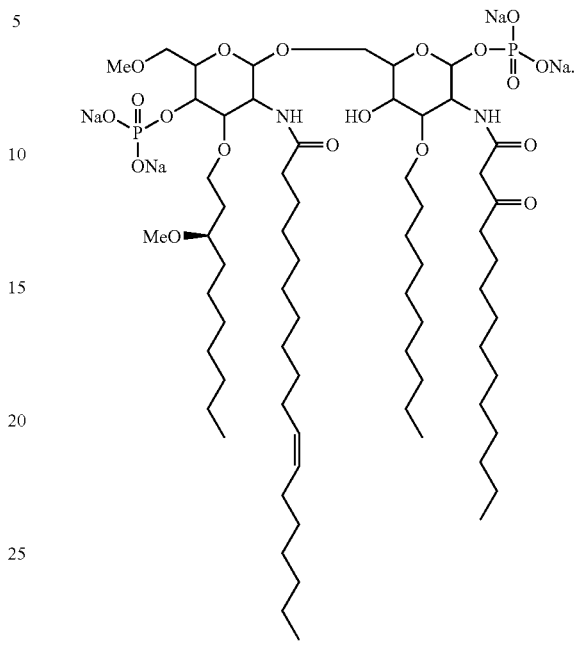

In certain embodiments, $X^1$ is alkyl, alkenyl, alkynyl, heteroalkyl, heteroalkenyl, heteroalkynyl, aryl, heteroaryl, silyl, —C(=O)$R^{X1A}$, —C(=S)$R^{X1A}$, —C(=N$R^{X1A}$)$R^{X1B}$, —SO$_2$$R^{X1A}$, wherein $R^{X1A}$ and $R^{X1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —NR$^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $X^1$ is —C(=N$R^{X1A}$)$R^{X1B}$ or —SO$_2$$R^{X1A}$, wherein $R^{X1A}$ and $R^{X1B}$ are each independently hydrogen or an aliphatic, alicyclic, heteroaliphatic, heteroalicyclic, aryl or heteroaryl moiety. In certain exemplary embodiments, $X^1$ is —C(=N$R^{X1A}$)$R^{X1B}$ wherein $R^{X1A}$ and $R^{X1B}$ are each independently hydrogen or substituted or unsubstituted lower alkyl. In certain exemplary embodiments, $R^{X1A}$ is hydrogen and $R^{X1B}$ is substituted or unsubstituted lower alkyl. In certain exemplary embodiments, $R^{X1A}$ is hydrogen and $R^{X1B}$ is —CX$_3$, wherein X represents a halogen atom. In certain exemplary embodiments, $R^{X1A}$ is hydrogen, $R^{X1B}$ is —CCl$_3$, and $X^1$ is —C(=NH)CCl$_3$. In certain exemplary embodiments, $X^1$ is —C(=NH)CCl$_3$ and the glycosylation step (a) is conducted under strongly acidic conditions. In certain exemplary embodiments, the glycosylation conditions comprise an organic sulfonic acid and a suitable solvent. In certain embodiments, the organic sulfonic acid is an alkanesulfonic acid. In certain embodiments, the alkyl sulfonic acid is MeSO$_3$H or EtSO$_3$H. In certain embodiments, the solvent is an apolar solvent. In certain exemplary embodiments, the apolar solvent is toluene, hexane or combination thereof. In certain embodiments, the glycosylation conditions comprise zinc triflate (Zn(OTf)$_2$) and a suitable solvent. In certain exemplary embodiments, the glycosylation conditions comprise zinc triflate (Zn(OTf)$_2$) and methylene chloride. In yet other embodiments, the glycosylation conditions comprise silver triflate (AgOTf) and a suitable solvent. In still other embodiments, the glycosylation conditions comprise silver triflate (AgOTf) and methylene chloride. In certain embodiment, in the glycosylation step (a), the monosaccharide having the structure:

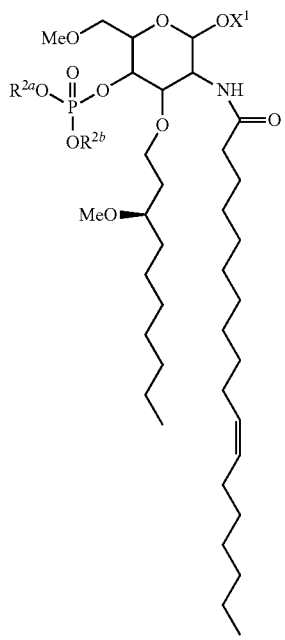

is used in excess. In certain embodiments, between 1.1 to about 3.0 equivalents of the monosaccharide described directly above are used. In certain other embodiments, between 1.2 to about 2.9 equivalents are used. In certain other embodiments, between 1.3 to about 2.8 equivalents are used. In certain other embodiments, between 1.5 to about 2.5 equivalents are used. In certain other embodiments, between 1.6 to about 2.3 equivalents are used. In certain exemplary embodiments, between 1.8 to about 2.0 equivalents are used.

In certain embodiments, R$^3$ is alkyl, alkenyl, alkynyl, heteroalkyl, heteroalkenyl, heteroalkynyl, aryl, heteroaryl, silyl, —C(=O)R$^x$, —C(=S)R$^x$, —C(=NR$^x$)R$^y$, —SO$_2$R$^x$, wherein R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, R$^3$ is a substituted or unsubstituted lower alkenyl moiety. In certain exemplary embodiments, R$^3$ is a moiety having the structure:

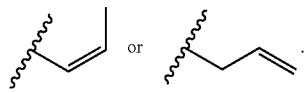

In certain embodiments, the reaction conditions used in deprotection step (b) comprise a strong acid in a suitable solvent. In certain exemplary embodiments, the strong acid is HF and the solvent is acetonitrile.

In certain exemplary embodiments, R$^3$ is a moiety having the structure:

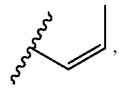

and the reaction conditions of deprotection step (b) comprise a strong acid in a suitable solvent. In certain exemplary embodiments, the strong acid is HF and the solvent is acetonitrile.

In certain other embodiments, the reagent in step (c) is a phosphorylating agent. In certain embodiments, the recation conditions in step (c) comprise bis(allyloxy)diisopropyl aminophosphine and an oxidizing agent. In certain exemplary embodiments, the oxidizing agent is Oxone.

In certain embodiments, R$^{2a}$, R$^{2b}$, R$^{3a}$ and R$^{3b}$ are each independently a substituted or unsubstituted alkenyl moiety. In certain exemplary embodiments, R$^{2a}$, R$^{2b}$, R$^{3a}$ and R$^{3b}$ are each allyl.

In yet other embodiments, R$^4$ is alkyl, alkenyl, alkynyl, heteroalkyl, heteroalkenyl, heteroalkynyl, aryl, heteroaryl, silyl, —C(=O)R$^x$, —C(=S)R$^x$, —C(=NR$^x$)R$^y$, —SO$_2$R$^x$, wherein R$^x$ and R$^y$ are each independently hydrogen, alkyl, alkenyl, alkynyl, cycloalkyl; cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, R$^4$ is —C(=O)OR$^A$, wherein R$^A$ is substituted or unsubstituted alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl. In certain exemplary embodiments, R$^4$ is —C(=O)OR$^x$, wherein R$^x$ is substituted or unsubstituted alkyl, alkenyl. In certain exemplary embodiments, R$^x$ is allyl, and R$^4$ is —C(=O)OCH$_2$CH=CH$_2$.

In certain other embodiments, R$^{2a}$, R$^{2b}$, R$^{3a}$ and R$^{3b}$ are each allyl, R$^4$ is —C(=O)OCH$_2$CH=CH$_2$ and the deprotection conditions in step (d) comprise Pd(PPH$_3$) in a suitable solvent. In certain exemplary embodiments, the treating conditions in step (d) further comprise triphenyl phosphine and acetic acid.

In still other embodiments, purification of the compound having the structure:

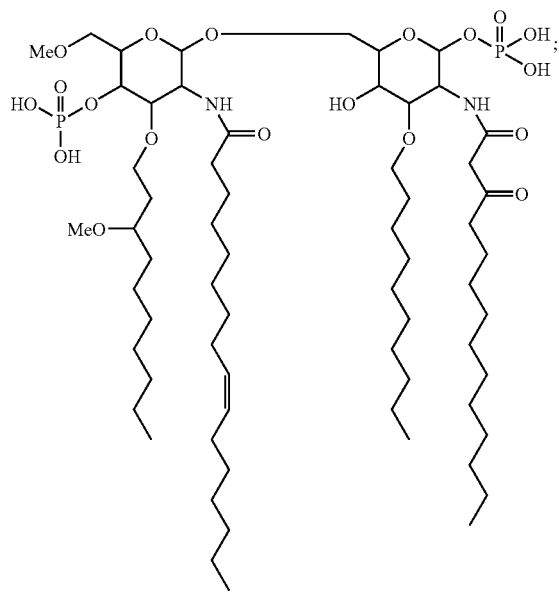

comprises chromatographic separation and treatment with a base. In certain exemplary embodiments, the purification process comprises (i) ion exchange chromatography, (ii) POROS 50 R2, methanol, and (iii) treatment with aqueous NaOH.

In certain exemplary embodiments, the saccharide having the structure:

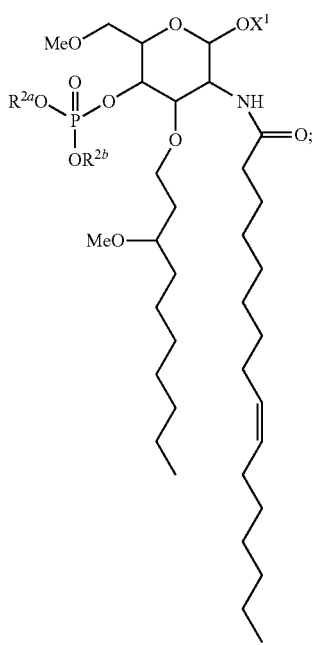

wherein $OX^1$ represents a suitable leaving group for effecting a glycosylation reaction; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

is prepared by a process comprising steps of:

(a) reacting an amine having the structure:

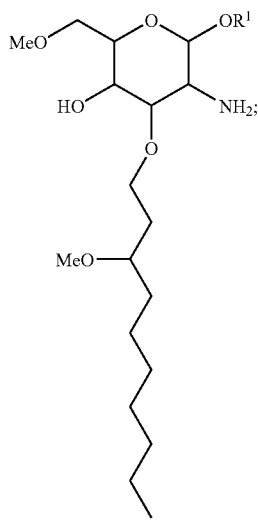

wherein $R^1$ is a suitable oxygen protecting group;

with a suitable vaccenoyl acid derivative to effect formation of an amide intermediate having the structure:

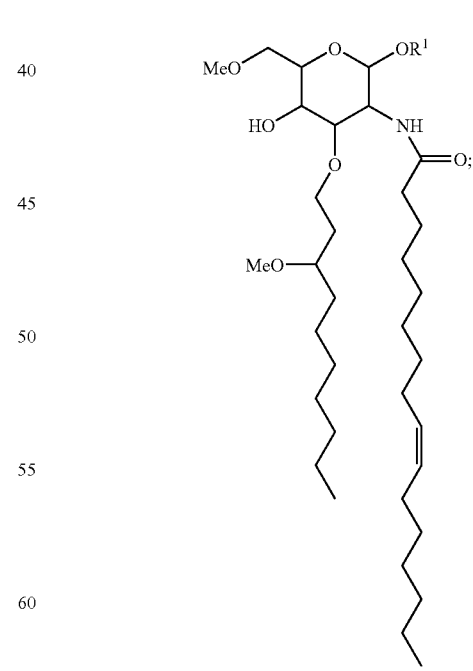

(b) reacting the amide intermediate formed in step (a) with a suitable reagent to effect formation of a phosphorylated saccharide having the structure:

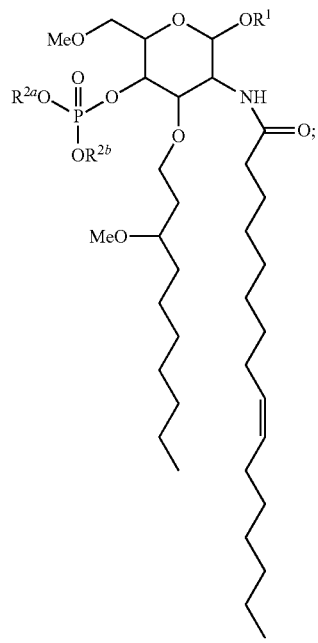

wherein $R^{2a}$ and $R^{2b}$ are each independently allyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (c) deprotecting the phosphorylated saccharide formed in step (b) under suitable conditions to effect formation of an alcohol intermediate having the structure:

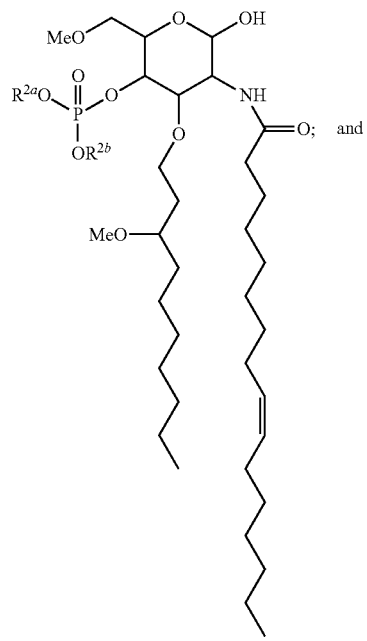

and (d) reacting the alcohol intermediate formed in step (c) under suitable conditions to effect formation of a saccharide having the structure:

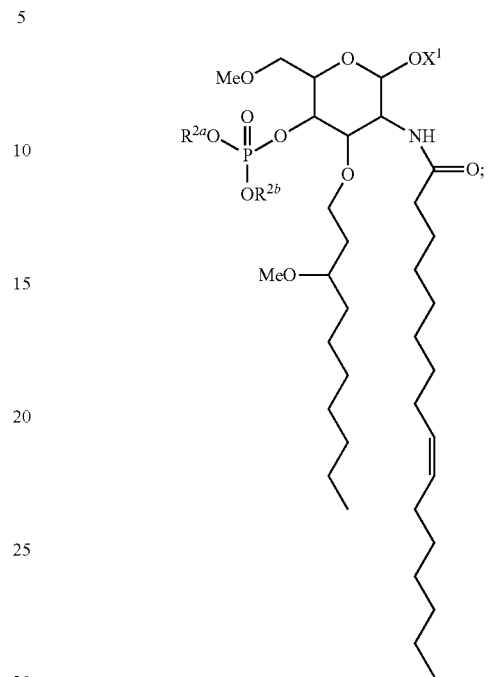

wherein $OX^1$ represents a suitable leaving group for effecting a glycosylation reaction.

In certain embodiments, $R^1$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^1$ is a substituted or unsubstituted lower alkenyl moiety. In certain exemplary embodiments, $R^1$ is a moiety having the structure:

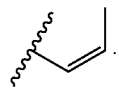

In certain embodiments, the vaccenoyl acid derivative of step (a) is a vaccenoyl chloride. In certain exemplary embodiments, the vaccenoyl acid derivative of step (a) is Δ-11-cis-vaccenoyl chloride. In certain other exemplary embodiments, the vaccenoyl acid derivative of step (a) is a vaccenoyl chloride and the reaction conditions for reacting the amine with the vaccenoyl acid derivative in step (a) comprise a weak base. In certain other exemplary embodiments, the vaccenoyl acid derivative of step (a) is Δ-11-cis-vaccenoyl chloride and the reaction conditions for reacting the amine with the vaccenoyl acid derivative in step (a) comprise a weak base. In certain exemplary embodiments, the vaccenoyl acid derivative of step (a) is Δ-11-cis-vaccenoyl chloride. In certain exemplary embodiments, the weak base is aqueous $NaHCO_3$. In certain other exemplary embodiments, the weak base is aqueous $K_2CO_3$.

In certain other embodiments, the reagent in step (b) is a phosphorylating agent In certain exemplary embodiments, the reaction conditions in step (b) comprise bis(allyloxy) diisopropyl aminophosphine and an oxidizing agent. In certain exemplary embodiments, the oxidizing agent is Oxone. In certain other exemplary embodiments, the reaction conditions in step (b) further comprise tetrazole. In certain other exemplary embodiments, the reaction conditions in step (b) comprise bis(allyloxy)diisopropyl aminophosphine (DPP), pyridinium trifluoroacetate and an oxidizing agent. In certain exemplary embodiments, the oxidizing agent is hydrogen peroxide.

In certain embodiments, $R^{3a}$, $R^{3b}$, $R^{3a}$ and $R^{3b}$ are each independently a substituted or unsubstituted alkenyl moiety. In certain exemplary embodiments, $R^{3a}$, $R^{3b}$, $R^{3a}$ and $R^{3b}$ are each allyl.

In yet other embodiments, $R^1$ is a moiety having the structure:

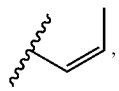

and the deprotection reaction in step (c) comprise strongly acidic conditions. In certain exemplary embodiments, the deprotection conditions in step (c) comprise HCl in a suitable solvent. In certain exemplary embodiments, the solvent is THF or acetonitrile.

In certain exemplary embodiments, $X^1$ is $—C(=NH)R^{X1B}$ wherein $R^{X1B}$ is substituted or unsubstituted lower alkyl, and the step of reacting the alcohol intermediate in step (d) comprises reacting the alcohol intermediate with a moiety having the structure $R^{X1B}CN$ in the presence of a weak base. In certain exemplary embodiments, $X^1$ is $—C(=NH)CX_3$ wherein X represents a halogen atom and the weak base is $K_2CO_3$. In certain exemplary embodiments, $X^1$ is $—C(=NH)CCl_3$.

In yet other embodiments, the saccharide having the structure:

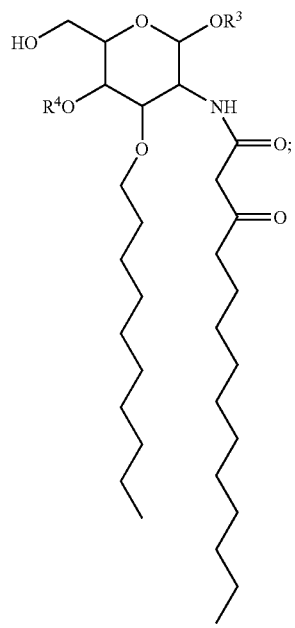

wherein $R^3$ and $R^4$ are each independently a suitable oxygen protecting group;

is prepared by a process comprising steps of:
(a) reacting a saccharide having the structure:

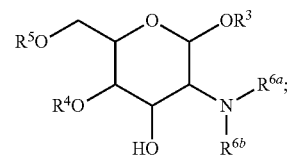

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and
$R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;
with a suitable decanyl derivative to effect formation of a decanyl ether having the structure:

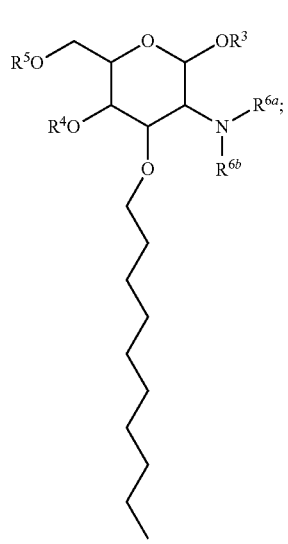

(b) deprotecting the decanyl ether formed in step (a) under suitable conditions to effect formation of a partially deprotected intermediate having the structure:

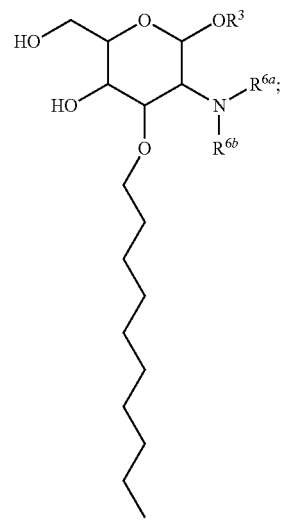

(c) deprotecting the amide moiety of the intermediate formed in step (b) under suitable conditions to give an amine intermediate having the structure:

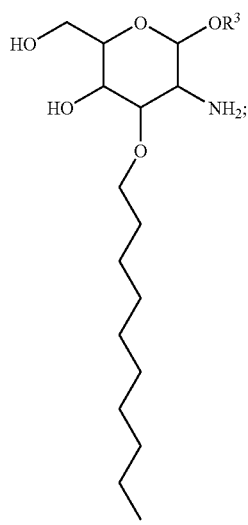

(d) reacting the amine intermediate formed in step (c) with a suitable 3-Oxo-tetradecanoic acid derivative under suitable conditions to effect formation of an amide intermediate having the structure:

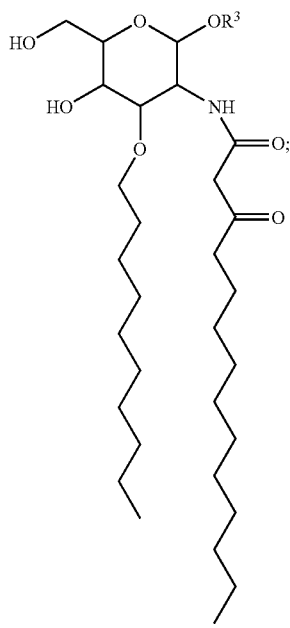

(e) selectively protecting the amide intermediate formed in step (d) under suitable conditions to effect formation of a protected intermediate having the structure:

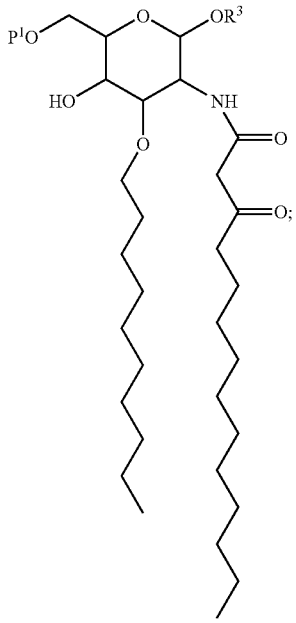

wherein $P^1$ is a suitable oxygen protecting group;

(f) reacting the protected intermediate formed in step (e) with a suitable reagent under suitable conditions to effect formation of a carbonic acid allyl ester intermediate having the structure:

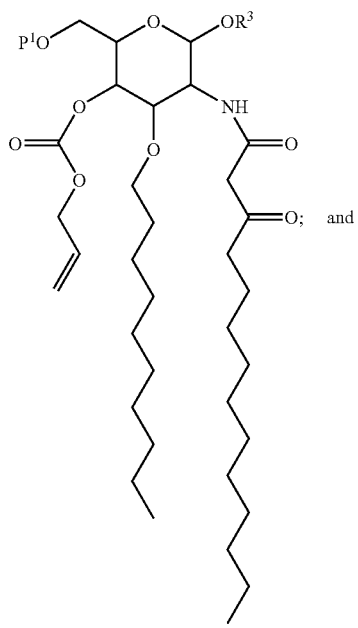

(g) deprotecting the intermediate formed in step (f) under suitable conditions to effect formation of the saccharide having the structure:

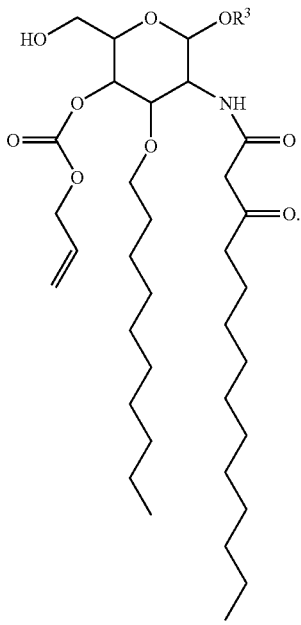

In certain embodiments, $R^3$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ is a substituted or unsubstituted lower alkenyl moiety. In certain exemplary embodiments, $R^3$ is a moiety having the structure:

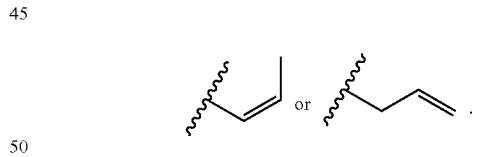

In certain embodiments, $R^4$ and $R^5$ are each independently alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, or $R^4$ and $R^5$, taken together, form a substituted or unsubstituted 5- or 6-membered heterocyclic ring; wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, $R^4$ and $R^5$, taken together, form a substituted or unsubstituted 5- or 6-membered heterocyclic ring. In certain exemplary embodiments, $R^4$ and $R^5$, taken together, form a substituted or unsubstituted 1,3-dioxane moiety. In certain exemplary embodiments, $R^4$ and $R^5$, taken together, form a 2,2-dimethyl-1,3-dioxane moiety.

In certain embodiments, $R^{6a}$ and $R^{6b}$ are each independently hydrogen, alkyl, alkenyl, —C(=O)$R^x$, —C(=O)O$R^x$, —S$R^x$, SO$_2R^x$, or $R^{6a}$ and $R^{6b}$, taken together form a moiety having the structure =CR$^x$R$^y$, wherein $R^{6a}$ and $R^{6b}$ are not simultaneously hydrogen and $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^{6a}$ is hydrogen and $R^{6b}$ is —C(=O)$R^x$, wherein $R^x$ is substituted or unsubstituted lower alkyl. In certain other exemplary embodiments, $R^{6a}$ is hydrogen and $R^{6b}$ is —C(=O)CCX$_3$, wherein X represents a halogen atom. In certain other exemplary embodiments, $R^{6a}$ is hydrogen and $R^{6b}$ is —C(=O)CF$_3$.

In yet other embodiments, the decanyl derivative used in step (a) is a moiety having the structure CH$_3$(CH$_2$)$_9$SO$_2R^x$, wherein $R^x$ is alkyl or aryl. In certain exemplary embodiments, $R^x$ is methyl and the decanyl derivative is decanyl mesylate. In certain other exemplary embodiments, the decanyl derivative is decanyl mesylate and the step of reacting the saccharide in step (a) comprises reacting the saccharide with NaH in a suitable solvent. In certain exemplary embodiments, the solvent is THF/NMP.

In yet other embodiments, the step of deprotecting the decanyl derivative in step (b) comprises subjecting the decanyl derivative to acidic conditions. In certain exemplary embodiments, the step of deprotecting the decanyl derivative in step (b) comprises reacting the decanyl derivative with AcOH in H$_2$O.

In still other embodiments, $R^{6a}$ is hydrogen, $R^{6b}$ is —C(=O)CF$_3$ and the step of deprotecting the amide moiety in step (c) comprises deprotecting the amide moiety in the presence of tBuOK in a suitable solvent, followed by treatment with KOH. In certain embodiments, the solvent is DMSO.

In certain other embodiments, 3-Oxo-tetradecanoic acid derivative in step (d) is 3-Oxo-tetradecanoic acid itself and the reaction conditions comprise reacting the amine intermediate with 3-Oxo-tetradecanoic acid in the presence of EDC in NMP.

In yet other embodiments, $P^1$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $P^1$ is a silyl protecting group. In certain exemplary embodiments, $P^1$ is a trialkylsilyl protecting group. In certain exemplary embodiments, $P^1$ is tert-Butyldimethylsilyl (TBDMS) and the step of selectively protecting the amide intermediate in step (e) comprises reacting the amide intermediate formed in step (d) with tert-Butyldimethylsilyl chloride (TBDMSCl) in the presence of a base in a suitable solvent. In certain exemplary embodiments, the base is imidazole and the solvent is DMF.

In certain other embodiments, $P^1$ is tert-Butyldimethylsilyl (TBDMS) and the step of deprotecting the intermediate formed in step (f) comprises reacting the saccharide having the structure:

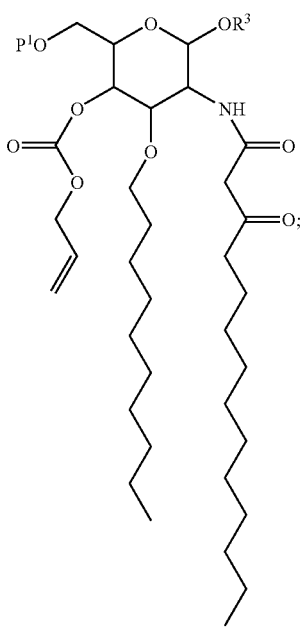

with HOAc in a suitable solvent system. In certain exemplary embodiments, the solvent system is iPrOH/H$_2$O. In certain other embodiments, $P^1$ is tert-Butyldimethylsilyl (TBDMS) and the step of deprotecting the intermediate formed in step (f) comprises reacting the protected saccharide with HF in a suitable solvent. In certain exemplary embodiments, the solvent is methylene chloride. In certain other embodiments, $P^1$ is tert-Butyldimethylsilyl (TBDMS) and the step of deprotecting the intermediate formed in step (f) comprises reacting the protected saccharide with a tetraalkylammonium reagent under fluoride catalysis. In certain exemplary embodiments, the tetraalkylammonium reagent is tetra-N-butyl ammonium fluoride (TBAF).

In still other embodiments, the reagent used in step (i) to effect formation of a carbonic acid allyl ester intermediate comprises a combination of triphosgene and allyl alcohol. In certain exemplary embodiments, the step of reacting the protected intermediate formed in step (e) to form the carbonic acid allyl ester intermediate comprises (i) reacting the protected intermediate with triphosgene in the presence of a base in a suitable solvent, and (ii) trapping the phosgene adduct formed in situ with allyl alcohol under suitable conditions. In certain exemplary embodiments, the base is pyridine and the solvent is toluene.

In certain other exemplary embodiments, the saccharide having the structure:

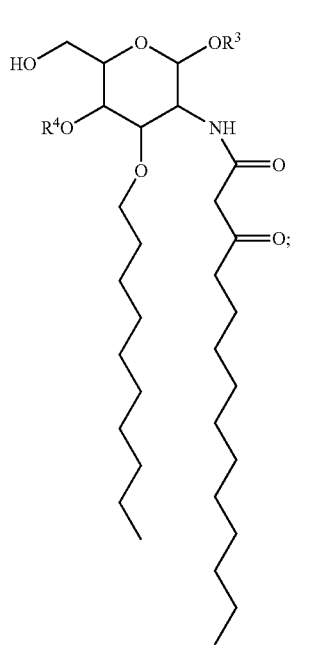

wherein $R^3$ and $R^4$ are each independently a suitable oxygen protecting group;

is prepared by a process comprising steps of:

(a) reacting a saccharide having the structure:

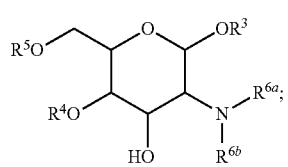

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and $R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;

with a suitable decanyl derivative to effect formation of a decanyl ether having the structure:

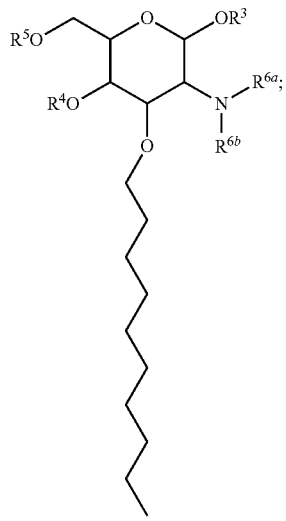

(b) deprotecting the amide moiety of the decanyl ether intermediate formed in step (a) under suitable conditions to effect formation of an amine having the structure:

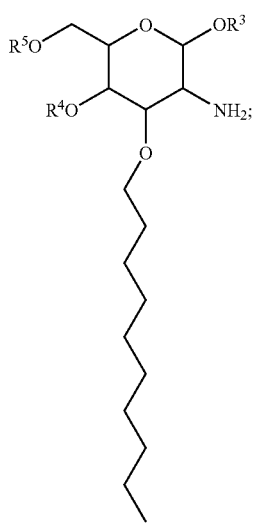

(c) reacting the amine intermediate formed in step (b) with a suitable 3-Oxo-tetradecanoic acid derivative under suitable conditions to effect formation of an amide intermediate having the structure:

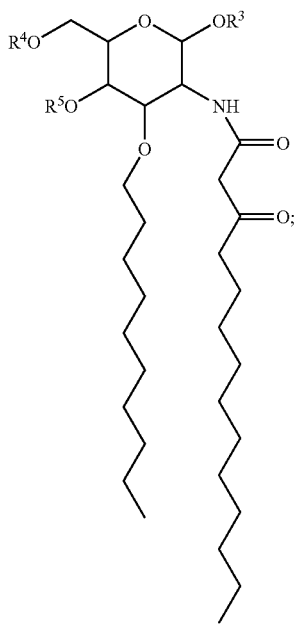

(d) deprotecting the intermediate formed in step (c) under suitable conditions to effect formation of a partially deprotected amide intermediate having the structure:

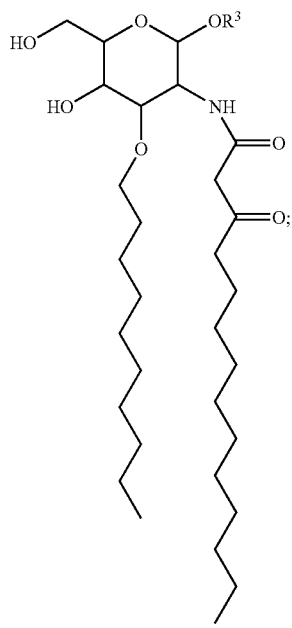

(e) selectively protecting the amide intermediate formed in step (d) under suitable conditions to effect formation of a protected intermediate having the structure:

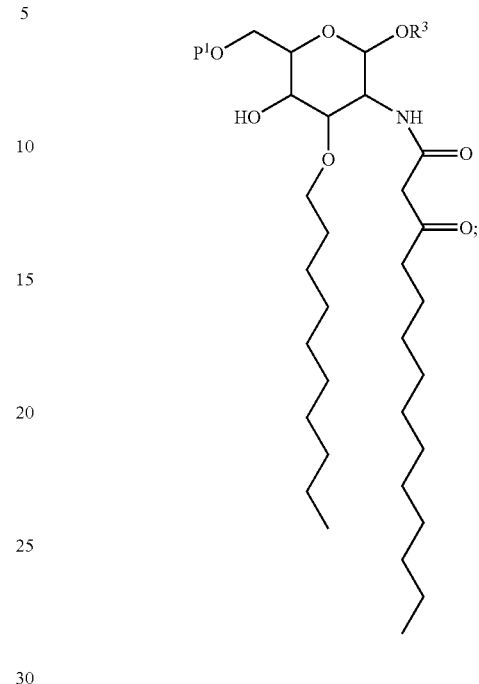

wherein $P^1$ is a suitable oxygen protecting group;

(f) reacting the protected intermediate formed in step (e) with a suitable reagent under suitable conditions to effect formation of a carbonic acid allyl ester intermediate having the structure:

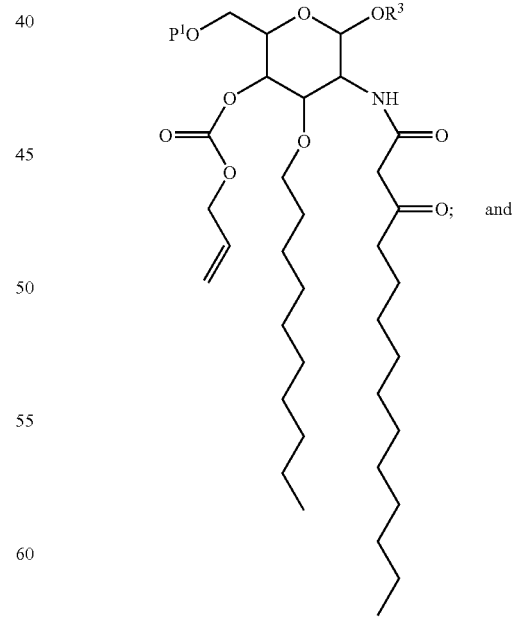
and (g) deprotecting the intermediate formed in step (f) under suitable conditions to effect formation of the saccharide having the structure:

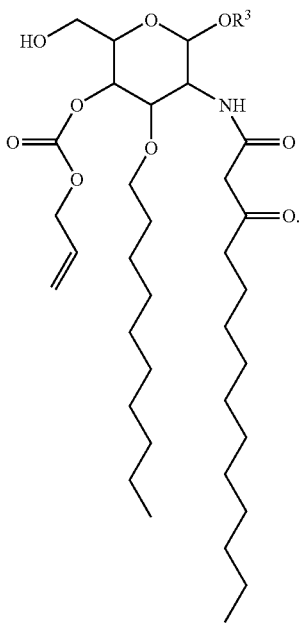

In certain embodiments, $R^3$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ is a substituted or unsubstituted lower alkenyl moiety. In certain exemplary embodiments, $R^3$ is a moiety having the structure:

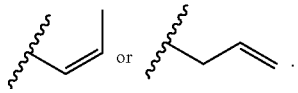

In certain embodiments, $R^4$ and $R^5$ are each independently alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, or $R^4$ and $R^5$, taken together, form a substituted or unsubstituted 5- or 6-membered heterocyclic ring; wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, $R^4$ and $R^5$, taken together, form a substituted or unsubstituted 5- or 6-membered heterocyclic ring. In certain exemplary embodiments, $R^4$ and $R^5$, taken together, form a substituted or unsubstituted 1,3-dioxane moiety. In certain exemplary embodiments, $R^4$ and $R^5$, taken together, form a 2,2-dimethyl-1,3-dioxane moiety.

In certain embodiments, $R^{6a}$ and $R^{6b}$ are each independently hydrogen, alkyl, alkenyl, —C(=O)$R^x$, —C(=O)O$R^x$, —S$R^x$, SO$_2R^x$, or $R^{6a}$ and $R^{6b}$, taken together form a moiety having the structure =C$R^xR^y$, wherein $R^{6a}$ and $R^{6b}$ are not simultaneously hydrogen and $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^{6a}$ is hydrogen and $R^{6b}$ is —C(=O)$R^x$, wherein $R^x$ is substituted or unsubstituted lower alkyl. In certain other exemplary embodiments, $R^{6a}$ is hydrogen and $R^{6b}$ is —C(=O)CX$_3$, wherein X represents a halogen atom. In certain other exemplary embodiments, $R^{6a}$ is hydrogen and $R^{6b}$ is —C(=O)CF$_3$.

In yet other embodiments, the decanyl derivative used in step (a) is a moiety having the structure CH$_3$(CH$_2$)$_9$SO$_2R^x$, wherein $R^x$ is alkyl or aryl. In certain exemplary embodiments, $R^x$ is methyl and the decanyl derivative is decanyl mesylate. In certain other exemplary embodiments, the decanyl derivative is decanyl mesylate and the step of reacting the saccharide in step (a) comprises reacting the saccharide with NaH in a suitable solvent. In certain exemplary embodiments, the solvent is THF/NMP.

In still other embodiments, $R^{6a}$ is hydrogen, $R^{6b}$ is —C(=O)CF$_3$ and the step of deprotecting the amide moiety of the decanyl ether in step (b) comprises deprotecting the amide moiety in the presence of tBuOK in a suitable solvent, followed by treatment with KOH. In certain embodiments, the solvent is DMSO.

In certain other embodiments, 3-Oxo-tetradecanoic acid derivative in step (c) is 3-Oxo-tetradecanoic acid itself and the reaction conditions comprise reacting the amine intermediate with 3-Oxo-tetradecanoic acid in the presence of EDC in NMP.

In yet other embodiments, the step of deprotecting the intermediate in step (d) comprises subjecting the intermediate to acidic conditions. In certain exemplary embodiments, the step of deprotecting the intermediate in step (d) comprises reacting the decanyl derivative with AcOH in H$_2$O.

In yet other embodiments, $P^1$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $P^1$ is a silyl protecting group. In certain exemplary embodiments, $P^1$ is a trialkylsilyl protecting group. In certain exemplary embodiments, $P^1$ is tert-Butyldimethylsilyl (TBDMS) and the step of selectively protecting the amide intermediate in step (e) comprises reacting the amide intermediate formed in step (d) with tert-Butyldimethylsilyl chloride (TBDMSCl) in the presence of a base in a suitable solvent. In certain exemplary embodiments, the base is imidazole and the solvent is DMF.

In certain other embodiments, $P^1$ is tert-Butyldimethylsilyl (TBDMS) and the step of deprotecting the intermediate formed in step (f) comprises reacting the saccharide having the structure:

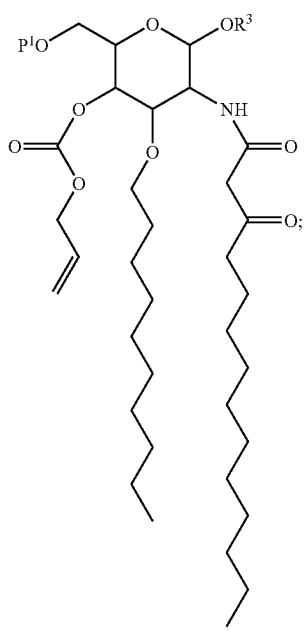

with HOAc in a suitable solvent system. In certain exemplary embodiments, the solvent system is iPrOH/H$_2$O. In certain other embodiments, $P^1$ is tert-Butyldimethylsilyl (TBDMS) and the step of deprotecting the intermediate formed in step (f) comprises reacting the protected saccharide with HF in a suitable solvent. In certain exemplary embodiments, the solvent is methylene chloride. In certain other embodiments, $P^1$ is tert-Butyldimethylsilyl (TBDMS) and the step of deprotecting the intermediate formed in step (f) comprises reacting the protected saccharide with a tetraalkylammonium reagent under fluoride catalysis. In certain exemplary embodiments, the tetraalkylammonium reagent is tetra-N-butyl ammonium fluoride (TBAF).

In still other embodiments, the reagent used in step (f) to effect formation of a carbonic acid allyl ester intermediate comprises a combination of triphosgene and allyl alcohol. In certain exemplary embodiments, the step of reacting the protected intermediate formed in step (e) to form the carbonic acid allyl ester intermediate comprises (i) reacting the protected intermediate with triphosgene in the presence of a base in a suitable solvent, and (ii) trapping the phosgene adduct formed in situ with allyl alcohol under suitable conditions. In certain exemplary embodiments, the base is pyridine and the solvent is toluene.

In certain embodiments, the invention provides a method for preparing B1287 and the method comprises steps of:

(a) effecting glycosylation of a monosaccharide having the structure:

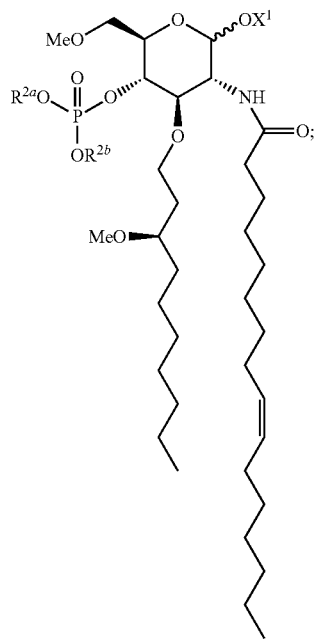

wherein $OX^1$ represents a suitable leaving group for effecting the glycosylation; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

with a monosaccharide having the structure:

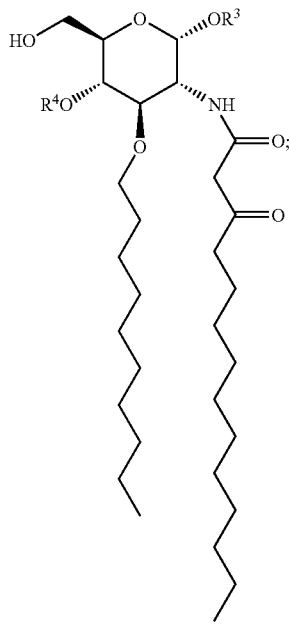

wherein $R^3$ and $R^4$ are each independently a suitable oxygen protecting group;

under suitable conditions to effect formation of a disaccharide having the structure:

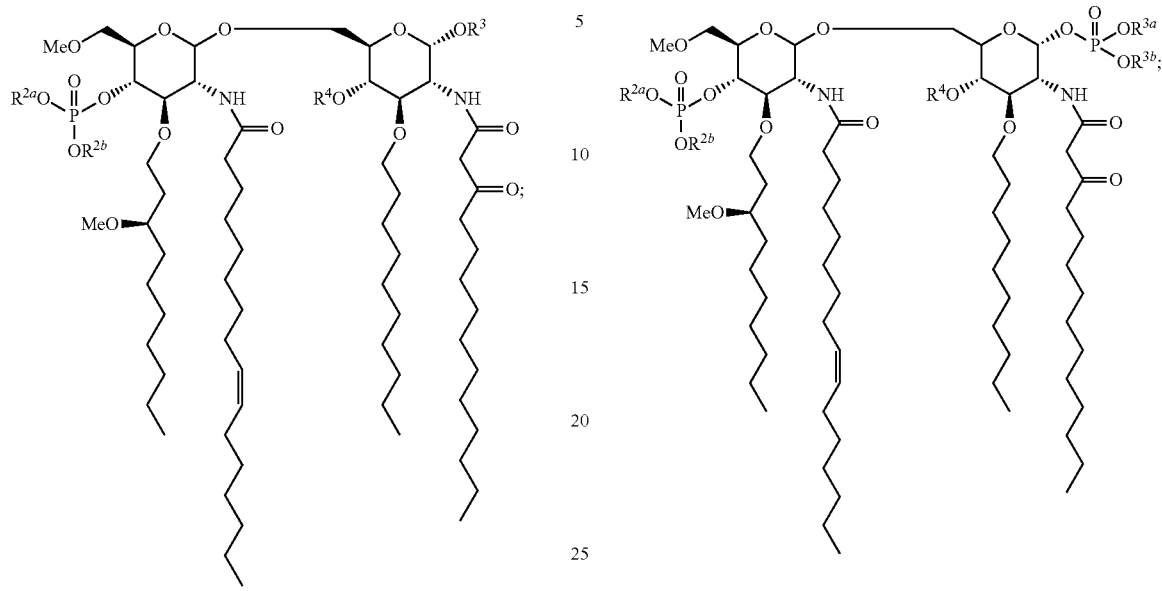

(b) deprotecting the disaccharide formed in step (a) under suitable conditions to effect formation of a partially deprotected disaccharide having the structure:

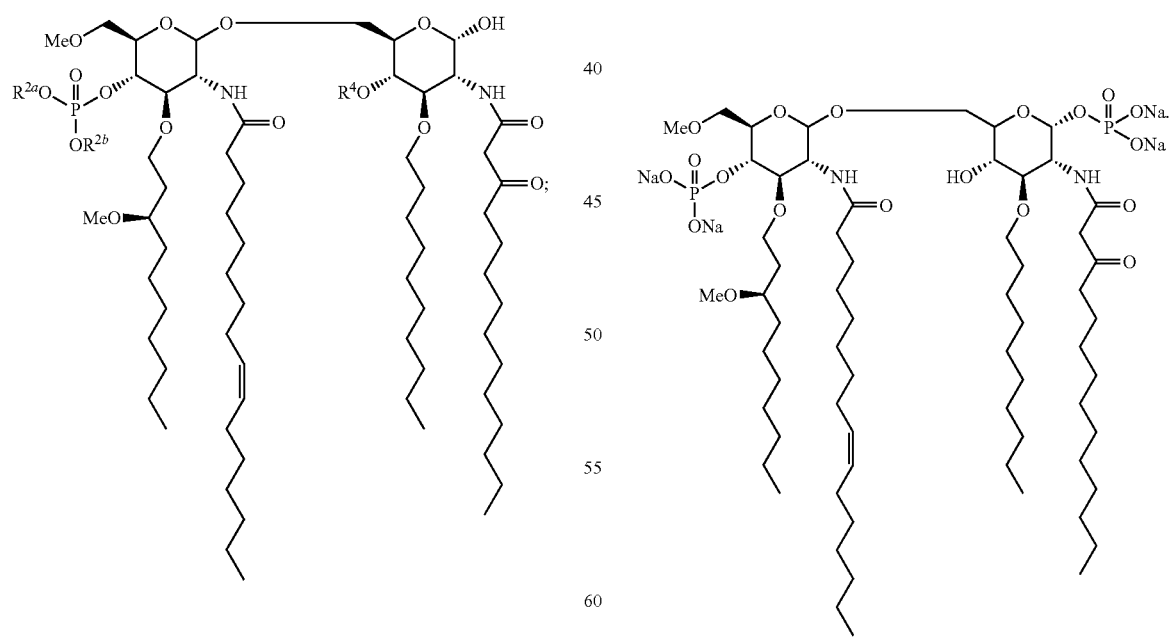

(c) reacting the partially deprotected disaccharide formed in step (b) with a suitable reagent under suitable conditions to effect formation of a diphosphorylated disaccharide having the structure:

wherein $R^{3a}$ and $R^{3b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (e) treating the diphosphorylated disaccharide formed in step (c) with one or more suitable reagents under suitable conditions to effect formation of a disaccharide having the structure:

In yet other embodiments, the step of treating the diphosphorylated disaccharide formed in step (c) with one or more suitable reagents under suitable conditions leads to the formation of a compound having the structure:

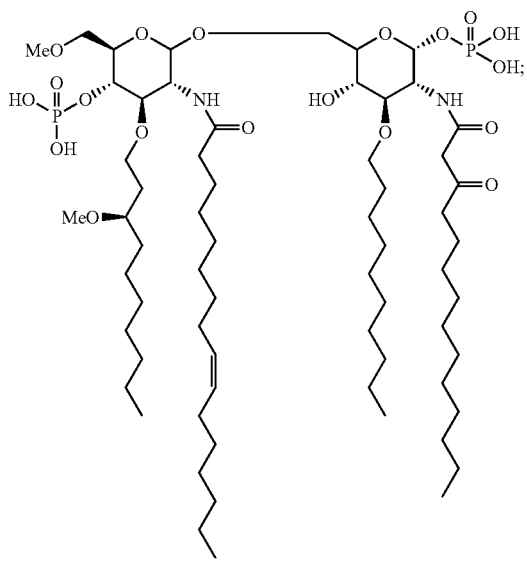

which is then purified to yield the corresponding tetrasodium salt:

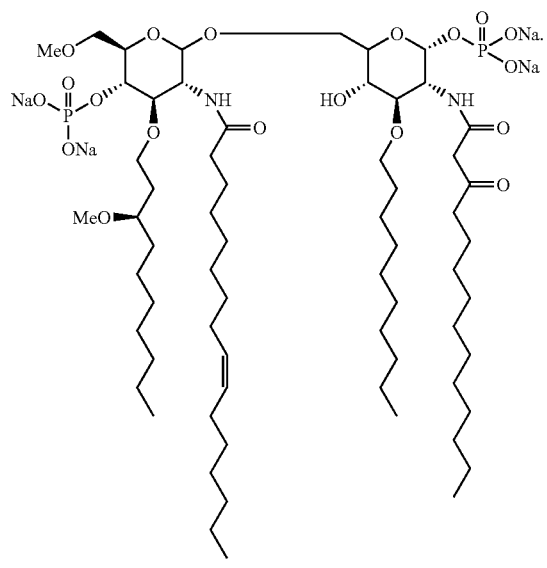

In certain embodiments, $X^1$ is alkyl, alkenyl, alkynyl, heteroalkyl, heteroalkenyl, heteroalkynyl, aryl, heteroaryl, silyl, —C(=O)$R^{X1A}$, —C(=S)$R^{X1A}$, —C(=N$R^{X1A}$)$R^{X1B}$, —SO$_2$$R^{X1A}$, wherein $R^{X1A}$ and $R^{X1B}$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $X^1$ is —C(=N$R^{X1A}$)$R^{X1B}$ or —SO$_2$$R^{X1A}$, wherein $R^{X1A}$ and $R^{X1B}$ are each independently hydrogen or an aliphatic, alicyclic, heteroaliphatic, heteroalicyclic, aryl or heteroaryl moiety. In certain exemplary embodiments, $X^1$ is —C(=N$R^{X1A}$)$R^{X1B}$ wherein $R^{X1A}$ and $R^{X1B}$ are each independently hydrogen or substituted or unsubstituted lower alkyl. In certain exemplary embodiments, $R^{X1A}$ is hydrogen and $R^{X1B}$ is substituted or unsubstituted lower alkyl. In certain exemplary embodiments, $R^{X1A}$ is hydrogen and $R^{X1B}$ is —CX$_3$, wherein X represents a halogen atom. In certain exemplary embodiments, $R^{X1A}$ is hydrogen, $R^{X1B}$ is —CCl$_3$, and $X^1$ is —C(=NH)CCl$_3$. In certain exemplary embodiments, $X^1$ is —C(=NH)CCl$_3$ and the glycosylation step (a) is conducted under strongly acidic conditions. In certain exemplary embodiments, the glycosylation conditions comprise an organic sulfonic acid and a suitable solvent. In certain embodiments, the organic sulfonic acid is an alkanesulfonic acid. In certain embodiments, the alkyl sulfonic acid is MeSO$_3$H or EtSO$_3$H. In certain embodiments, the solvent is an apolar solvent. In certain exemplary embodiments, the apolar solvent is toluene, hexane or combination thereof. In certain embodiments, the glycosylation conditions comprise zinc triflate (Zn(OTf)$_2$) and a suitable solvent. The certain exemplary embodiments, the glycosylation conditions comprise zinc triflate (Zn(OTf)$_2$) and methylene chloride. In yet other embodiments, the glycosylation conditions comprise silver triflate (AgOTf) and a suitable solvent. In still other embodiments, the glycosylation conditions comprise silver triflate (AgOTf) and methylene chloride. In certain embodiment, in the glycosylation step (a), the monosaccharide having the structure:

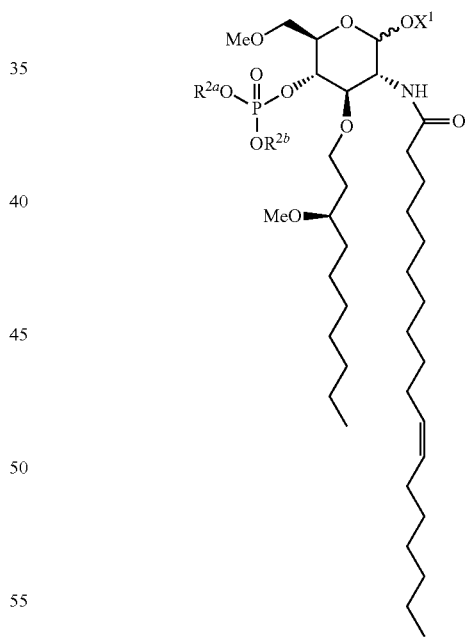

is used in excess. In certain embodiments, between 1.1 to about 3.0 equivalents of the monosaccharide described directly above are used. In certain other embodiments, between 1.2 to about 2.9 equivalents are used. In certain other embodiments, between 1.3 to about 2.8 equivalents are used. In certain other embodiments, between 1.5 to about 2.5 equivalents are used. In certain other embodiments, between 1.6 to about 2.3 equivalents are used. In certain exemplary embodiments, between 1.8 to about 2.0 equivalents are used.

In certain embodiments, R³ is alkyl, alkenyl, alkynyl, heteroalkyl, heteroalkenyl, heteroalkynyl, aryl, heteroaryl, silyl, —C(=O)Rˣ, —C(=S)Rˣ, —C(=NRˣ)Rʸ, —SO₂Rˣ, wherein Rˣ and Rʸ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R^A or —ZR^A, wherein Z is —O—, —S—, —NR^B, wherein each occurrence of R^A and R^B is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, R³ is a substituted or unsubstituted lower alkenyl moiety. In certain exmplary embodiments, R³ is a moiety having the structure:

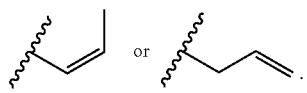

In certain embodiments, the reaction conditions used in deprotection step (b) comprise a strong acid in a suitable solvent. In certain exemplary embodiments, the strong acid is HF and the solvent is acetonitrile.

In certain exemplary embodiments, R³ is a moiety having the structure:

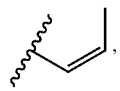

and the reaction conditions of deprotection step (b) comprise a strong acid in a suitable solvent. In certain exemplary embodiments, the strong acid is HF and the solvent is acetonitrile.

In certain other embodiments, the reagent in step (c) is a phosphorylating agent. In certain embodiments, the reaction conditions in step (c) comprise bis(allyloxy)diisopropyl aminophosphine and an oxidizing agent. In certain exemplary embodiments, the oxidizing agent is Oxone.

In certain embodiments, R^{2a}, R^{2b}, R^{3a} and R^{3b} are each independently a substituted or unsubstituted alkenyl moiety. In certain exemplary embodiments, R^{2a}, R^{2b}, R^{3a} and R^{3b} are each allyl.

In yet other embodiments, R⁴ is alkyl, alkenyl, alkynyl, heteroalkyl, heteroalkenyl, heteroalkynyl, aryl, heteroaryl, silyl, —C(=O)Rˣ, —C(=S)Rˣ, —C(=NRˣ)Rʸ, —SO₂Rˣ, wherein Rˣ and Rʸ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R^A or —ZR^A, wherein Z is —O—, —S—, —NR^B, wherein each occurrence of R^A and R^B is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, R⁴ is —C(=O)OR^A, wherein R^A is substituted or unsubstituted alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl. In certain exemplary embodiments, R⁴ is —C(=O)ORˣ, wherein Rˣ is substituted or unsubstituted alkyl, alkenyl. In certain exemplary embodiments, Rˣ is allyl, and R⁴ is —C(=O)OCH₂CH=CH₂.

In certain other embodiments, R^{2a}, R^{2b}, R^{3a} and R^{3b} are each allyl, R⁴ is —C(=O)OCH₂CH=CH₂ and the deprotection conditions in step (d) comprise Pd(PPH₃) in a suitable solvent. In certain exemplary embodiments, the treating conditions in step (d) further comprise triphenyl phosphine and acetic acid.

In still other embodiments, purification of the compound having the structure:

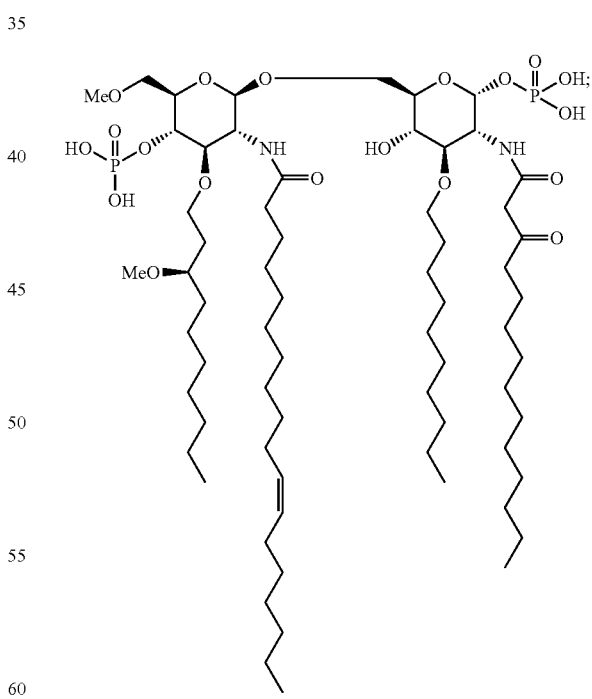

comprises chromatographic separation and treatment with a base. In certain exemplary embodiments, the purification process comprises (i) ion exchange chromatography, (ii) POROS 50 R2, methanol, and (iii) treatment with aqueous NaOH.

In certain exemplary embodiments, the saccharide having the structure:

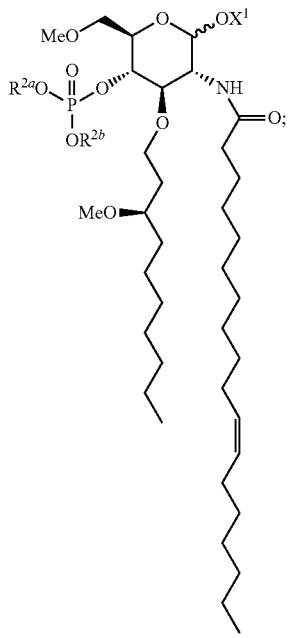

wherein $OX^1$ represents a suitable leaving group for effecting a glycosylation reaction; and $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl;

is prepared by a process comprising steps of:

(a) reacting an amine having the structure:

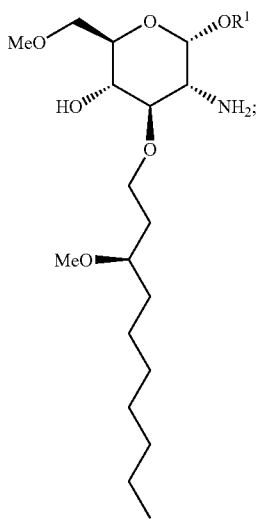

wherein $R^1$ is a suitable oxygen protecting group;

with a suitable vaccenoyl acid derivative to effect formation of an amide intermediate having the structure:

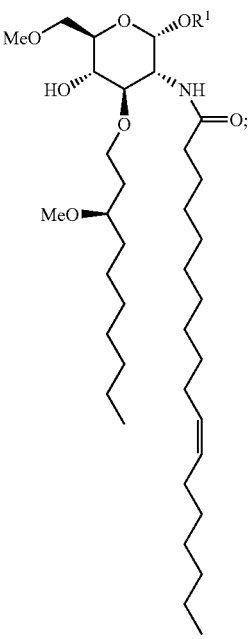

(b) reacting the amide intermediate formed in step (a) with a suitable reagent to effect formation of a phosphorylated saccharide having the structure:

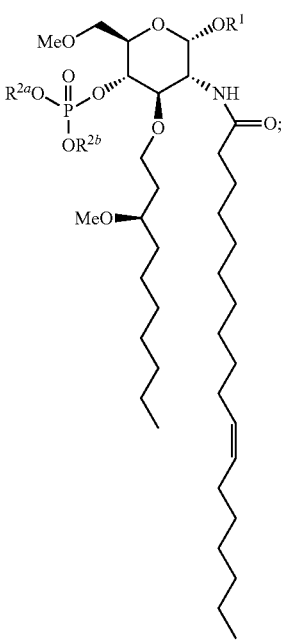

wherein $R^{2a}$ and $R^{2b}$ are each independently alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, aryl or heteroaryl; and (c) deprotecting the phosphorylated saccharide formed in step (b) under suitable conditions to effect formation of an alcohol intermediate having the structure:

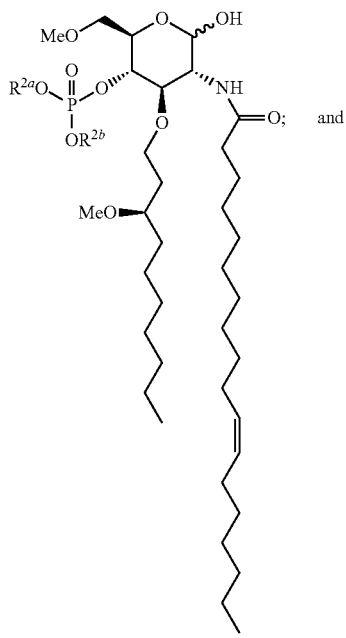

(d) reacting the alcohol intermediate formed in step (c) under suitable conditions to effect formation of a saccharide having the structure:

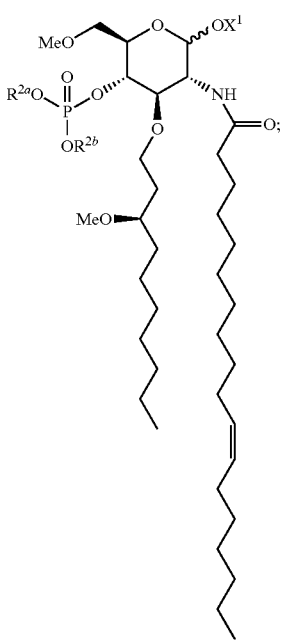

wherein $OX^1$ represents a suitable leaving group for effecting a glycosylation reaction.

In certain embodiments, $R^1$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2$R, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^1$ is a substituted or unsubstituted lower alkenyl moiety. In certain exemplary embodiments, $R^1$ is a moiety having the structure:

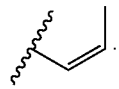

In certain embodiments, the vaccenoyl acid derivative of step (a) is a vaccenoyl chloride. In certain exemplary embodiments, the vaccenoyl acid derivative of step (a) is Δ-11-cis-vaccenoyl chloride. In certain other exemplary embodiments, the vaccenoyl acid derivative of step (a) is a vaccenoyl chloride and the reaction conditions for reacting the amine with the vaccenoyl acid derivative in step (a) comprise a weak base. In certain other exemplary embodiments, the vaccenoyl acid derivative of step (a) is Δ-11-cis-vaccenoyl chloride and the reaction conditions for reacting the amine with the vaccenoyl acid derivative in step (a) comprise a weak base. In certain exemplary embodiments, the vaccenoyl acid derivative of step (a) is Δ-11-cis-vaccenoyl chloride. In certain exemplary embodiments, the weak base is aqueous NaHCO$_3$. In certain other exemplary embodiments, the weak base is aqueous K$_2$CO$_3$.

In certain other embodiments, the reagent in step (b) is a phosphorylating agent. In certain exemplary embodiments, the reaction conditions in step (b) comprise bis(allyloxy)diisopropyl aminophosphine and an oxidizing agent. In certain exemplary embodiments, the oxidizing agent is Oxone. In certain other exemplary embodiments, the reaction conditions in step (b) further comprise tetrazole. In certain other exemplary embodiments, the reaction conditions in step (b) comprise bis(allyloxy)diisopropyl aminophosphine (DPP), pyridinium trifluoroacetate and an oxidizing agent. In certain exemplary embodiments, the oxidizing agent is hydrogen peroxide.

In certain embodiments, $R^{3a}$, $R^{3b}$, $R^{3a}$ and $R^{3b}$ are each independently a substituted or unsubstituted alkenyl moiety. In certain exemplary embodiments, $R^{3a}$, $R^{3b}$, $R^{3a}$ and $R^{3b}$ are each allyl.

In yet other embodiments, $R^1$ is a moiety having the structure:

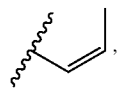

and the deprotection reaction in step (c) comprise strongly acidic conditions. In certain exemplary embodiments, the deprotection conditions in step (c) comprise HCl in a suitable solvent. In certain exemplary embodiments, the solvent is THF or acetonitrile.

In certain exemplary embodiments, $X^1$ is —C(=NH)$R^{X1B}$ wherein $R^{X1B}$ is substituted or unsubstituted lower alkyl, and the step of reacting the alcohol intermediate in step (d) comprises reacting the alcohol intermediate with a moiety having the structure R$^{X1B}$CN in the presence of a weak base. In certain exemplary embodiments, X$^1$ is —C(═NH)CX$_3$ wherein X represents a halogen atom and the weak base is K$_2$CO$_3$. In certain exemplary embodiments, X$^1$ is —C(═NH)CCl$_3$.

In yet other embodiments, the saccharide having the structure:

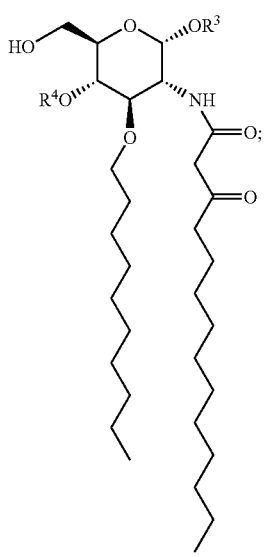

wherein R$^3$ and R$^4$ are each independently a suitable oxygen protecting group;
is prepared by a process comprising steps of:
(a) reacting a saccharide having the structure:

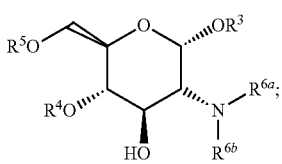

wherein R$^3$, R$^4$ and R$^5$ are each independently a suitable oxygen protecting group; wherein R$^4$ and R$^5$, taken together, may form a substituted or unsubstituted 5- or 6-membered heterocyclic ring; and
R$^{6a}$ and R$^{6b}$ are each independently hydrogen or a suitable nitrogen protecting group, or R$^{6a}$ and R$^{6b}$, taken together, form a 5- or 6-membered heterocyclic ring; wherein R$^{6a}$ and R$^{6b}$ are not simultaneously hydrogen;

with a suitable decanyl derivative to effect formation of a decanyl ether having the structure:

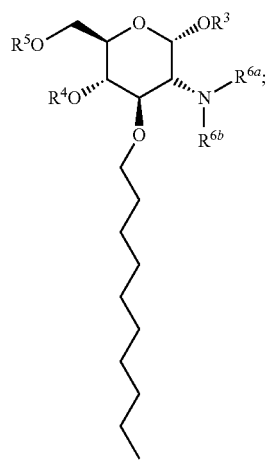

(b) deprotecting the decanyl ether formed in step (a) under suitable conditions to effect formation of a partially deprotected intermediate having the structure:

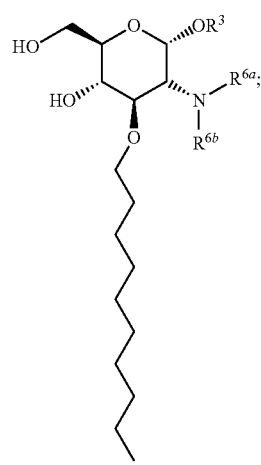

(c) deprotecting the amide moiety of the intermediate formed in step (b) under suitable conditions to give an amine intermediate having the structure:

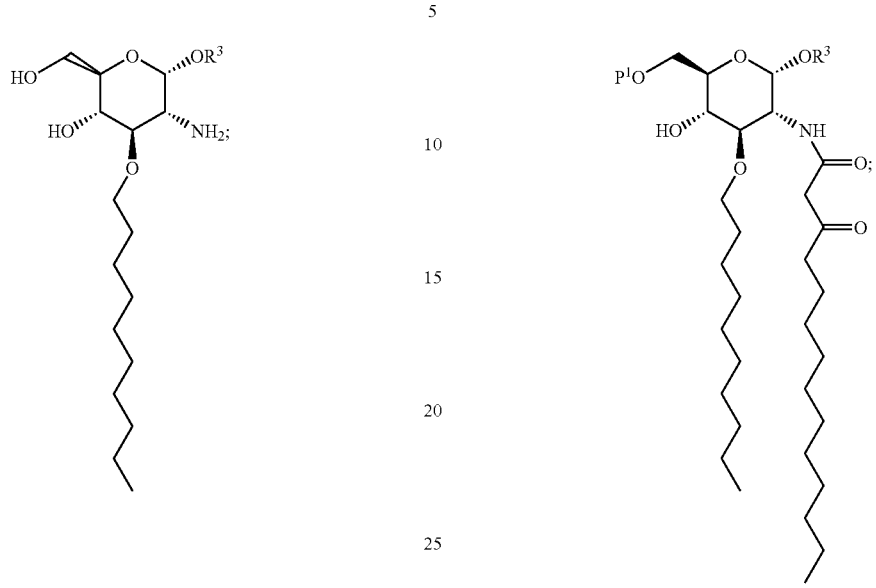

(d) reacting the amine intermediate formed in step (c) with a suitable 3-Oxo-tetradecanoic acid derivative under suitable conditions to effect formation of an amide intermediate having the structure:

(e) selectively protecting the amide intermediate formed in step (d) under suitable conditions to effect formation of a protected intermediate having the structure:

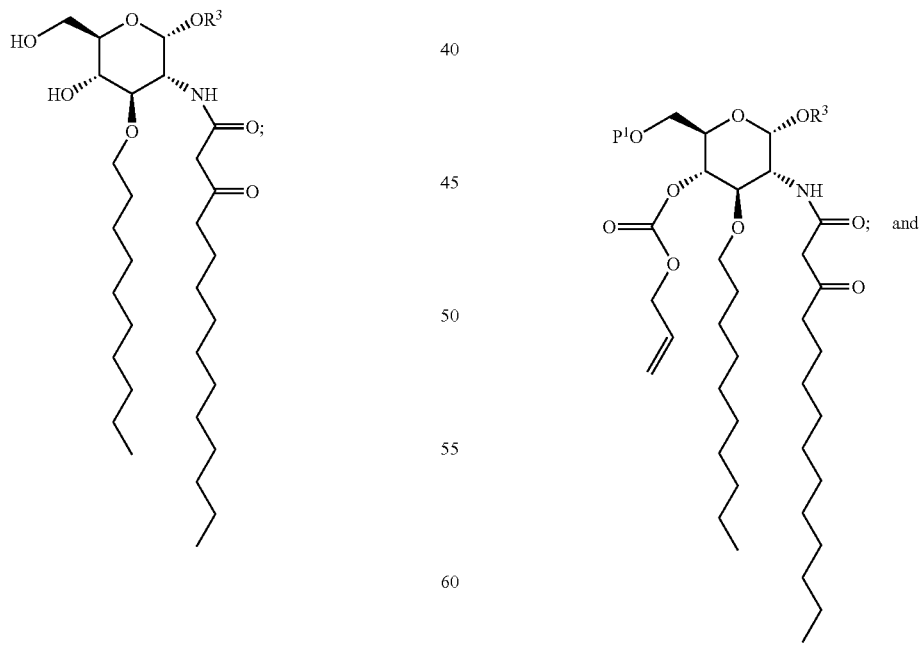

wherein $P^1$ is a suitable oxygen protecting group;

(f) reacting the protected intermediate formed in step (e) with a suitable reagent under suitable conditions to effect formation of a carbonic acid allyl ester intermediate having the structure:

(g) deprotecting the intermediate formed in step (f) under suitable conditions to effect formation of the saccharide having the structure:

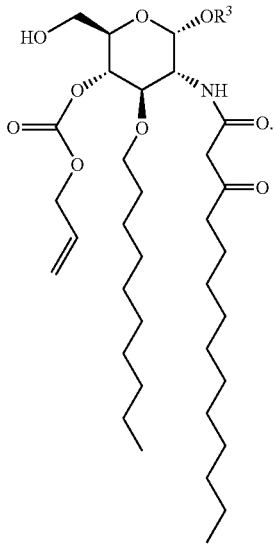

In certain embodiments, $R^3$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2$$R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ is a substituted or unsubstituted lower alkenyl moiety. In certain exemplary embodiments, $R^3$ is a moiety having the structure:

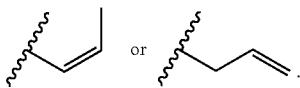

In certain embodiments, $R^4$ and $R^5$ are each independently alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2$$R^x$, or $R^4$ and $R^5$, taken together, form a substituted or unsubstituted 5- or 6-membered heterocyclic ring; wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, $R^4$ and $R^5$, taken together, form a substituted or unsubstituted 5- or 6-membered heterocyclic ring. In certain exemplary embodiments, $R^4$ and $R^5$, taken together, form a substituted or unsubstituted 1,3-dioxane moiety. In certain exemplary embodiments, $R^4$ and $R^5$, taken together, form a 2,2-dimethyl-1,3-dioxane moiety.

In certain embodiments, $R^{6a}$ and $R^{6b}$ are each independently hydrogen, alkyl, alkenyl, —C(=O)$R^x$, —C(=O)O$R^x$, —S$R^x$, SO$_2$$R^x$, or $R^{6a}$ and $R^{6b}$, taken together form a moiety having the structure =C$R^x$$R^y$, wherein $R^{6a}$ and $R^{6b}$ are not simultaneously hydrogen and $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^{6a}$ is hydrogen and $R^{6b}$ is —C(=O)$R^x$, wherein $R^x$ is substituted or unsubstituted lower alkyl. In certain other exemplary embodiments, $R^{6a}$ is hydrogen and $R^{6b}$ is —C(=O)C$X_3$, wherein X represents a halogen atom. In certain other exemplary embodiments, $R^{6a}$ is hydrogen and $R^{6b}$ is —C(=O)C$F_3$.

In yet other embodiments, the decanyl derivative used in step (a) is a moiety having the structure $CH_3(CH_2)_9SO_2R^x$, wherein $R^x$ is alkyl or aryl. In certain exemplary embodiments, $R^x$ is methyl and the decanyl derivative is decanyl mesylate. In certain other exemplary embodiments, the decanyl derivative is decanyl mesylate and the step of reacting the saccharide in step (a) comprises reacting the saccharide with NaH in a suitable solvent. In certain exemplary embodiments, the solvent is THF/NMP.

In yet other embodiments, the step of deprotecting the decanyl derivative in step (b) comprises subjecting the decanyl derivative to acidic conditions. In certain exemplary embodiments, the step of deprotecting the decanyl derivative in step (b) comprises reacting the decanyl derivative with AcOH in $H_2O$.

In still other embodiments, $R^{6a}$ is hydrogen, $R^{6b}$ is —C(=O)C$F_3$ and the step of deprotecting the amide moiety in step (c) comprises deprotecting the amide moiety in the presence of tBuOK in a suitable solvent, followed by treatment with KOH. In certain embodiments, the solvent is DMSO.

In certain other embodiments, 3-Oxo-tetradecanoic acid derivative in step (d) is 3-Oxo-tetradecanoic acid itself and the reaction conditions comprise reacting the amine intermediate with 3-Oxo-tetradecanoic acid in the presence of EDC in NMP.

In yet other embodiments, $P^1$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2$$R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $P^1$ is a silyl protecting group. In certain exemplary embodiments, $P^1$ is a trialkylsilyl protecting group. In certain exemplary embodiments, $P^1$ is tert-Butyldimethylsilyl (TBDMS) and the step of selectively protecting the amide intermediate in step (e) comprises reacting the amide intermediate formed in step (d) with tert-Butyldimethylsilyl chloride (TBDMSCl) in the presence of a base in a suitable solvent. In certain exemplary embodiments, the base is imidazole and the solvent is DMF.

In certain other embodiments, $P^1$ is tert-Butyldimethylsilyl (TBDMS) and the step of deprotecting the intermediate formed in step (f) comprises reacting the saccharide having the structure:

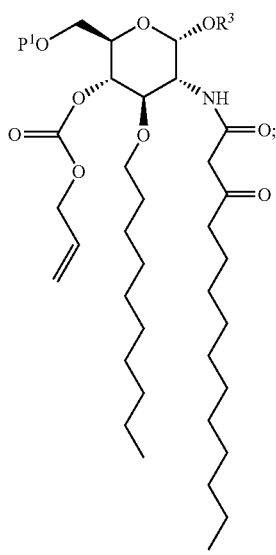

with HOAc in a suitable solvent system. In certain exemplary embodiments, the solvent system is iPrOH/H$_2$O. In certain other embodiments, $P^1$ is tert-Butyldimethylsilyl (TBDMS) and the step of deprotecting the intermediate formed in step (f) comprises reacting the protected saccharide with HF in a suitable solvent In certain exemplary embodiments, the solvent is methylene chloride. In certain other embodiments, $P^1$ is tert-Butyldimethylsilyl (TBDMS) and the step of deprotecting the intermediate formed in step (f) comprises reacting the protected saccharide with a tetraalkylammonium reagent under fluoride catalysis. In certain exemplary embodiments, the tetraalkylammonium reagent is tetra-N-butyl ammonium fluoride (TBAF).

In still other embodiments, the reagent used in step (f) to effect formation of a carbonic acid allyl ester intermediate comprises a combination of triphosgene and allyl alcohol. In certain exemplary embodiments, the step of reacting the protected intermediate formed in step (e) to form the carbonic acid allyl ester intermediate comprises (i) reacting the protected intermediate with triphosgene in the presence of a base in a suitable solvent, and (ii) trapping the phosgene adduct formed in situ with allyl alcohol under suitable conditions. In certain exemplary embodiments, the base is pyridine and the solvent is toluene.

In certain other exemplary embodiments, the saccharide having the structure:

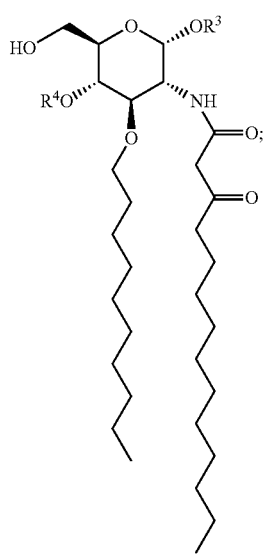

wherein $R^3$ and $R^4$ are each independently a suitable oxygen protecting group;
is prepared by a process comprising steps of:
(a) reacting a saccharide having the structure:

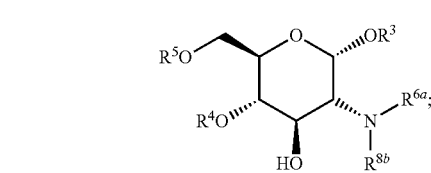

wherein $R^3$, $R^4$ and $R^5$ are each independently a suitable oxygen protecting group; wherein $R^4$ and $R^5$, taken together, may form a substituted or unsubstituted 5- or 6-membered heterocyclic ring; and
$R^{6a}$ and $R^{6b}$ are each independently hydrogen or a suitable nitrogen protecting group, or $R^{6a}$ and $R^{6b}$, taken together, form a 5- or 6-membered heterocyclic ring; wherein $R^{6a}$ and $R^{6b}$ are not simultaneously hydrogen;
with a suitable decanyl derivative to effect formation of a decanyl ether having the structure:

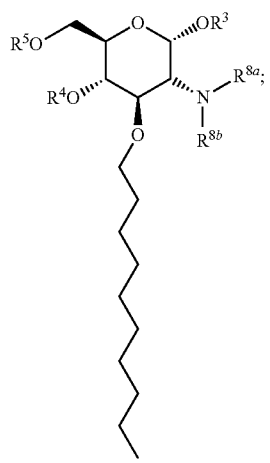

(b) deprotecting the amide moiety of the decanyl ether intermediate formed in step (a) under suitable conditions to effect formation of an amine having the structure:

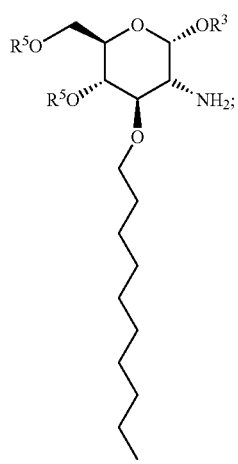

(c) reacting the amine intermediate formed in step (b) with a suitable 3-Oxo-tetradecanoic acid derivative under suitable conditions to effect formation of an amide intermediate having the structure:

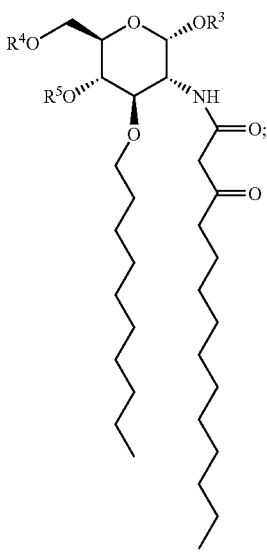

(d) deprotecting the intermediate formed in step (c) under suitable conditions to effect formation of a partially deprotected amide intermediate having the structure:

(e) selectively protecting the amide intermediate formed in step (d) under suitable conditions to effect formation of a protected intermediate having the structure:

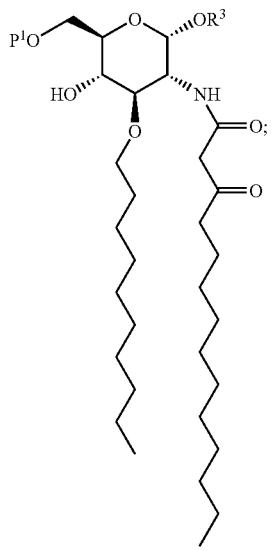

wherein P¹ is a suitable oxygen protecting group;

(f) reacting the protected intermediate formed in step (e) with a suitable reagent under suitable conditions to effect formation of a carbonic acid allyl ester intermediate having the structure:

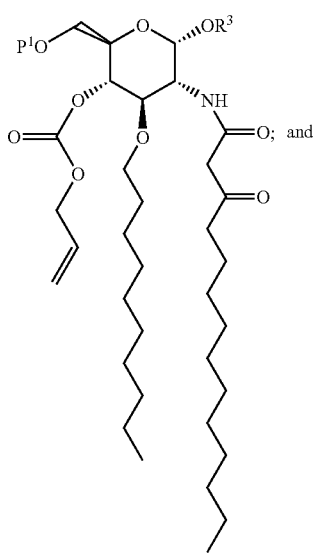

(g) deprotecting the intermediate formed in step (f) under suitable conditions to effect formation of the saccharide having the structure:

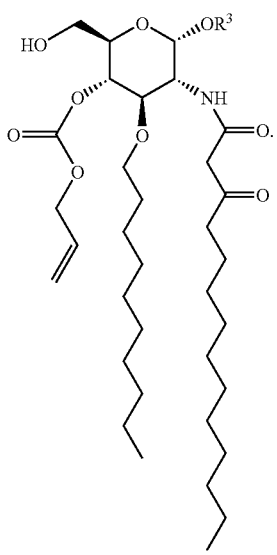

In certain embodiments, $R^3$ is alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^3$ is a substituted or unsubstituted lower alkenyl moiety. In certain exemplary embodiments, $R^3$ is a moiety having the structure:

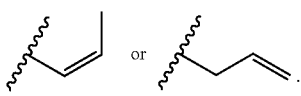

In certain embodiments, $R^4$ and $R^5$ are each independently alkyl, alkenyl, alkynyl, heteroalkyl, heteroalkenyl, heteroalkynyl, aryl, heteroaryl, silyl, —C(=O)$R^x$, —C(=S)$R^x$, —C(=N$R^x$)$R^y$, —SO$_2$$R^x$, or $R^4$ and $R^5$, taken together, form a substituted or unsubstituted 5- or 6-membered heterocyclic ring; wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain embodiments, $R^4$ and $R^5$, taken together, form a substituted or unsubstituted 5- or 6-membered heterocyclic ring. In certain exemplary embodiments, $R^4$ and $R^5$, taken together, form a substituted or unsubstituted 1,3-dioxane moiety. In certain exemplary embodiments, $R^4$ and $R^5$, taken together, form a 2,2-dimethyl-1,3-dioxane moiety.

In certain embodiments, $R^6$ and $R^{6b}$ are each independently hydrogen, alkyl, alkenyl, —C(=O)$R^x$, —C(=O)O$R^x$, —S$R^x$, SO$_2$$R^x$, or $R^{6a}$ and $R^{6b}$, taken together form a moiety having the structure =C$R^x$$R^y$, wherein $R^{6a}$ and $R^{6b}$ are not simultaneously hydrogen and $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $R^{6a}$ is hydrogen and $R^{6b}$ is —C(=O)$R^x$, wherein $R^x$ is substituted or unsubstituted lower alkyl. In certain other exemplary embodiments, $R^{6a}$ is hydrogen and $R^{6b}$ is —C(=O)C$X_3$, wherein X represents a halogen atom. In certain other exemplary embodiments, $R^{6a}$ is hydrogen and $R^{6b}$ is —C(=O)CF$_3$.

In yet other embodiments, the decanyl derivative used in step (a) is a moiety having the structure CH$_3$(CH$_2$)$_9$SO$_2$$R^x$, wherein $R^x$ is alkyl or aryl. In certain exemplary embodiments, $R^x$ is methyl and the decanyl derivative is decanyl mesylate. In certain other exemplary embodiments, the decanyl derivative is decanyl mesylate and the step of reacting the saccharide in step (a) comprises reacting the saccharide with NaH in a suitable solvent. In certain exemplary embodiments, the solvent is THF/NMP.

In still other embodiments, $R^{6a}$ is hydrogen, $R^{6b}$ is —C(=O)CF$_3$ and the step of deprotecting the amide moiety of the decanyl ether in step (b) comprises deprotecting the amide moiety in the presence of tBuOK in a suitable solvent, followed by treatment with KOH. In certain embodiments, the solvent is DMSO.

In certain other embodiments, 3-Oxo-tetradecanoic acid derivative in step (c) is 3-Oxo-tetradecanoic acid itself and the reaction conditions comprise reacting the amine intermediate with 3-Oxo-tetradecanoic acid in the presence of EDC in NMP.

In yet other embodiments, the step of deprotecting the intermediate in step (d) comprises subjecting the intermediate to acidic conditions. In certain exemplary embodiments, the step of deprotecting the intermediate in step (d) comprises reacting the decanyl derivative with AcOH in H$_2$O.

In yet other embodiments, $P^1$ is alkyl, alkenyl, alkynyl, heteroalkyl, heteroalkenyl, heteroalkynyl, aryl, heteroaryl; silyl, —C(=O)$R^x$, —C(=S)$R^x$, —C(=N$R^x$)$R^y$, —SO$_2$$R^x$, wherein $R^x$ and $R^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)$R^A$ or —Z$R^A$, wherein Z is —O—, —S—, —N$R^B$, wherein each occurrence of $R^A$ and $R^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety. In certain exemplary embodiments, $P^1$ is a silyl protecting group. In certain exemplary embodiments, $P^1$ is a trialkylsilyl protecting group. In certain exemplary embodiments, $P^1$ is tert-Butyldimethylsilyl (TBDMS) and the step of selectively protecting the amide intermediate in step (e) comprises reacting the amide intermediate formed in step (d) with tert-Butyldimethylsilyl chloride (TBDMSCl) in the presence of a base in a suitable solvent. In certain exemplary embodiments, the base is imidazole and the solvent is DMF.

In certain other embodiments, $P^1$ is tert-Butyldimethylsilyl (TBDMS) and the step of deprotecting the intermediate formed in step (f) comprises reacting the saccharide having the structure:

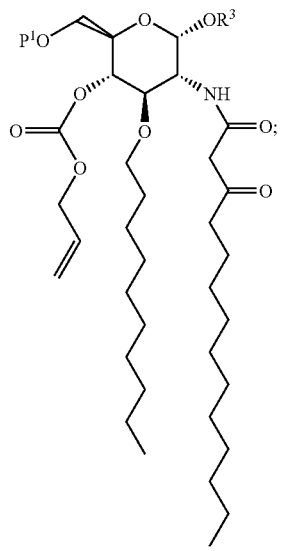

with HOAc in a suitable solvent system. In certain exemplary embodiments, the solvent system is iPrOH/H$_2$O. In certain other embodiments, $P^1$ is tert-Butyldimethylsilyl (TBDMS) and the step of deprotecting the intermediate formed in step (f) comprises reacting the protected saccharide with HF in a suitable solvent. In certain exemplary embodiments, the solvent is methylene chloride. In certain other embodiments, $P^1$ is tert-Butyldimethylsilyl (TBDMS) and the step of deprotecting the intermediate formed in step (f) comprises reacting the protected saccharide with a tetraalkylammonium reagent under fluoride catalysis. In certain exemplary embodiments, the tetraalkylammonium reagent is tetra-N-butyl ammonium fluoride (TBAF).

In still other embodiments, the reagent used in step (f) to effect formation of a carbonic acid allyl ester intermediate comprises a combination of triphosgene and allyl alcohol. In certain exemplary embodiments, the step of reacting the protected intermediate formed in step (e) to form the carbonic acid allyl ester intermediate comprises (i) reacting the protected intermediate with triphosgene in the presence of a base in a suitable solvent, and (ii) trapping the phosgene adduct formed in situ with allyl alcohol under suitable conditions. In certain exemplary embodiments, the base is pyridine and the solvent is toluene.

In another aspect, the invention provides intermediates useful for the preparation of B1287 and its stereoisomers. Preferred intermediates include, but are not limited to:

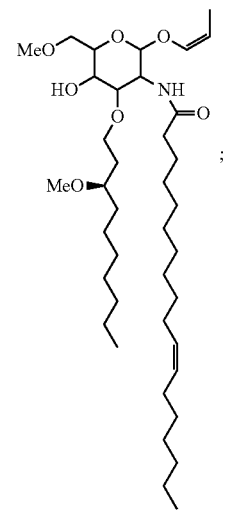

-continued

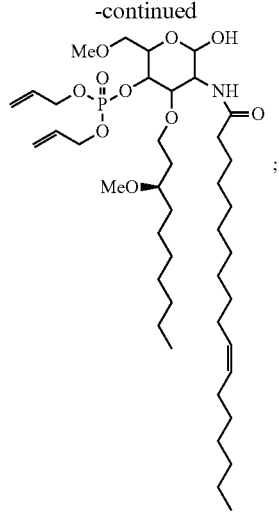

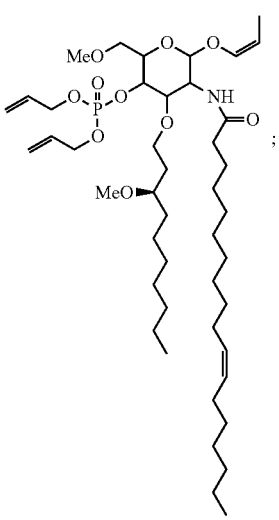

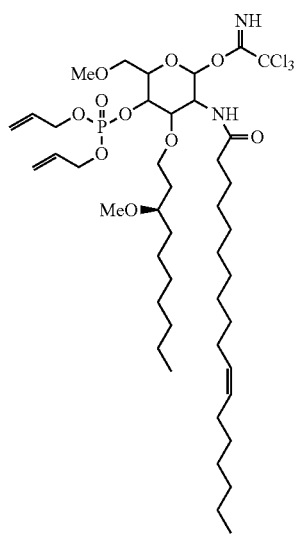

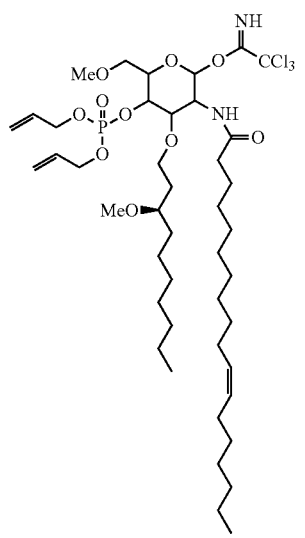

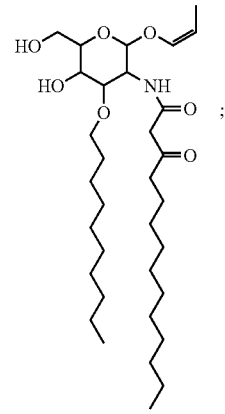
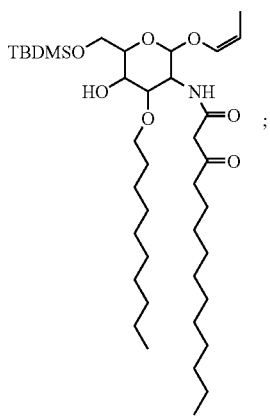
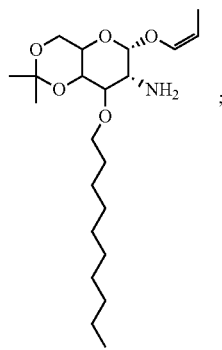
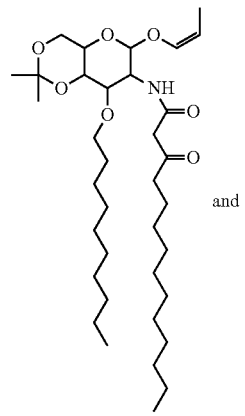
and
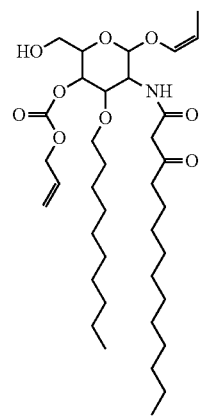
Particularly preferred intermediates include, but are not limited to:
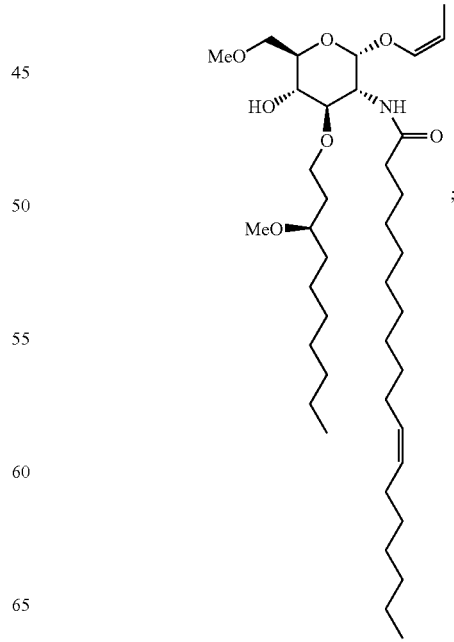

99
100
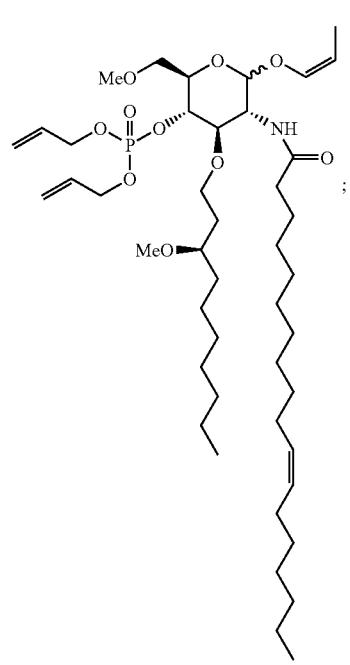
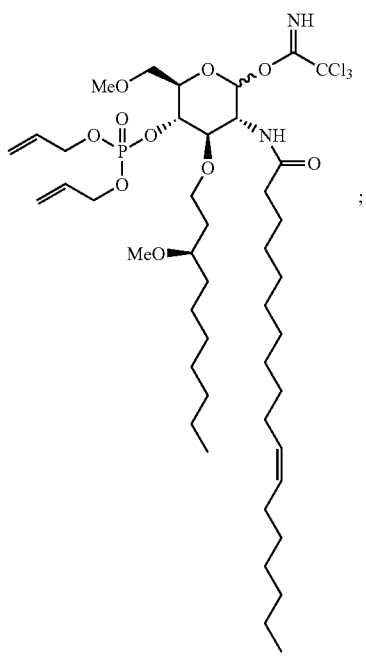
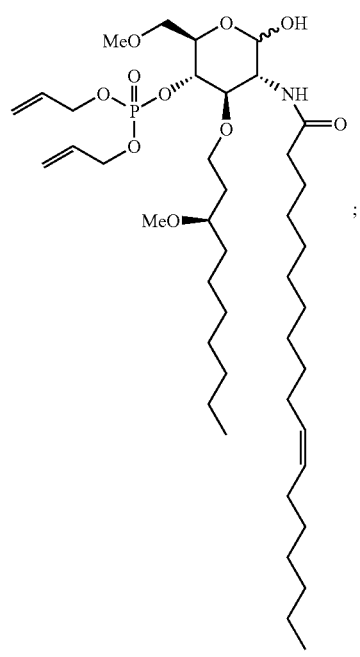

101
-continued
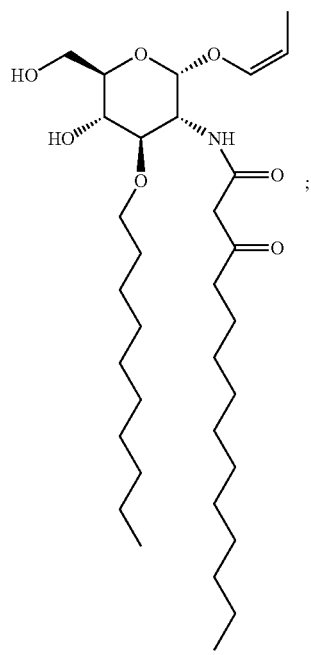
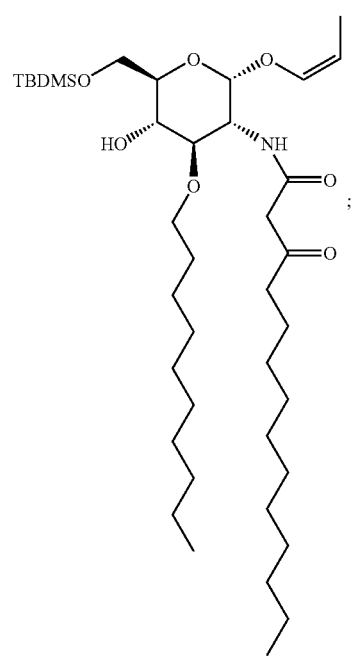
102
-continued
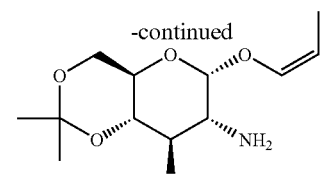
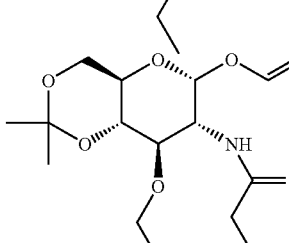
and
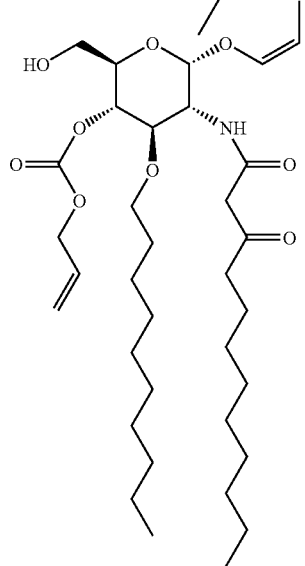

Synthetic Overview

The practitioner has a a well-established literature of glycoside chemistry to draw upon, in combination with the information contained herein, for guidance on synthetic strategies, protecting groups, and other materials and methods useful for the synthesis of B1287 and stereoisomers thereof.

The various patent documents and other references cited herein provide helpful background information on preparing certain monosaccharide starting materials. In particular, certain reagents and starting materials are described in detail by Christ, et al, in U.S. Pat. Nos. 5,530,113 and 5,935,938, and Rossignol et al. in U.S. Pat. No. 6,417,172, the entire contents of each of which are hereby incorporated by reference.

Moreover, the practitioner is directed to the specific guidance and examples provided in this document relating to exemplary intermediates useful for the synthesis of B1287 and stereoisomers thereof.

Examples of synthetic methods for practicing the invention are provided below, as detailed in Schemes 1-5, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary intermediates and protecting groups, it will be appreciated that the use of alternate starting materials, protecting groups and/or reagents will yield other intermediates, which are considered to fall within the scope of the present invention.

In certain exemplary embodiments of the present invention, preparation of the disaccharide scaffold 14 is achieved by coupling (i.e., glycosylation) trichloro-acetimidic acid ester intermediate 5 with alcohol intermediate 13, as depicted in Scheme 1. Exemplary syntheses of intermediates 5 and 13 are depicted in schemes 3, 5 and 6. In certain embodiments, the glycosylation conditions comprise zinc triflate (Zn(OTf)$_2$) and a suitable solvent (e.g., methylene chloride. In yet other embodiments, the glycosylation conditions comprise silver triflate (AgOTf) and a suitable solvent (e.g., methylene chloride). Alternatively, methane sulfonic acid (or ethane sulfonic acid) in a suitable solvent system (e.g., toluene:heptane 1:1) may be used.

Scheme 1

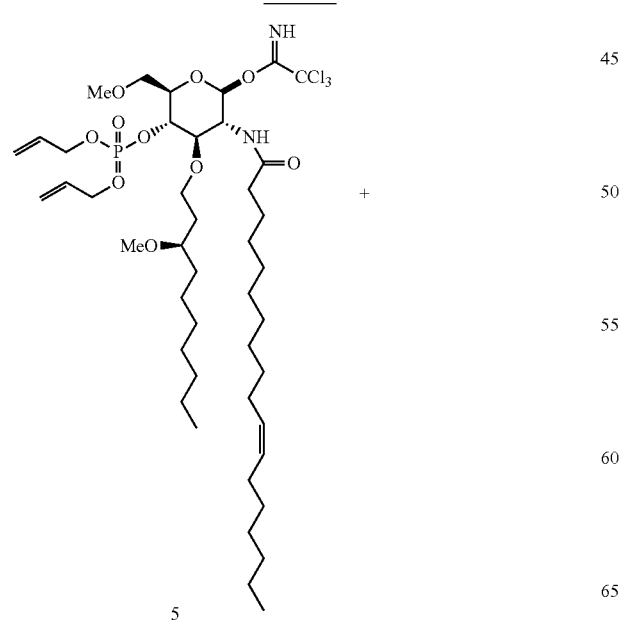

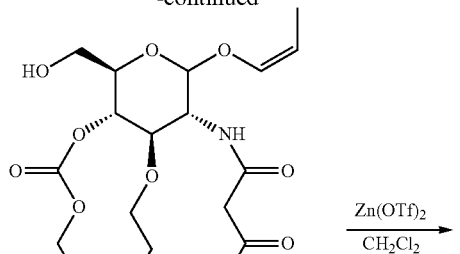

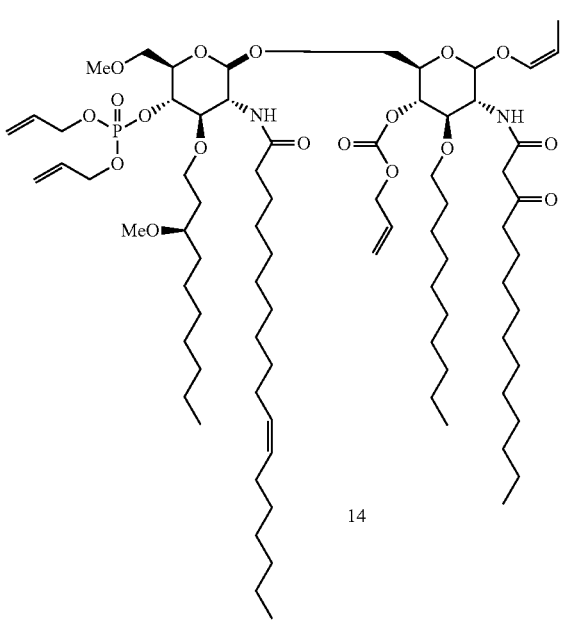

Disaccharide intermediate 14 may then be converted to B1287 in five steps, as outlined in Scheme 2. For example, hydrolysis of intermediate 14 with a strong acid (e.g., HCl or HF) in a suitable solvent (e.g., acetonitrile) affords alcohol intermediate 15. Phosphorylation of 15 in the presence of bis(allyloxy)diisopropyl aminophosphine in tetrazole, followed by oxidation (e.g., oxone) lead to the formation of diphosphorylated intermediate 16, which, upon hydrolysis in suitable conditions (e.g., Pd(PPh$_3$)$_4$, PPh$_3$, HOAc) lead to the formation of deprotected intermediate 17. Purification of 17 (e.g., suitable ion exchange chromatographic conditions, followed by treatment with aqueous NaOH) gives the desired compound B1287.

Scheme 2
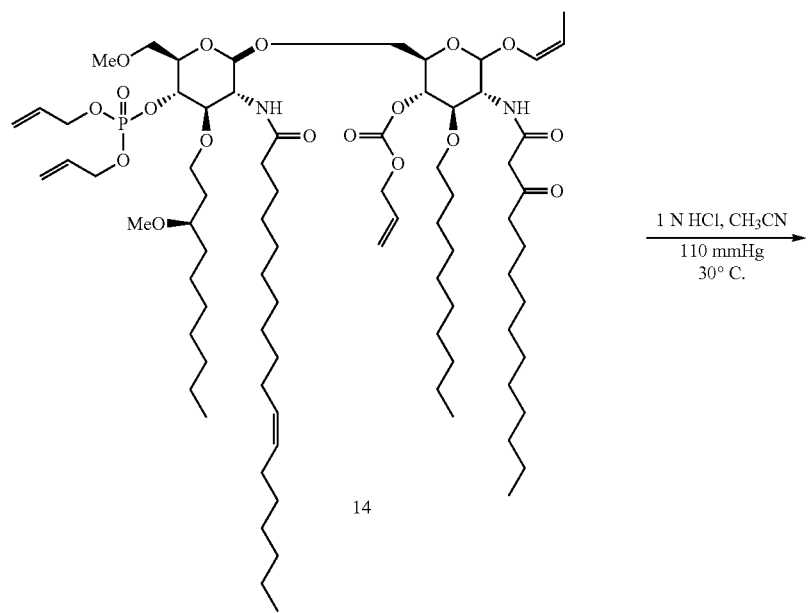
14
1 N HCl, CH₃CN
110 mmHg
30° C.
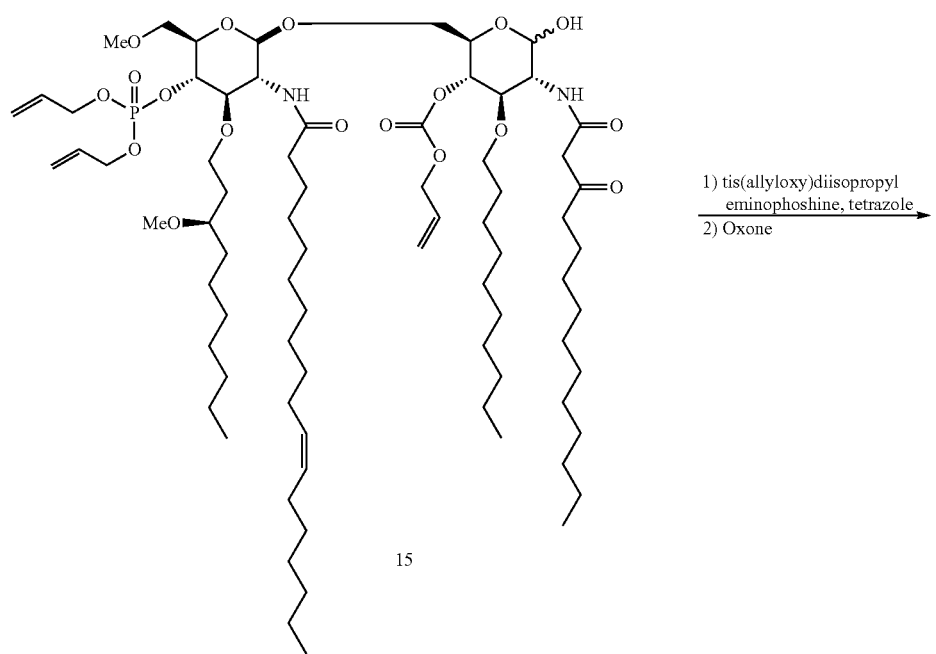
15
1) tis(allyloxy)diisopropyl
   eminophoshine, tetrazole
2) Oxone -continued
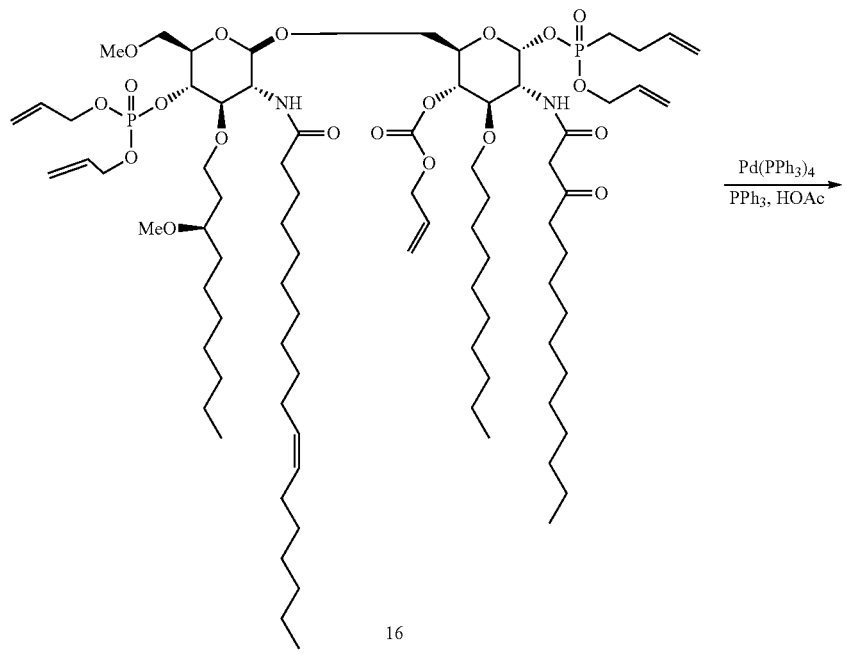
16
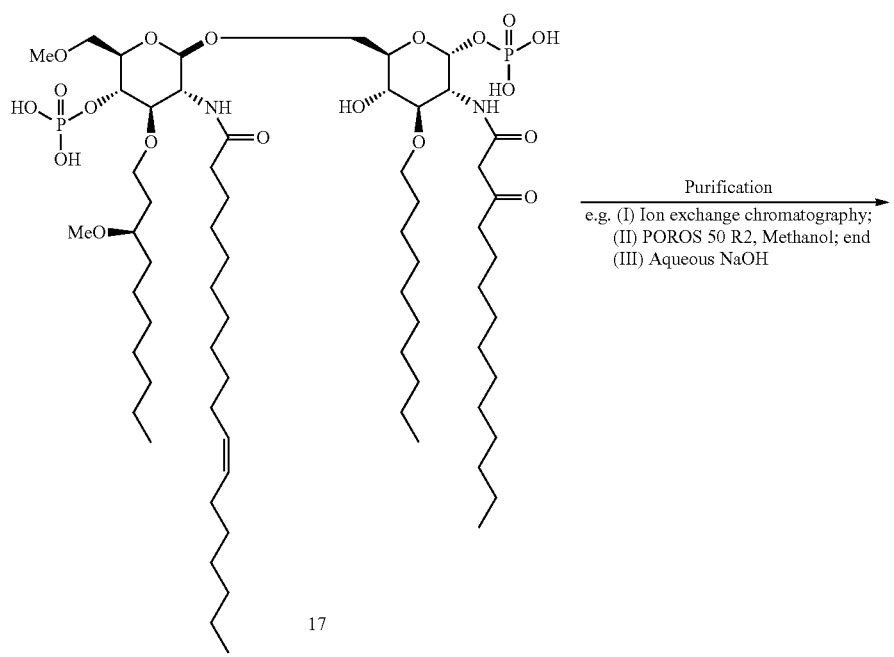
17

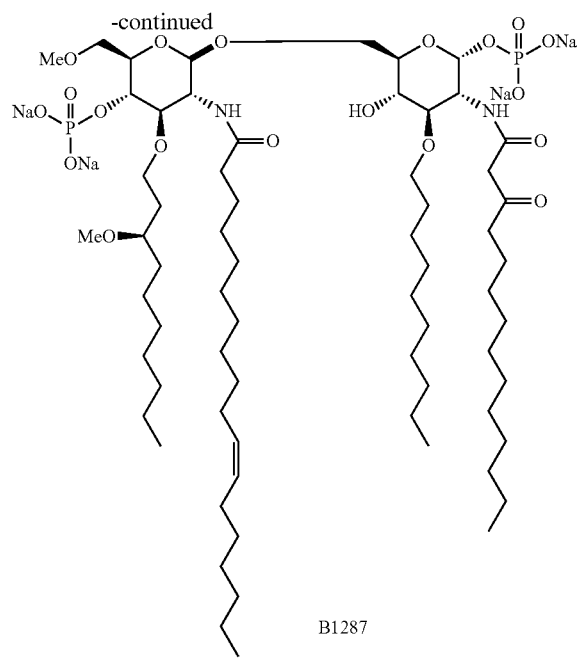

B1287

In certain exemplary embodiments, trichloro-acetimidic acid ester intermediate 5 is prepared in four steps from amine intermediate 1, as described in Scheme 3. For example, reaction of amine 1 with Δ-11-cis-vaccenoyl chloride under suitable conditions (e.g., saturated aqueous $NaHCO_3$) gives the corresponding amide 2. Phosphorylation of amide 2 under suitable conditions (e.g., bis(allyloxy)diisopropyl aminophosphine, followed by treatment with oxone) leads to intermediate 3, which, upon hydrolysis, gives the corresponding alcohol intermediate 4. Reaction of compound 4 with trichloroacetonitrile in the presence of a suitable base (e.g., $K_2CO_3$) leads to the desired intermediate 5. [Note: a preparation of starting material 1 is described in U.S. Pat. No. 6,417,172—see columns 26-32].

Scheme 3

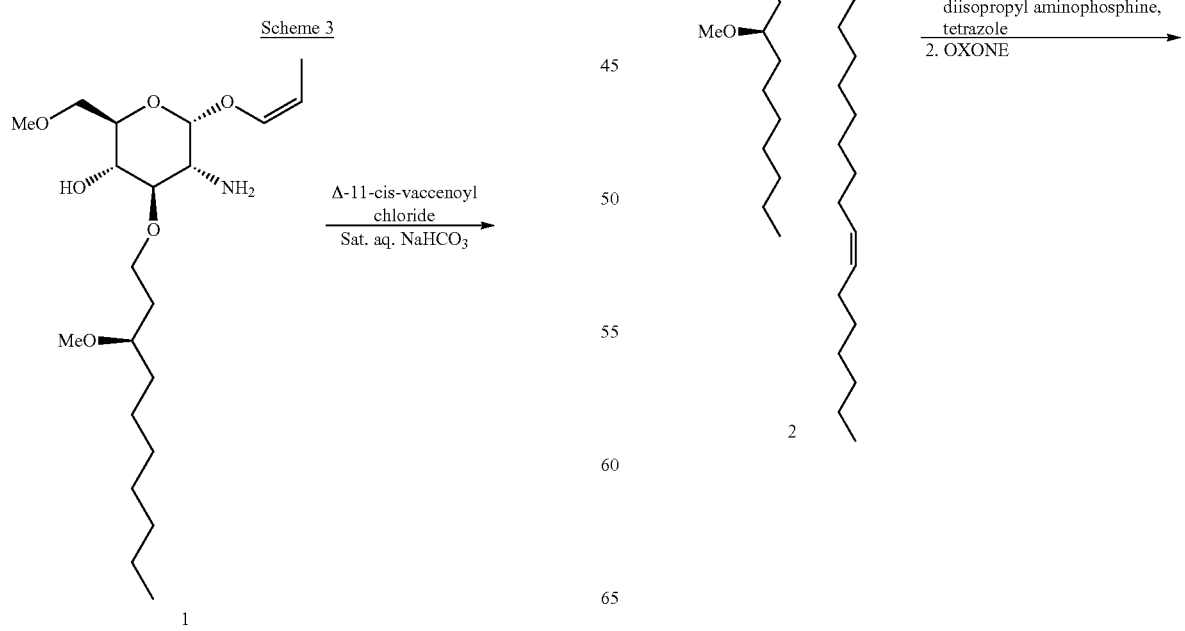

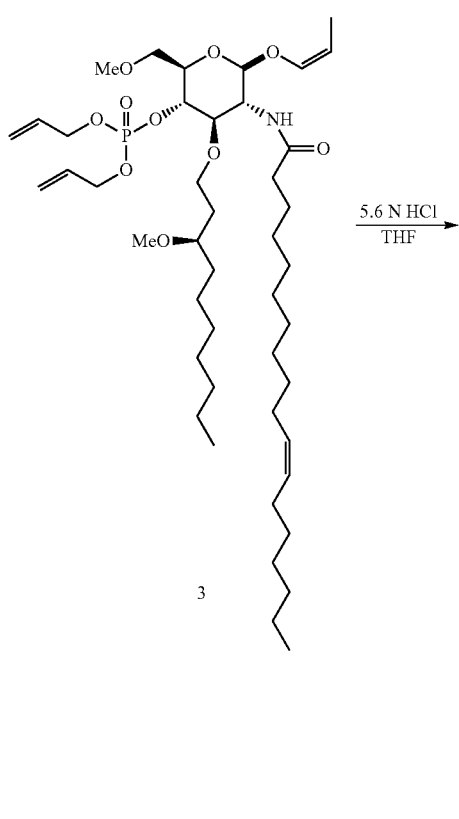

3

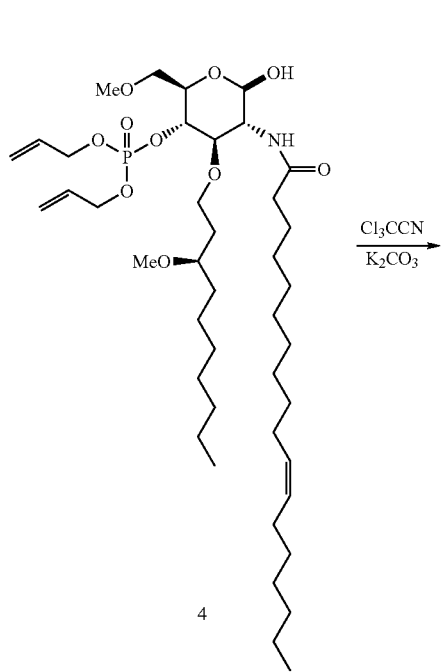

4

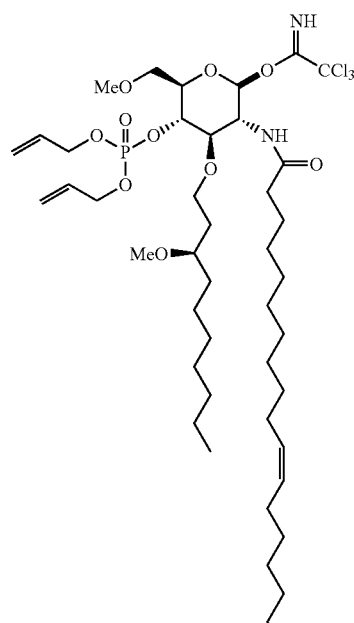

5

An exemplary synthesis of alcohol intermediate 13 is described in Scheme 4. For example, treatment of amine 9 with 3-Oxo-tetradecanoic acid in the presence of EDC in NMP gives the corresponding amide 10. Selective protection of the primary alcohol with TBDMSCl leads to the formation of silyl ether 11. Protection of the secondary alcohol moiety as its carbonic acid allyl ester may be accomplished by treating alcohol 11 with triphosgene, followed by reaction with allyl alcohol to give intermediate 12. Hydrolysis of the TBDMS ether leads to the desired intermediate 13. Scheme 5 depicts an exemplary synthesis of starting amine 9. For instance, alcohol 6 can be converted to the corresponding decanyl ether by deprotonation with NaH, followed by reaction with decanylmesylate to give the corresponding ether 7. Hydrolysis of the acetonide functionality in 7 leads to diol 8, which, upon treatment with a strong base, gives the corresponding amine 9. [Precursor 9 is known in the art, and its preparation, which is depicted in Scheme 5, has been described, for example, in U.S. Pat. No. 6,417,172—see columns 36-37]

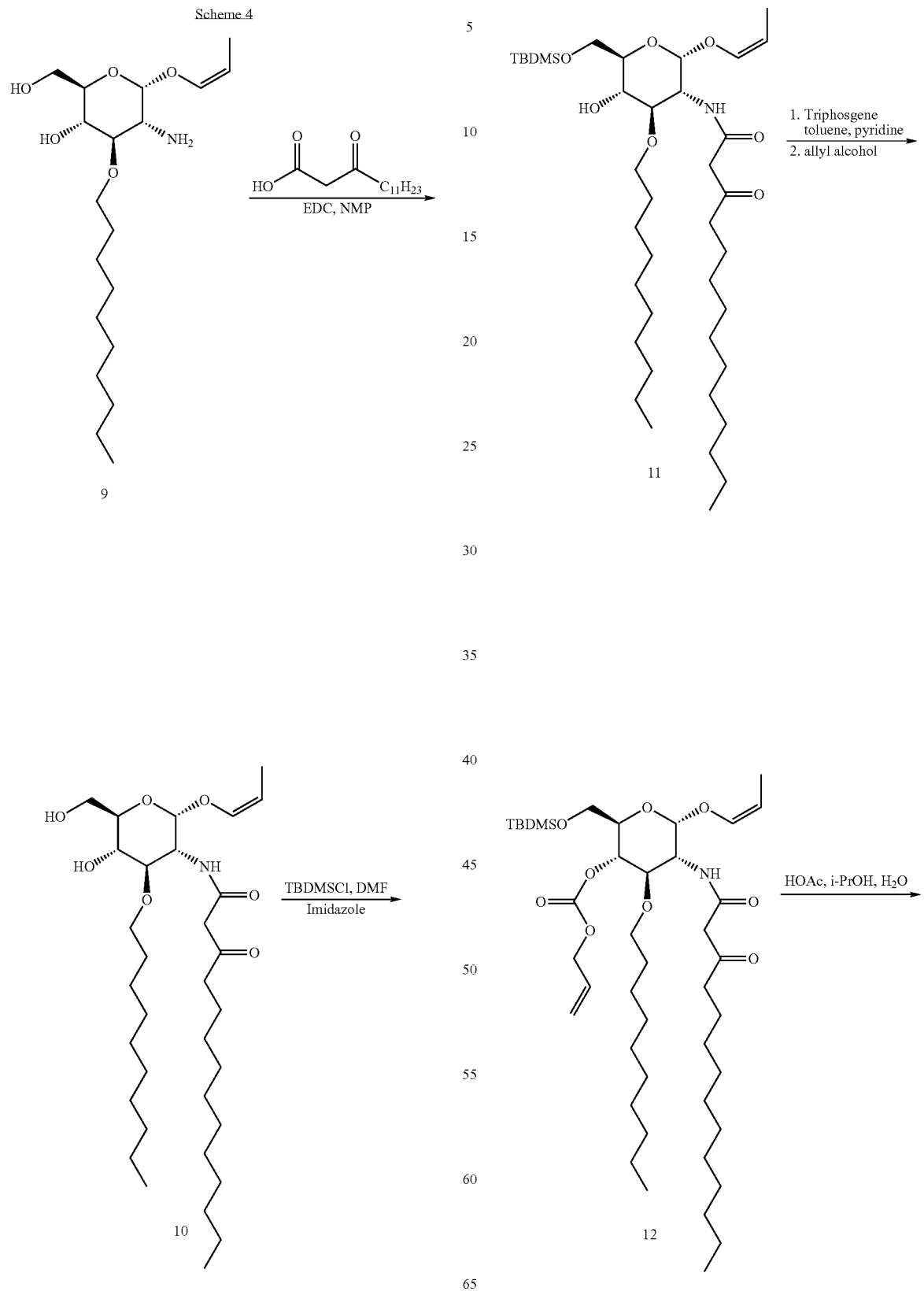

-continued

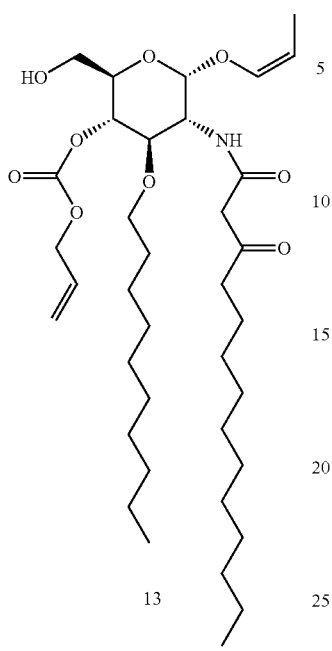

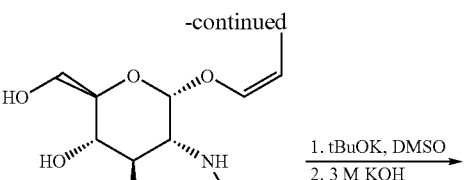

Scheme 5

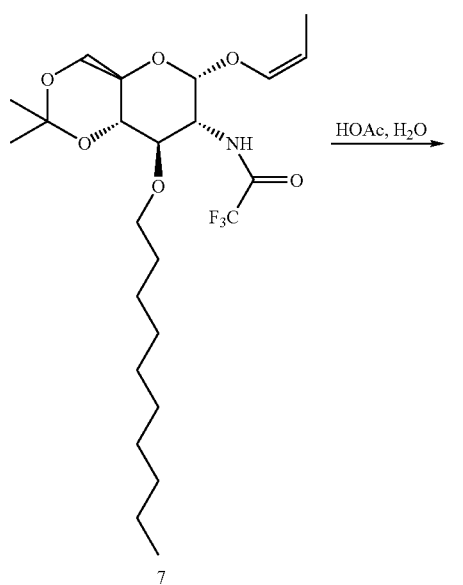

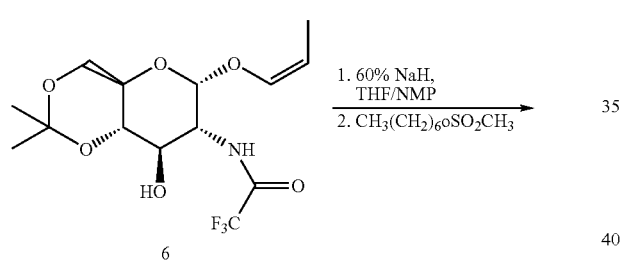

Alternatively, intermediate 13 may be accessed from the acetonide-protected derivative of compound 9 (e.g., compound 7), as depicted in Scheme 6. Thus, acetonide 7 may be subjected to basic hydrolysis to give the corresponding amine 19. Protection of the amine moiety as its 3-Oxo-tetradecanoic amide (20), followed by hydrolysis of the acetonide, leads to the corresponding diol 10, which can be converted to the desired intermediate 13 through a similar reaction sequence as that depicted in Scheme 3. This approach differs from that outlined in Scheme 3 in that it involves an acetonide intermediate rather than the corresponding diol. Although not wishing to be bound by any particular theory, it is believed that acetonide intermediates 19 and 20 may be easier to handle and to purify than their diol counterparts 9 and 10. In one aspect, the acetonide intermediates are less polar than their diol counterparts, and thus allow for easier chromatographic separation. In addition, diols 9 and 10 may be prone to side reactions (due to their free hydroxyl groups). The use of acetonides 19 and 20 avoid any such side reactions, and thus may lead to improved yields.

117
Scheme 6
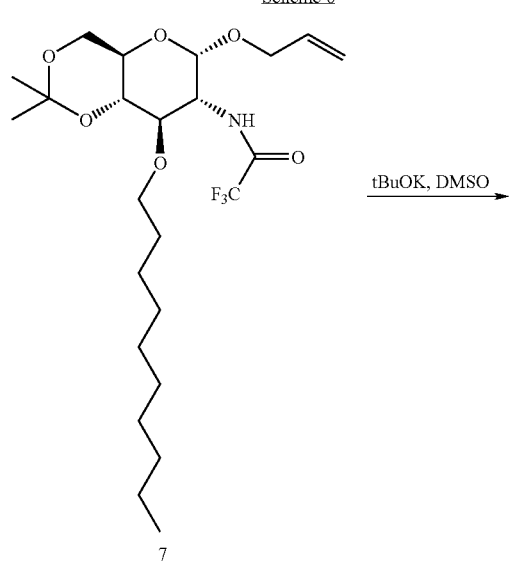
118
-continued
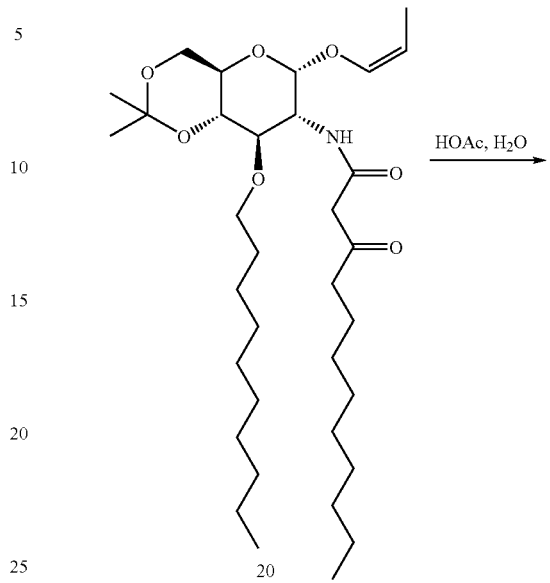
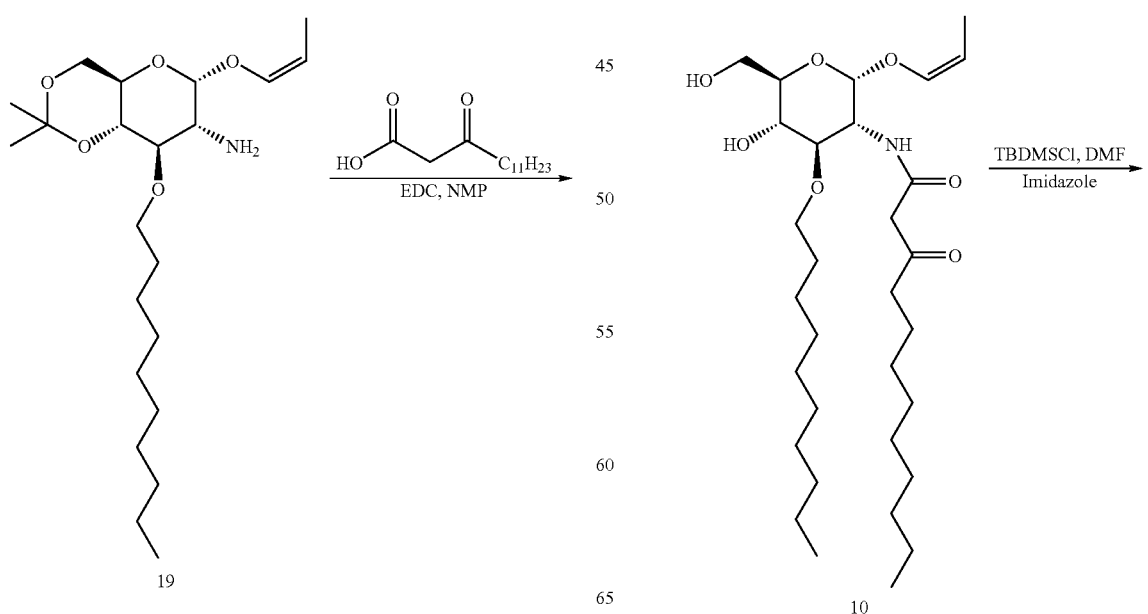

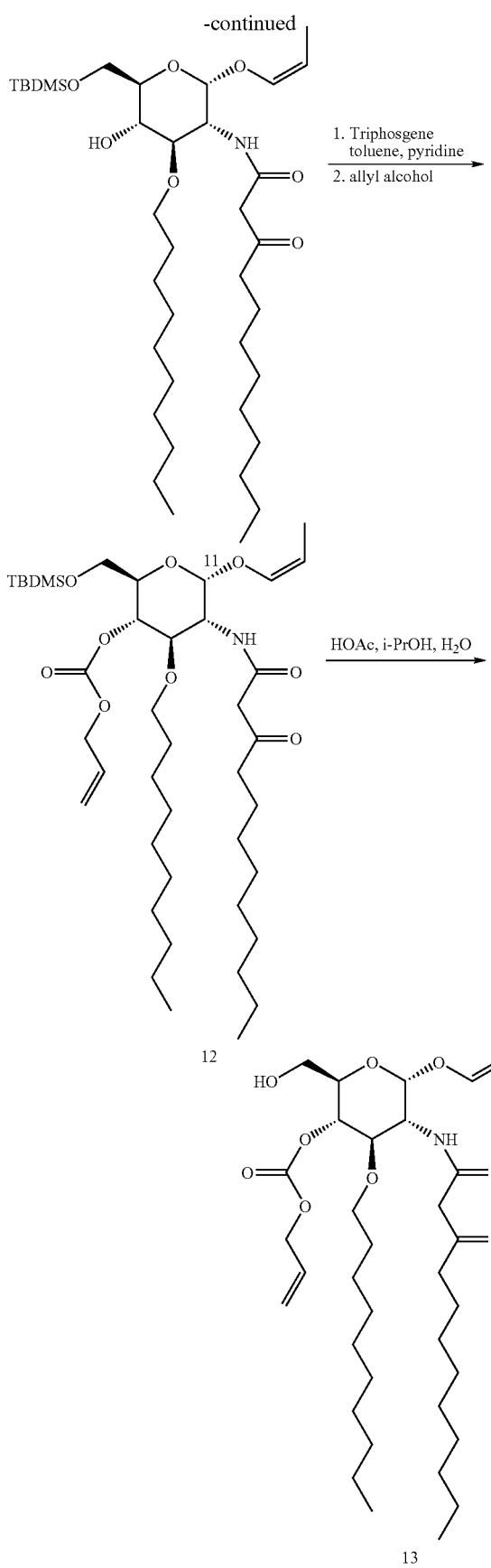

It will be appreciated that each of the reactions described in Schemes 1-6 above can be carried out using reagents and conditions as described for the synthesis of various types of exemplary intermediates described above, or they may be modified using other available reagents, protecting groups or starting materials. For example, a variety of amide formation conditions, phosphorylation and pyranose protecting/deprotecting conditions are well-known in the art and can be utilized in the method of the invention. See, generally, March, Advanced Organic Chemistry, 5$^{th}$ ed., John Wiley & Sons, 2001; and "Comprehensive Organic Transformations, a guide to functional group preparations", Richard C. Larock, VCH publishers, 1999; the entire contents of which are incorporated herein by reference and "Protective Groups in Organic Synthesis" Third Ed. Greene, T. W. and Wuts, P. G., Eds., John Wiley & Sons, New York: 1999, the entire contents of which are hereby incorporated by reference.

In summary, the present invention provides a synthesis of B1287 in significantly fewer steps than previously reported methods. The instant method affords the title compound in higher overall yields and eliminates major safety concerns associated with existing methods (i.e., the present method does not involve azide chemistry, and thus is more readily applicable for preparations of B1287 on an industrial scale).

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Synthetic Overview

The practitioner has a well-established literature of carbohydrate chemistry to draw upon, in combination with the information contained in the many examples which follow, for guidance on synthetic strategies, protecting groups, and other materials and methods useful for the synthesis of B1287. The title compound may be prepared according to the synthetic method described herein using any of the available relevant chemical transformations, combined with protection and deprotection as desired or required. Such processes, when used to prepare the title compound, are illustrated by the following representative examples. The various starting materials are either commercially available or may be obtained by standard procedures of organic chemistry. The preparation of certain starting materials is described elsewhere (See, for example, U.S. Pat. Nos. 5,530,113, 5,935,938 and 6,417,172).

General Reaction Procedures

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance or by high-pressure liquid chromatography (HPLC), of a suitably worked up sample of the reaction mixture.

Listed below are abbreviations used for some common organic reagents referred to herein:
DPP: Bis(allyloxy) N,N-diisopropylamino phosphine
DMF: N,N-Dimethylformamide
DMSO: Dimethylsulfoxide
EDC: 3-Ethyl carbodiimide hydrochloride
NMP: N-Methyl pyrrolidone
THF: Tetrahydrofuran Example 1

Exemplary Preparation oB1287 Left-Hand Fragment (5)

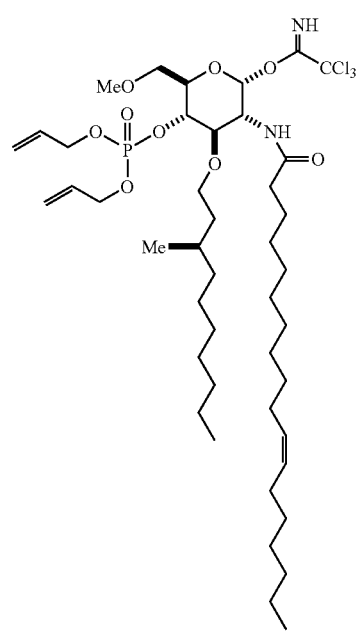

(5)

Step 1: Preparation of Compound 2

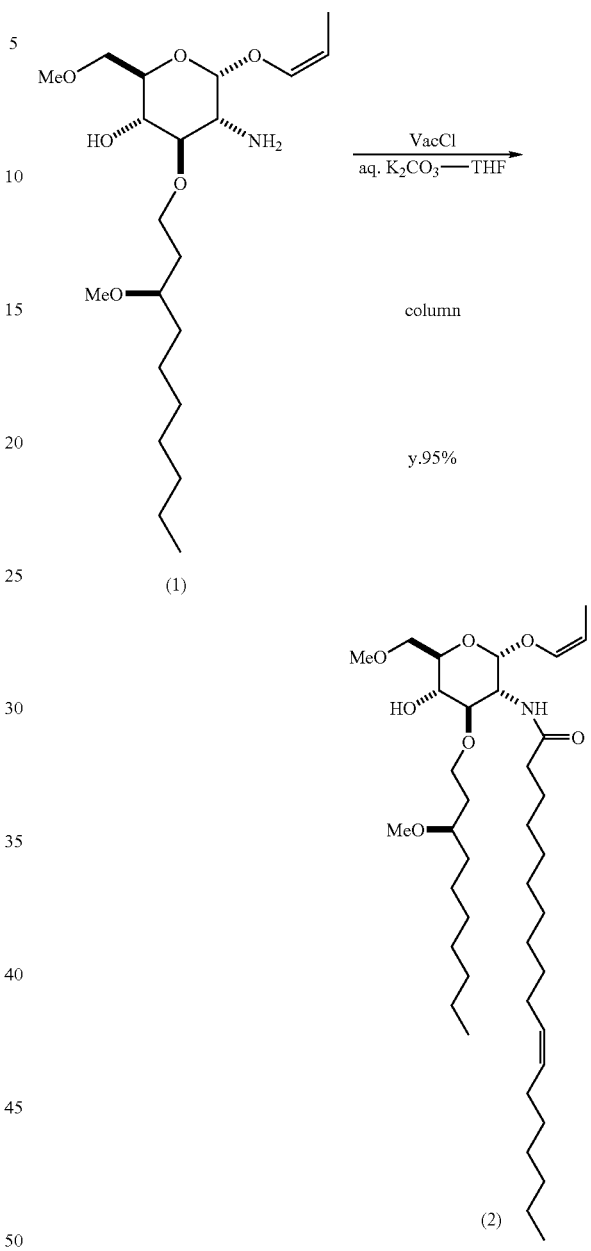

To a solution of amine 1 (10.45 g) in tetrahydrofurane (140 mL) was added 1% aqueous potassium carbonate (650 mL). The mixture was stirred vigorously and cis-11-octadecenoyl chloride (10 mL) was added. After stirring for 250 minutes, the mixture was extracted with ethyl acetate (300 mL). The organic layer was washed with brine (300 mL×2) and was separated. After concentration, the residue was purified by silica gel column chromatography (hexane/ethyl acetate=2/1) to give 15.9 g of desired compound 2 as a white solid.

Crude compound 2 (398 g) was dissolved in $CH_3CN$ (3090 ml). The resulting solution was slowly cooled down to 0° C. The precipitate was collected by filtration, washed with cold $CH_3CN$, and dried under high vacuum to give 292 g of pure compound 2.

Step 2: Preparation of Compound 3

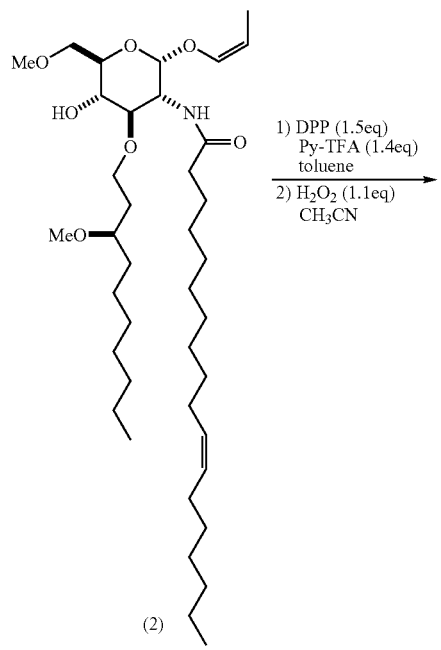

(2)

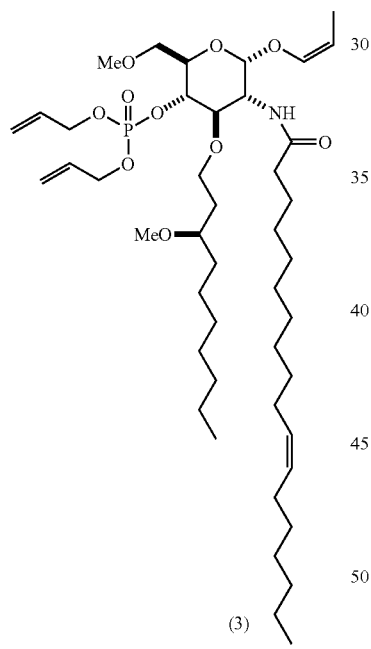

(3)

To a solution of amide 2 (30 g) in toluene (117.8 mL) was added diallyl diisopropylphosphoramidite (15.5 g) and pyridinium trifluoroacetate (12.4 g). The reaction mixture was stirred for 1.4 hr at ambient temperature and H₂O₂ (30-35%)/acetonitrile (4.8 ml/117.8 mL) was then added under nitrogen gas at −25° C. After stirring for 2.5 hr at 10° C., toluene (117.8 mL) and 3% aqueous sodium thiosulfate (117.8 mL) were added. The mixture was stirred vigorously and the organic layer was separated. The organic layer was washed with 1N hydrochloric acid (117.8 mL) and 5% brine (235.6 mL×2). The organic solvent was removed under reduced pressure to give the desired compound (3) (41.4 g) as pale yellow oil.

Step 3: Preparation of Compound 4

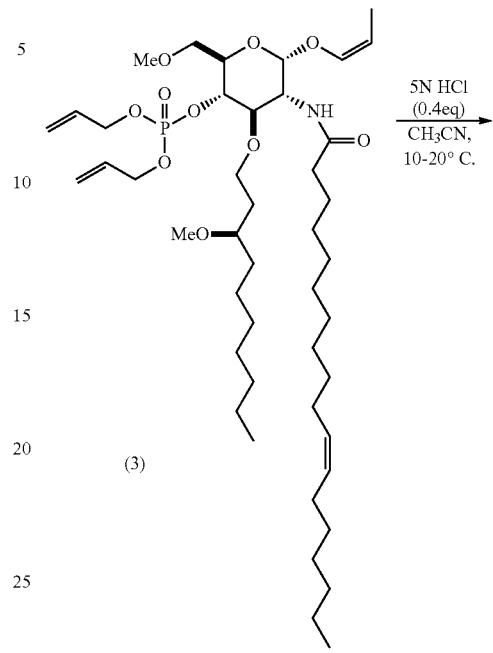

(3)

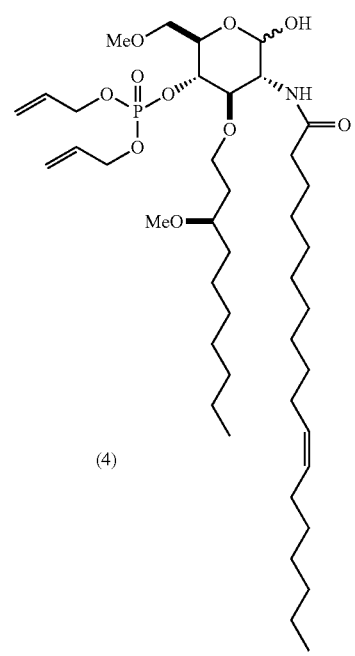

(4)

To a solution of compound 3 (56.5 g) in toluene (339 mL) and acetonitrile (170 mL) was added 5 N hydrochloric acid (13.7 mL) and the mixture was stirred for 2 hr at room temperature. After the mixture was washed with 10% brine (170 mL), 5% aqueous sodium bicarbonate (170 mL) and 10% brine (170 mL), the organic solvent was removed under reduced pressure to give 48.4 g of crude product. The crude product was azeotroped three times with acetone (40 mL×3) and the residue (20.5 g) was recrystallized from acetone-water (3/2, 170.6 mL) to give the desired product 4 (12.83 g) as white crystals.

Step 4: Preparation of Compound 5

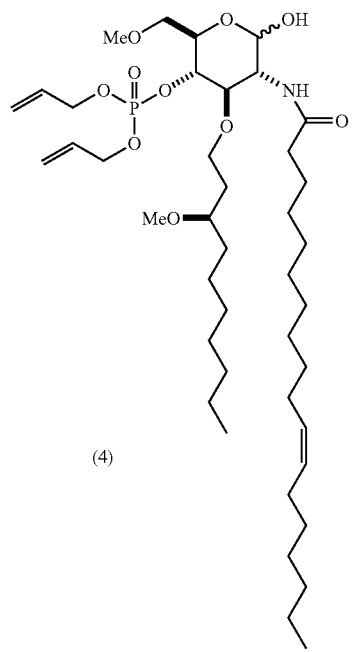

(4)

$\xrightarrow{\text{CCl}_3\text{CN (5eq)} \atop {\text{K}_2\text{CO}_3 \text{(1eq)} \atop \text{AcOEt (x1 vol)-} \atop \text{H}_2\text{O (1\%)}}}$

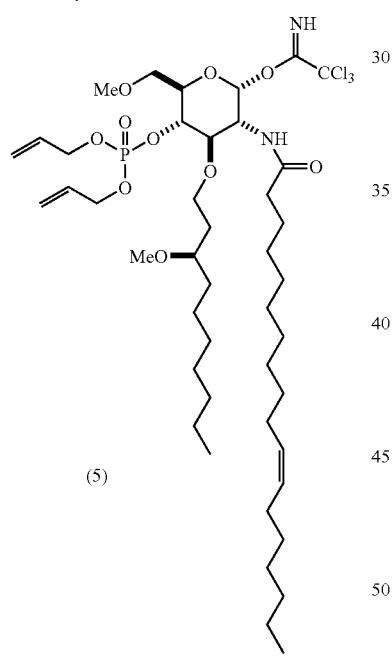

(5)

To a suspension of compound 4 (10.74 g) and potassium carbonate (1.93 g) in methyl acetate (20.2 mL) was added trichroloacetonitrile (6.55 mL). The mixture was cooled with ice-water bath and water (0.3 mL) was added. The reaction mixture was stirred for 5 hr at room temperature and magnesium sulfate (2 g) was added. After stirring for another 20 min, the mixture was filtered through celite (10 g) and the filter cake was washed with methyl acetate (3×20.2 mL). The combined filtrates were concentrated under reduced pressure and the resulting residue was azeotroped with methyl acetate (3×20.2 mL). After concentration, the desired product 5 (12.86 g) was obtained as yellow oil.

Example 2

Other Exemplary Preparation of B1287 Left-Hand Fragment (5)

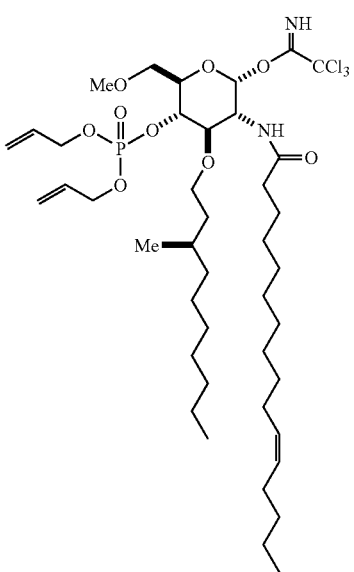

(5)

Step 1: Preparation of Compound 2

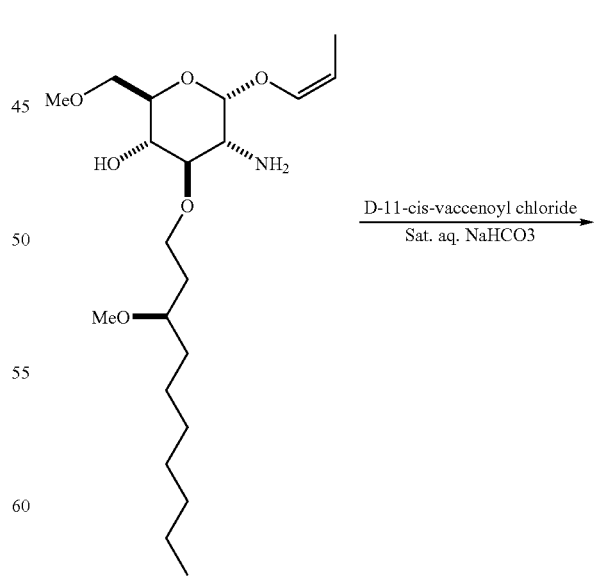

(1)

$\xrightarrow{\text{D-11-cis-vaccenoyl chloride} \atop \text{Sat. aq. NaHCO3}}$

-continued

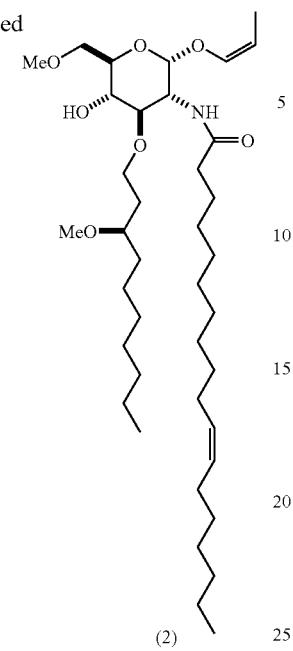

(2)

To a solution of compound 1 (4.9367 g, 12.23 m mole, 1 eq.) in THF (100 ml) was added an aqueous solution of potassium carbonate (9.97 g, 72.25 mmol, 5.9 eq.) in water (10 ml) under vigorous stirring. [Note: a preparation of staring material 1 is described in U.S. Pat. No. 6,417,172—see columns 26-32. The number of moles was calculated without purity correction.] The resulting mixture was cooled with tap water, and vaccenoyl chloride (4.043 g, 13.44 mmol, 1.1 eq.) was injected in over 5 min. White particles precipitated immediately. The reaction was completed in 15 min. The reaction mixture was partitioned between EtOAc and brine. The routine work-up and the evaporation of the dried organic phase finished the crude desired product 2 (8.2821 g) as a white solid in 100.0% yield. Rf 0.44 (silica gel, EtOAc/Hexane=1/1). $^1$H-NMR (CDCl$_3$) δ: 6.05 (d, 1 H, propenyl), 5.65 (d, 1H, NH), 5.33 (m, 2H, vinyl protons of the vacenoyl moiety), 5.03 (bs, 1H, adjacent to propenyloxy), 4.55, m, 1H, propenyl), 4.24 (m, 1 H, adjacent to amide).

Step 2: Preparation of Compound 3

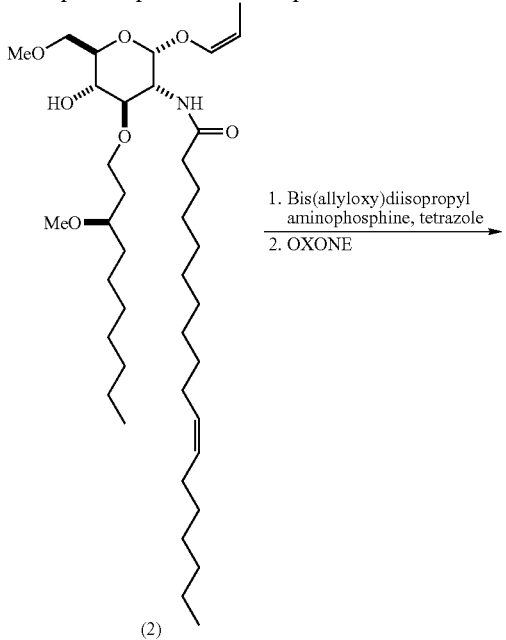

(2)

1. Bis(allyloxy)diisopropyl aminophosphine, tetrazole
2. OXONE

-continued

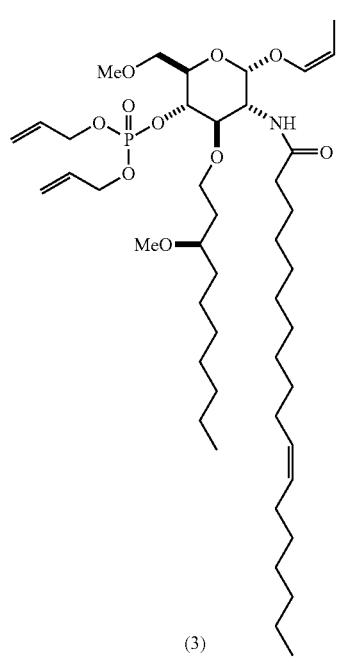

(3)

1-H tetrazole (1.8405 g, 26.29 mmol, 4.18 eq.) was added into a solution of compound 2 (4.200 g, 6.2875 mmol, 1 eq.) in dichloromethane (40 ml). The suspension was stirred and cooled to <5° C. with an ice/water bath. Bis(allyloxy) N,N-diisopropylamino phosphine (2.190 g, 8.928 mmol, 1.42 eq.) was added over 10 min. The resulting solution was stirred at 5° C. for one hour, allowed to warm to room temperature and stirred at 20° C. for 10 minutes, at which point phosphite formation was complete (Rf, 0.82, silica gel, EtOAc/Hexane=1/1). The reaction mixture was cooled with a cooling bath and was slowly added to a cool (2° C.) solution of Oxone (6.45 g, 10.49 m mole. 1.67 eq.) in water (17 ml) and THF (10 ml) over 15 min (exothermic) while maintaining the reaction mixture between 2 and 10° C. After 20 minutes, the reaction was complete, and the reaction mixture was quenched with a solution of sodium ascorbate (2.8 g, 14.13 mmol, 2.25 eq.) in water (16.5 ml). The resulting mixture was stirred for 20 min (Rf, 0.32, silica gel, EtOAc/Hexane=1/1), and was then partitioned between EtOAc and a 10% sodium bicarbonate aqueous solution. The aqueous layer was extracted with ethyl acetate. The combined organic extracts were washed with brine three times, dried and evaporated. The crude product (5.649 g, yield 108.5%) was chromatographed on 160 g of silica gel (solvent: EtOAc/Hexane=1/2, then 1/1) to give 4.146 g (79.6% yield) of pure compound 3. $^1$H-NMR (CDCl$_3$) δ: 6.07 (m, 1H, propenyl), 5.92 (m, 2H, allyl protons), 5.7 (1H, NH), 5.35 (m, 2H, allyl protons, trans), 5.3 (m, 2H, vinyl protons of the vaccenoyl moiety), 5.2 (m, 2H, allyl protons, cis), 5.07 (d, 1H, adjacent to propenyloxy), 4.5 (m, 5H, propenyl, CH$_2$ of allyls), 4.42 (q, 1H, adjacent to phosphate), 4.24 (m, 1H, adjacent to amide).

Step 3: Preparation of Compound 4

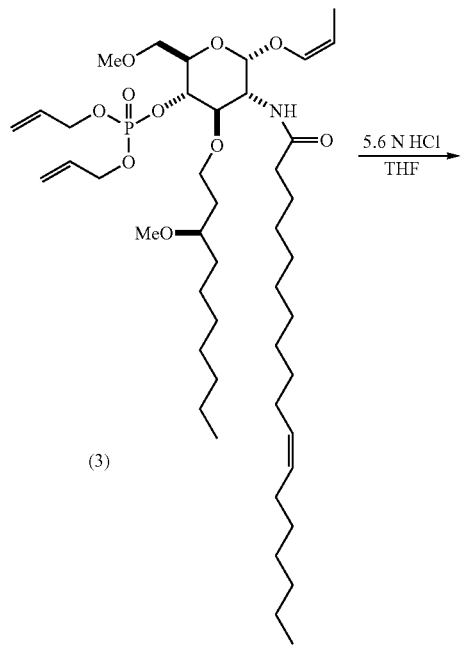

Diluted hydrochloric acid (1.478 g conc. 14.98 mmol, 4.6 mmol, in water 1.269 g) was added into a solution of compound 3 (2.702 g, 3.26 mmol, 1 eq.) in THF (10 ml) at room temperature with stirring. The hydrolysis was completed over 3 hr. The reaction mixture was poured into a mixture of aq. Sodium bicarbonate (10 g in 25 ml of water) with 300 ml of ethyl acetate. The organic phase was separated, dried, and evaporated. A milky white semi-solid was obtained, which turned to a solid the next day (2.394 g, 93.1% yield). Rf, 0.05 (silica gel, EtOAc/Hexane=1/1), 0.32 (silica gel, EtOAc neat). $^1$H-NMR (CDCl$_3$) d: 6.05 (d, 1H, NH), 5.9 (m, 2H, allyls), 5.36 (m, 2H, allyls, trans), 5.32 (m, 2H, vinyls of vaccenoyl), 5.25 (m, 2H, allyls, cis), 4.6 (m, 4H, CH$_2$ of allyls), 4.3 (q, 1H, adjacent to phosphate), 4.1 (m, 2 H, adjacent to amide, and OH).

Step 4: Preparation of Compound 5

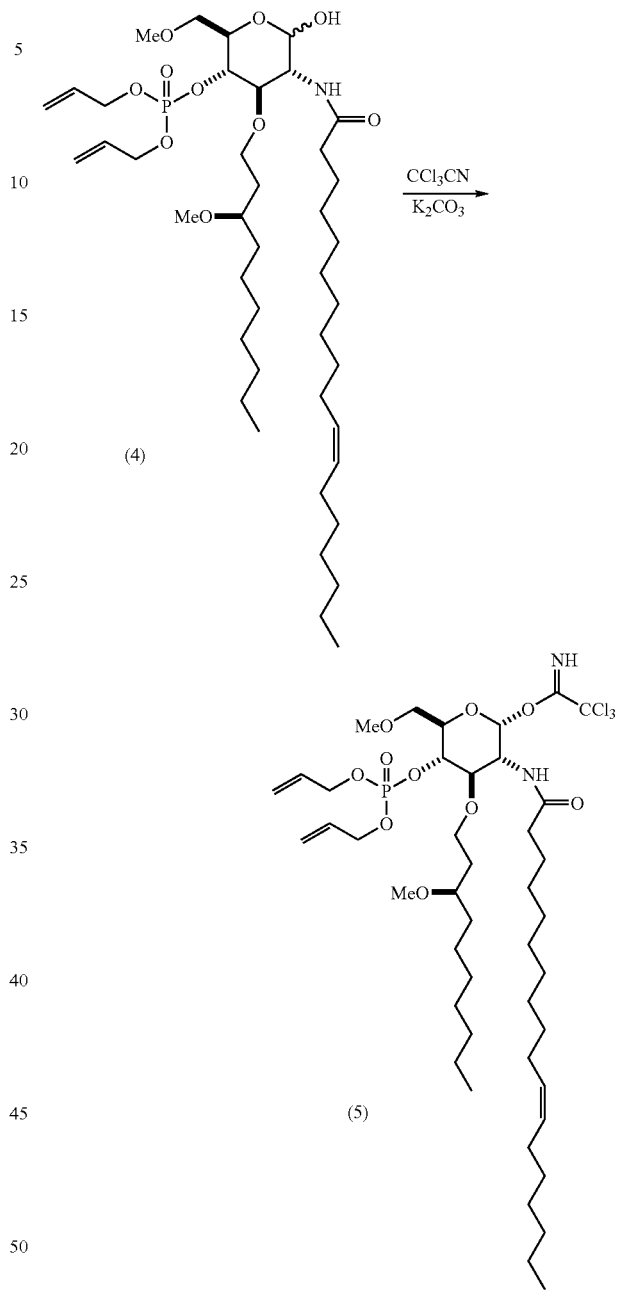

A solution of compound 4 (715.7 mg, 0.908 mmol, 1 eq.) in trichloroacetonitrile (6 ml, 59.8 m mole, 65.9 eq.) was added to a potassium carbonate solution (325 mesh, 1.63 g, 11.8 m mole, 13 eq.) at tap water temperature with vigorous stirring. The reaction mixture was stirred at room temperature for 3 hrs. The mixture was filtered through sintered glass funnel. Evaporation of the resulting filtrate furnished the crude product 5 (1.006 g, 100% yield). Rf, 0.32 (major) and 0.47 (minor) (two anomers in the ratio of 4/1). $^1$H-NMR (CDCl$_3$) δ: 8.7 (d, 1H, NH of imidate), 6.4 (s, 1H, adjacent to imidate), 5.92 (m, 2H, vinyls), 5.85 (d, 1H, NH of amide), 5.4 (m, 2H, allyls, trans), 5.32 (m, 2H, vinyls of vaccenoyl), 5.25 (d, 2H, allyls, cis), 4.55 (m, 4H, CH$_2$ of allyls), 4.35 (m, 1H, adjacent to phosphate), 3.9 (m, 1H, adjacent to amide).

Example 3

Exemplary Preparation of B1287 Right-Hand Fragment (13)

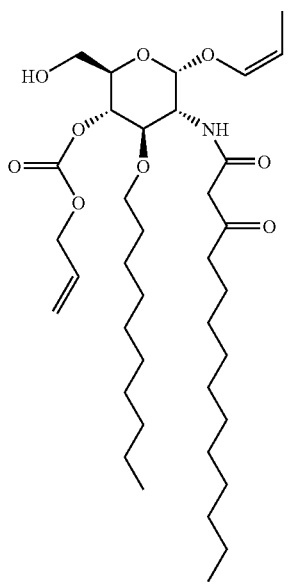

(13)

Step 1: Preparation of Compound 7

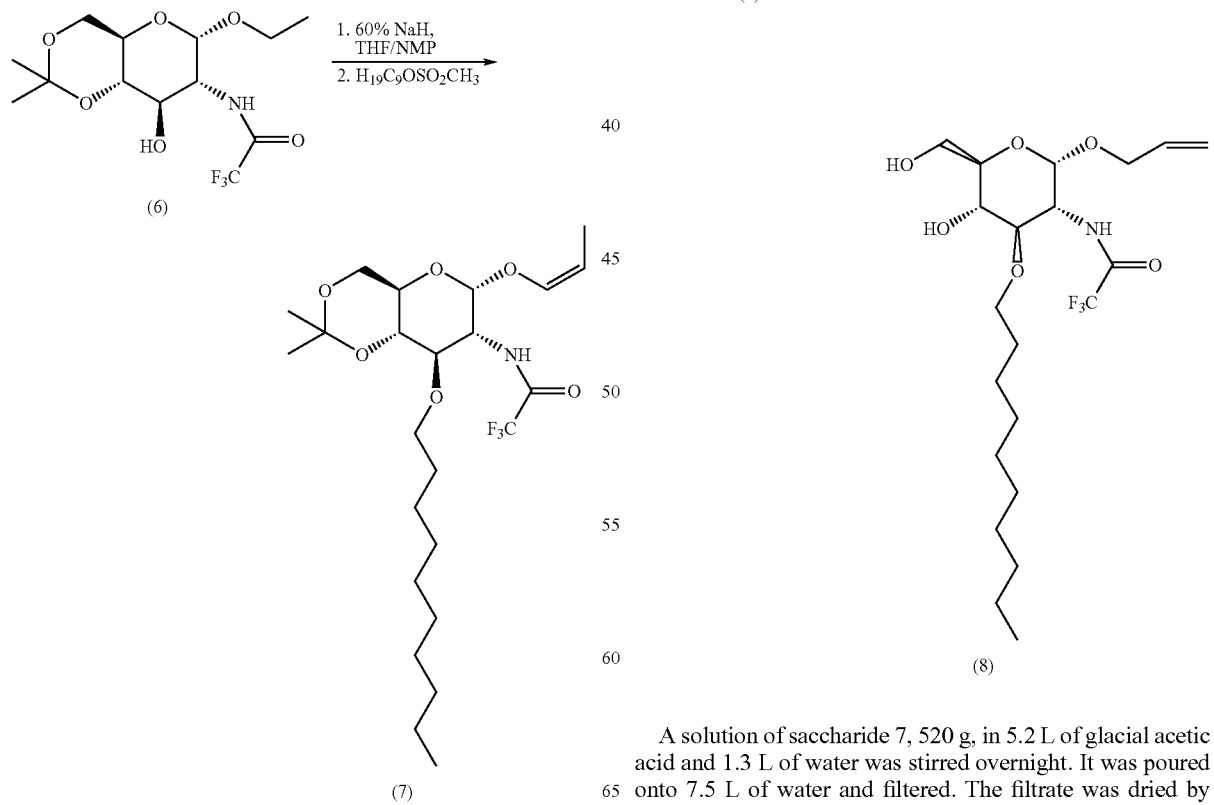

To a suspension of 60% sodium hydride mineral oil dispersion in 1 L of THF and 470 mL of DMF was added a solution of alcohol 6 in 280 mL of DMF and 1 L of THF over 1 hour. The mesylate, 470 g, was then added over 15 minutes. After 2 days, 400 mL of methanol was added, followed by 4 kg of ice and 4 L of water. This mixture was extracted with 2.times.4 L of ethyl acetate. The combined organic layers were dried and the solvent was removed under reduced pressure. The residue was chromatographed on silica. Gradient elution with hexane:EtOAc (39:1 to 2:1) gave 618 g of desired compound 7.

Step 2: Preparation of Compound 8

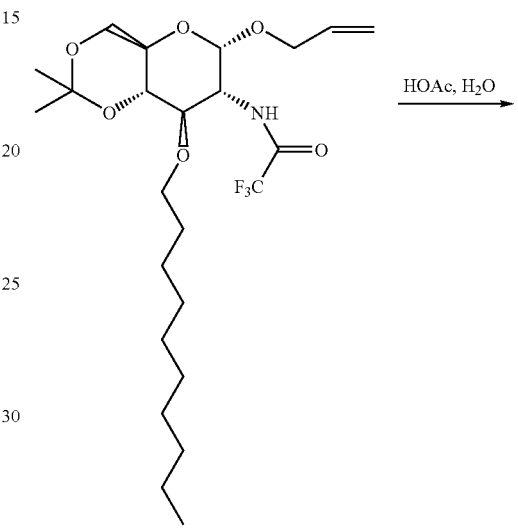

A solution of saccharide 7, 520 g, in 5.2 L of glacial acetic acid and 1.3 L of water was stirred overnight. It was poured onto 7.5 L of water and filtered. The filtrate was dried by azeotropic distillation with toluene (3×500 mL) under reduced pressure to give 458 g of desired compound 8.

Step 3: Preparation of Compound 9

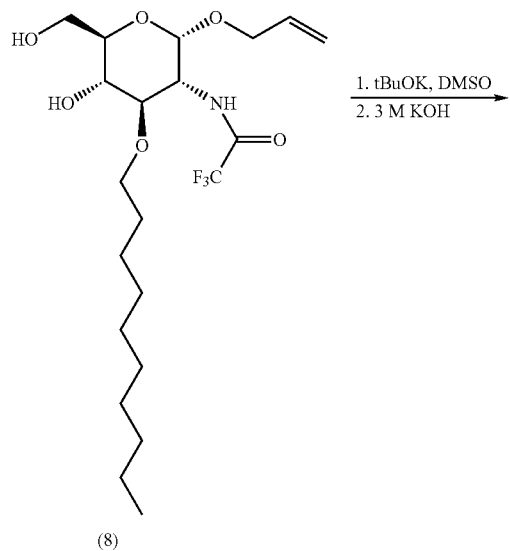

Step 4: Preparation of Compound 10

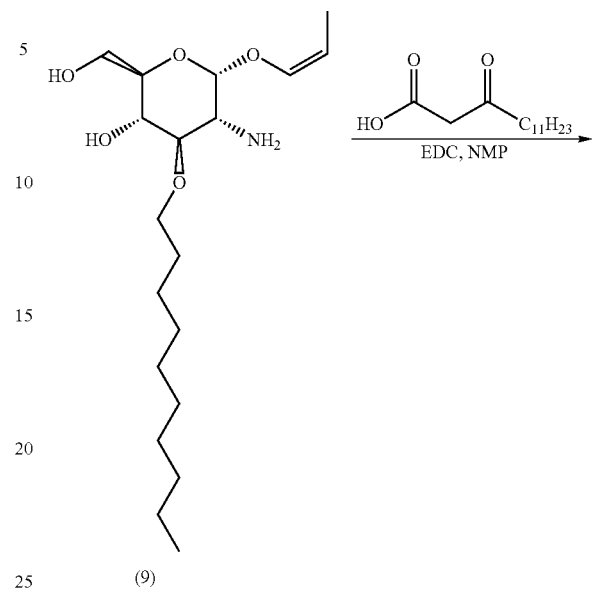

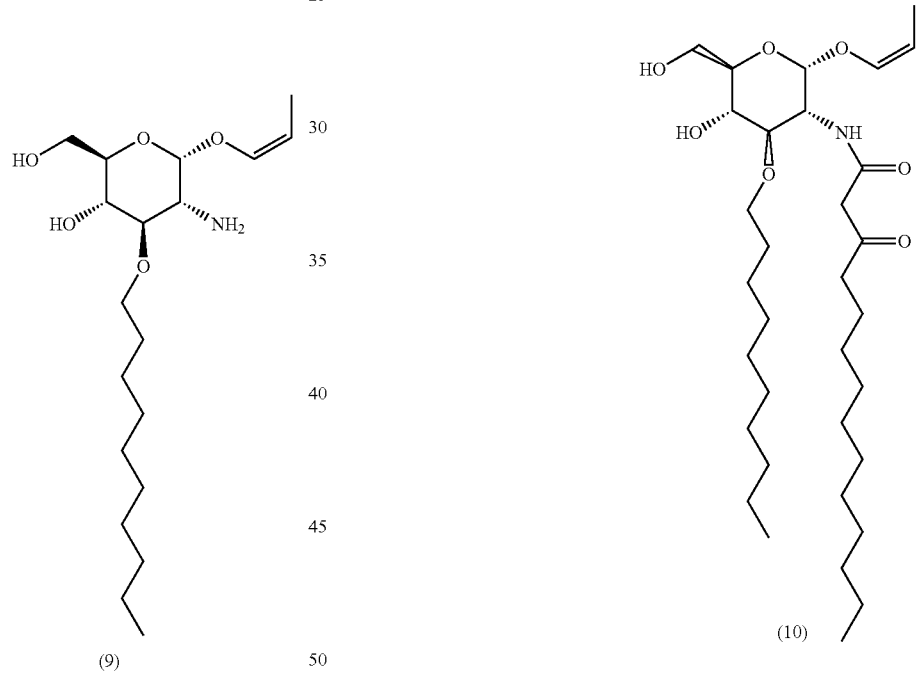

This reaction was run under argon. To a suspension of potassium t-butoxide, 295 g, in DMSO, 1 L, was added a solution of 340 g of saccharide 8 in 1.5 L of DMSO. The mixture was heated to 85° C. for $1^{1/4}$ hour and 1.4 L of 3 M aqueous potassium hydroxide was added and the mixture stirred overnight at 85° C. The mixture was cooled to room temperature and poured onto a mixture of 3.5 L of brine and 3.5 L of water. The mixture was extracted three times with methylene chloride, the mixture dried and the solvent was removed under reduced pressure. The residue was chromatographed on silica. Gradient elution with methylene chloride:methanol (19:1 to 4:1) gave 740 g of desired product 9.

A mixture of compound 9 (12.5 g, 34.77 mmol, 1 eq., crude, one spot on TLC: Silica gel, EtOAc/hexane=1/0, Rf 0.34), 3-Oxo-tetradecanoic acid (16.9 g, 69.73 mmol, 2.0 eq.), and EDC (27.83 g, 145.2 mmol, 4.18 eq.) was left in cold room (−30° C.) for 20 min. NMP (100 ml, 1042 mmol, 29.97 eq.) was injected into the mixture with stirring under nitrogen gas at room temperature. TLC indicated that the reaction was nearly complete after 220 min (Silica gel, EtOAc/Hexane=2/1, starting material: Rf=0.1; product: Rf=0.43). After 5 hours, the reaction mixture was partitioned between ethyl acetate and brine. The organic phase was further washed with brine while the aqueous phases were extracted with ethyl acetate. The organic extracts were combined. TLC on the solution containing the crude product indicated the presence of some starting material. The solution was concentrated to 155.6 g. After hexane (89 g) was added, the solution was left in the hood overnight (15 hours). A white gummy material precipitated. The mixture was filtered after it was chilled in cold room (−30° C.) for 20 min. The white filter cake was suspended in 40 mL of EtOAc/hexane (1/10). The resulting paste was filtered. The white filter cake was treated with EtOAc/hexane (1/10, 40 ml) again, filtered and dried. The procedure furnished 33.41 g of pure white crystalline powder, which only showed one spot on TLC. Yield 59.7%. All the filtrates were combined and evaporated. The residue obtained (18.2 g) was chromatographed (silica gel, 178 g; solvent: EtOAc/hexane=4/6; 6/4; 1/0; about 150 ml for each fraction). The chromatography furnished an additional 3.55 g of desired product (yield 17.5%), and 0.5252 g of impure product (yield 2.5%). Therefore, the total yield was close to 80%. MS: 584.5 (M+1). $^1$H-NMR, CDCl$_3$, δ: 7.46 (d, 1H, propenyl), 6.06 (d, 1H, propenyl), 4.97 (d, 1H, position 1 on the sugar ring), 4.60 (m, 1H, propenyl), 4.18 (m, 1H, position 2 on the ring), 3.85-3.50 (m), 3.40 (s, 2H, CH$_2$ between two carbonyls), 2.7 (1H, OH), 2.50 (t, 2H, CH$_2$ adjacent to carbonyl), 1.6 (d, 3H, CH$_3$ of propenyl), 1.6-1.4 (m, 4H CH$_2$ on side chains), 1.25 (bs, many CH$_2$ on side chains), 0.85 (t, 6 H, 2 methyls of the side chains). The first five fractions (fraction 1-5, EtOAc/hexane=2/1, Rf 0.9) obtained from the chromatography produced 8.28 g of white crystals. [This amount is equivalent to 41.74 mmol. This indicates that 60% (41.74 mmol/69.73 mmol=59.86%) of 3-Oxo-tetradecanoic acid did not have chance to react with compound 9. The yield of the preparation could be increased simply by adding 3-Oxo-tetradecanoic acid in batches and adjusting the reaction temperature]. $^1$H-NMR proved it to be undecyl methyl ketone, which was generated from the reagent MV 128 through decarboxylation.

Step 5: Preparation of Compound 11

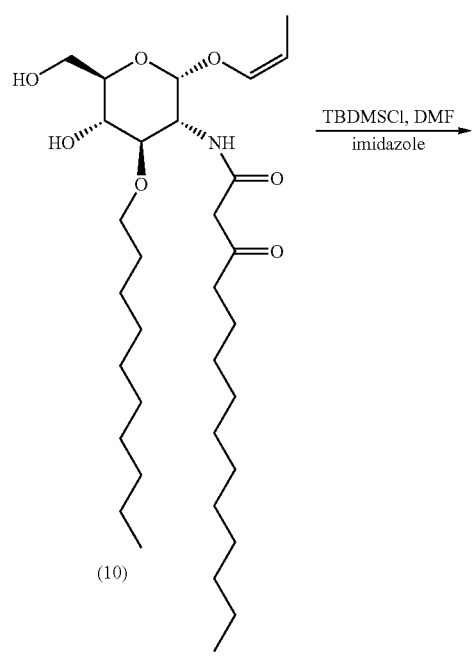

Anhydrous pyridine (3.6 ml, 44.6 mmol, 11 eq.) was injected into a mixture of compound 10 (2.3622 g, 4.049 mmol, 1 eq.) and TBDMS-Cl (811 mg, 5.39 mmol, 1.33 eq.) at room temperature with stirring. The mixture turned cloudy in a couple of minutes due to the precipitation of the pyridine hydrochloride. After 2 hours, the reaction was complete, and the reaction mixture was partitioned between ethyl acetate and brine. The organic phase was washed, dried, and concentrated to give 2.882 g (101.9% yield) of crude product weighed. Rf 0.38 (silica gel, EtOAc/hexane=1/4). $^1$H-NMR, CDCl$_3$, δ: 7.30 (d, 1H, amide), 6.0 (d, 1H, propenyl), 4.95 (d, 1H, position 1 on the sugar ring), 4.55 (m, 1H, propenyl), 4.13 (m, 1H, position 2 on the ring), 3.85-3.45 (3 groups of m), 3.35 (s, 2H, CH$_2$ between two carbonyls), 2.95 (bs, 1H, OH), 2.45 (t, 2H, CH$_2$ adjacent to carbonyl), 1.60 (d, 3H, propenyl), 1.5 (m, CH$_2$ on the side chain), 1.20 (bs, many CH$_2$ on the two side chains), 0.84 (m, 5 methyls), 0 (s, 2 methyls of TBDMS).

Step 6: Preparation of Compound 12

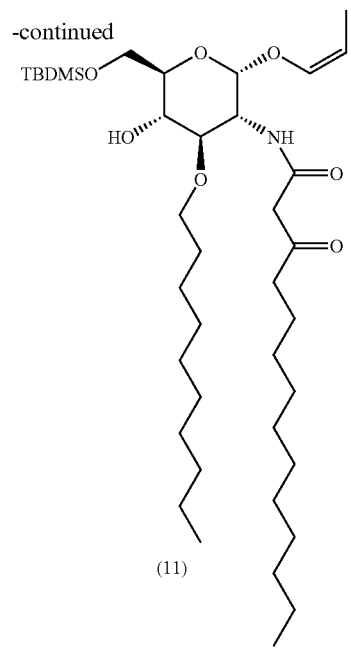

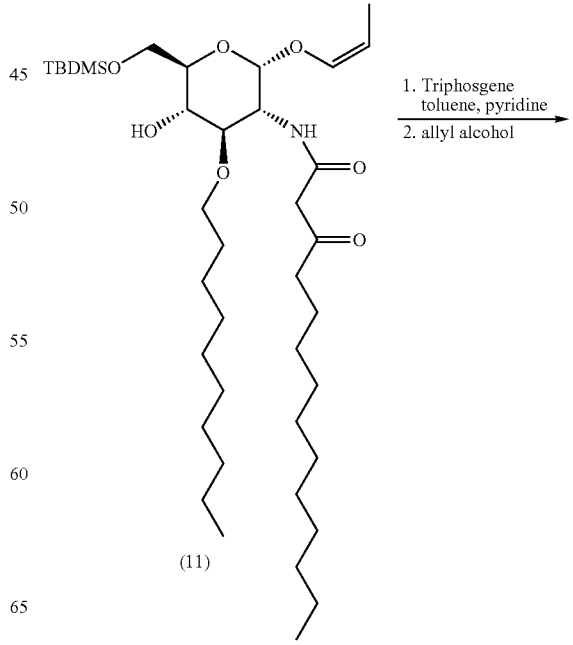

Step 7: Preparation of Compound 13

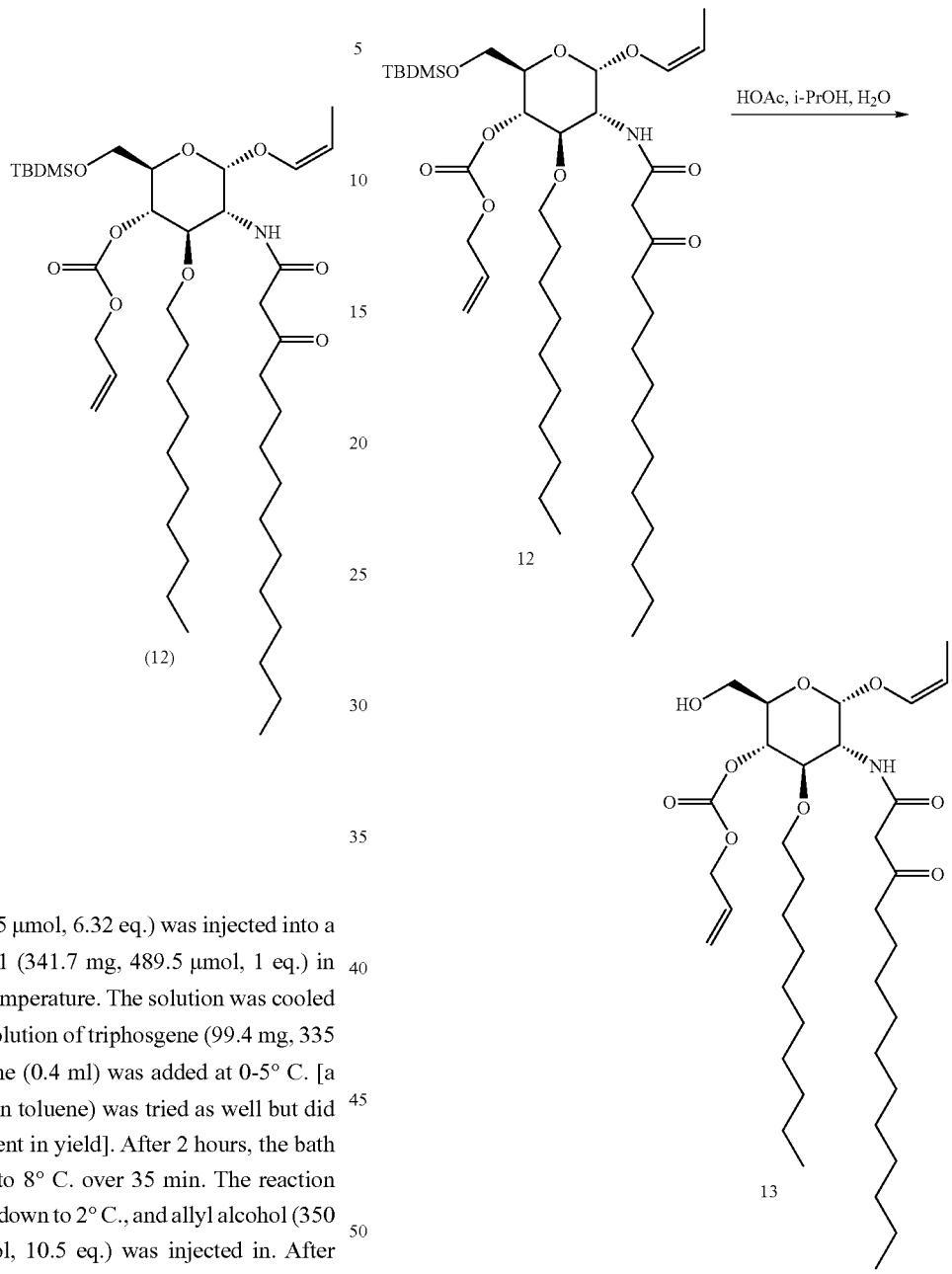

Pyridine (250 ml, 3095 µmol, 6.32 eq.) was injected into a solution of compound 11 (341.7 mg, 489.5 µmol, 1 eq.) in toluene (1 ml) at room temperature. The solution was cooled in an ice/water bath. A solution of triphosgene (99.4 mg, 335 µmol, 2.05 eq.) in toluene (0.4 ml) was added at 0-5° C. [a 20& phosgene solution in toluene) was tried as well but did not show any improvement in yield]. After 2 hours, the bath temperature was raised to 8° C. over 35 min. The reaction mixture was then cooled down to 2° C., and allyl alcohol (350 µL, 298 mg, 5,150 µmol, 10.5 eq.) was injected in. After stirring for 40 minutes, the bath temperature was raised to 16° C., and the reaction mixture was stirred at 10° C. for 2.5 hours. The reaction mixture was quenched with aqueous $NaHCO_3$, and was partitioned between ethyl acetate and brine. The organic phase was washed with water, dried and evaporated to give 395.4 mg of crude product. Its TLC looked like only one spot (silica gel, EtOAc/Hexane=1/4, Rf, 0.48). 143.8 mg (36.4% of the total) of the crude product was chromatographed (silica gel 9.87 g, solvent EtOAc/hexane=1/6, isocratic). The desired product 12 was obtained in 62% yield (86.6 mg), along with 22.9 mg (18.4%) of starting material. Total corrected yield: 77%.

Removal of the TBDMS protecting group may be effected by treating saccharide 12 with HOAc in $iPrOH/H_2O$. An exemplary synthesis is described below:

Compound 12 (3.766 kg) was dissolved in i-Pr (3.95 kg) and Glacial Acetic acid (14.16 kg) in a 50-L reactor with stirring. To the reaction mixture was added process water (5.04 kg) and the stirring was continued at room temperature until the reaction was completed. The reaction was monitored by HPLC (TM-150). The aliquots taken were either a clear or a slightly cloudy yellow solution with particles visible. The aliquots were treated before HPLC analyses. A 1 mL portion of the aliquot for HPLC analysis was first mixed with 0.5 mL of HPLC grade THF to give a clear solution with particles still visible. Portion (0.1 mL) of the resulting THF mixture was mixed with HPLC grade MeCN (0.9 mL), was filtered through 0.45 μm syringe filter, and was then subjected to HPLC analysis. Typically, after 92 hours and 5 minutes of stirring, the ratio [cyclized biproduct]/13/12 was 1.1/91.2/7.7. The ratio was 1.9/96.5/1.6 after 115 hours and 5 minutes of stirring. After stirring for 120.25 hours, the resulting yellow cloudy reaction mixture was filtered through Celite (1.01 kg, pretreated with 3.5 kg of a 9.69/1.81/2.19 w/w/w mixture of Glacial Acetic acid/2-PrOH/process water) and 5 kg of a 9.69/1.81/2.19 mixture of 9.69/1.81/2.19 w/w/w mixture of Glacial Acetic acid/2-PrOH/process water to give 30.5 kg of a clear orange solution. [Note: The ratio of [cyclized biproduct]/13/12 was 1.7/97.2/1.1 right after filtration. It was 2.1/97.5/0.4 after overnight (17 hours) at room temperature, and 2.5/97.4/0.12 after another 24 hours (from the second half of the filtrate). In the meantime, the color and clarity of the substrate was substantially the same.] The filtrate was divided into two equal portions for isolation of Compound 13.

Process water (18 kg) in a 50 L reactor was cooled to 0.9° C. with stirring. Half of the filtrate containing compound 13 was added to the cold water with moderate stirring and the reaction temperature was kept below 8° C. [Note: the addition was carried out with a metering pump. The addition took about 25 minutes.] The resulting mixture was stirred for 25 minutes while maintaining the reaction temperature between 5 and 10° C. Compound 13 was collected in a Nutsche filter and the resulting solid was washed with process water. [Note: isolation of the first half of compound 13 was carried out in a centrifuge first. During the process, a milky filtrate was collected but the solid was washed with 10.0 kg of 10° C. process water anyway. At the end, it was discovered that the bag contained solid compound 13 and large quantities of water. Attempts to process the material in the bad in a Nutsche filter with either one or two filter papers failed because the filter paper(s) ruptured under vacuum. At the end, a polypropylene mesh was put under a filter paper to support the filter paper and vacuum filtration of the material from the bag was completed. The filtration was extremely slow. A Buchner funnel was also used to speed up the process. The solid in the Buchner funnel was washed with 12 kg of process water and was then transferred to the Nutsche filter. The combined solid was washed with 2 kg of process water. The solid was left in the Nutsche filter overnight (14.75 h) with vacuum applied and a nitrogen gas stream delivered to the top of the filter.] After overnight drying (14.75 hours) in the filter, the solid was transferred to a tumble drier and dried under vacuum with occasional turning. [Note: the ratio of [cyclized biproduct]/13/12 was 2.0/97.7/0.3 before drying in the tumble drier. The ratio is about the same as that of the filtrate before isolation of the second half of compound 13 (2.1/97.5/0.4).].

Isolation for the second half of compound 13 proceeded much smoothlier. Process water (18 kg) was cooled to 0.9° C. in a 50 L reactor. The remaining half of the filtrate containing compound 13 from the Celite filtration was added to the cold water with stirring while maintaining the temperature between 5 and 10° C. Compound 13 was collected in a Nutsche filter under vacuum and the solid was washed with 5.07 kg of cold (10° C.) process water and then with 5.1 kg of process water. The material was left in the Nutsche filter overnight (19 hours) with vacuum applied at the bottom and a stream of nitrogen gas applied on the top. The resulting solid was added to the tumble drier containing the first half of compound 13. The combined material was dried under vacuum for another 5 days to give 2.75 kg (82.8% actual yield) of desired product 13 as an off-white solid.

Alternatively, deprotection may be effected by treatment of compound 12 with HF in a suitable solvent (e.g., $CH_2CH_2$). An exemplary procedure is as follows:

To a solution of 48% aqueous hydrofluoric acid, 11 mL, in acetonitrile 293 mL, was added 4.6 g of silica gel, followed by a solution of saccharide 12, 146.7 g, in methylene chloride, 147 mL. After one half-hour, the mixture was diluted with water, 975 mL, and extracted with methylene chloride. The organic layer was separated and the aqueous layer re-extracted with methylene chloride. The combined organic layers were washed with aqueous sodium bicarbonate solution, dried, and the solvent was removed under reduced pressure. The residue was chromatographed on silica Gradient elution (hexane:ethyl acetate 5:1 to 0:1) gave 110.4 g of an off-white waxy solid.

Alternatively, removal of the TBDMS protecting group may be effected with TBAF.

Example 4

Alternative Exemplary Preparation of B1287 Right-Hand Fragment (13)

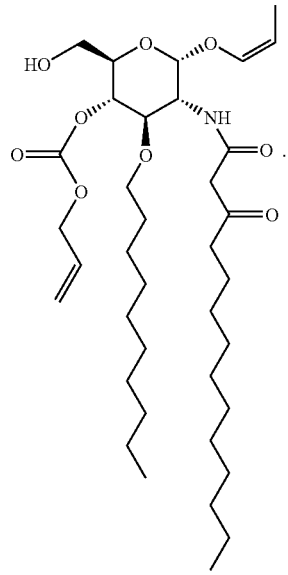

Step 1: Preparation of Compound 19

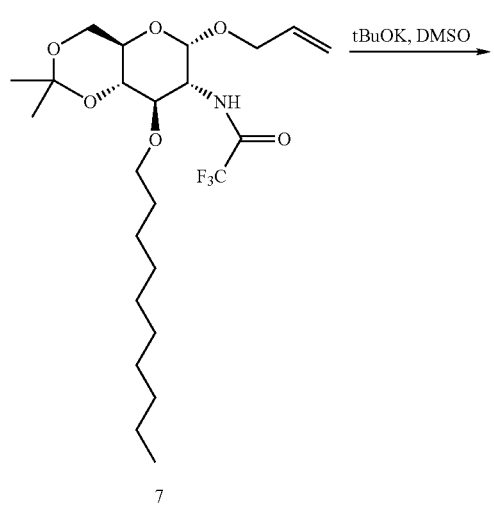

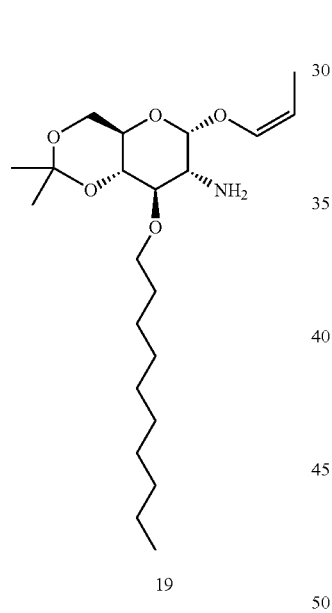

This reaction may be carried out in a similar fashion as for the preparation of compound 9 in example 3 above. An exemplary procedure is as follows:

To a suspension of potassium t-butoxide in DMSO may be added a solution of saccharide 8 in DMSO. The mixture may be heated to 85° C. for $1^{1/4}$ hour and 3 M aqueous potassium hydroxide may be added with overnight stirring at 85° C. The mixture may then be cooled to room temperature and poured onto a mixture of brine and water. The mixture may be extracted with methylene chloride. The combined organic extracts may be dried over a suitable drying agent (e.g., MgSO$_4$), and the solvent may be removed under reduced pressure. Chromatographic separation on silica should give the desired product 19 in good yield.

Step 2: Preparation of Compound 20

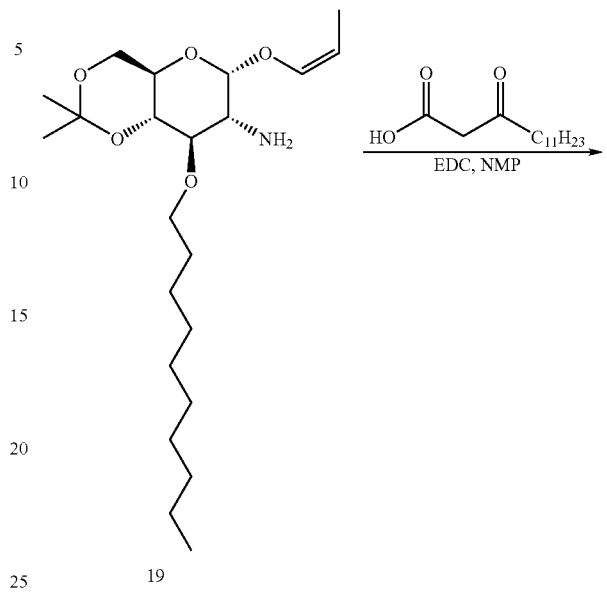

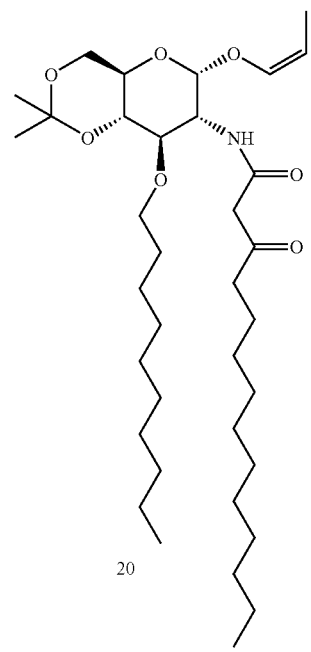

The reaction may be effected as follows:

To an ice-cold solution of amino sugar 19 in methylene chloride can be added 1-(3-dimethylaminopropyl)-3-ethyl-carbodiimide hydrochloride (EDC) followed in 10 minutes by the carboxylic acid. After 10 minutes, the mixture can be extracted with saturated aqueous sodium bicarbonate. The organic layer can be separated, the aqueous layer re-extracted with methylene chloride, the combined organic layers dried, and the solvent can be removed under reduced pressure. Chromatographic separation on silica should give the desired product 20 in good yield.

143
Step 3: Preparation of Compound 10

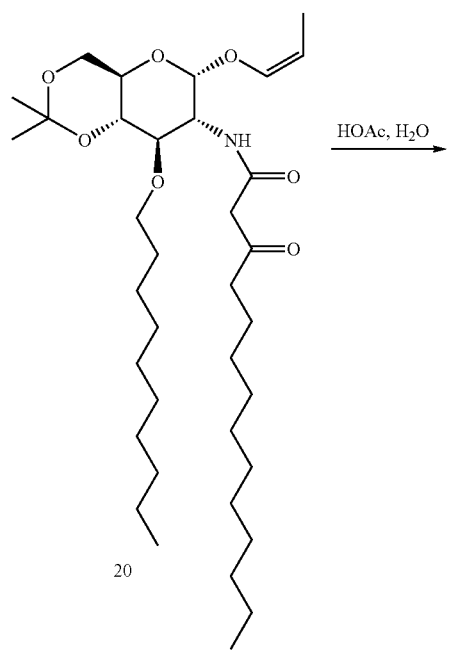

This reaction may be carried out in a similar fashion as for the preparation of compound 8 in example 3 above. An exemplary procedure is as follows:

A solution of saccharide 20 in a mixture of glacial acetic acid and water may be stirred overnight. The reaction mixture may be poured into water and filtered. The filtrate may be dried by azeotropic distillation with toluene under reduced pressure to give the desired compound 10 in good yield.

144
Step 4: Preparation of Compound 11

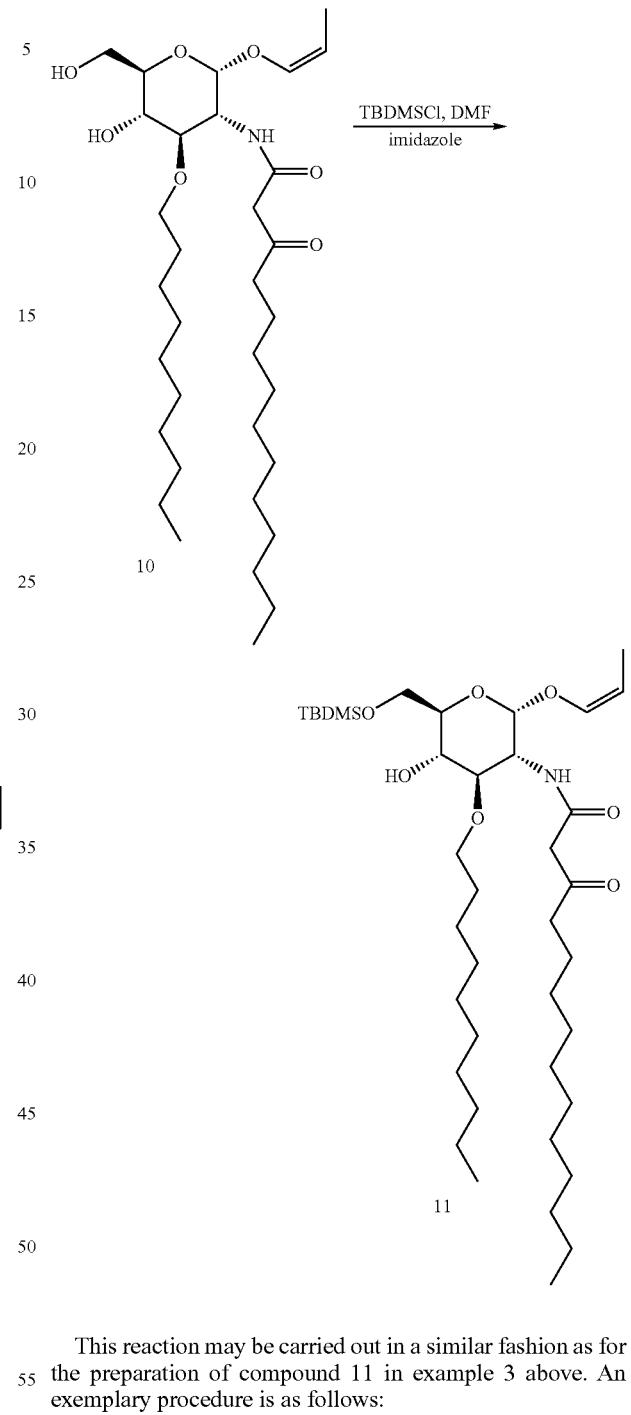

This reaction may be carried out in a similar fashion as for the preparation of compound 11 in example 3 above. An exemplary procedure is as follows:

Anhydrous pyridine (3.6 ml, 44.6 mmol, 11 eq.) was injected into a mixture of compound 10 (2.3622 g, 4.049 mmol, 1 eq.) and TBDMS-Cl (811 mg, 5.39 mmol, 1.33 eq.) at room temperature with stirring. The mixture turned cloudy in a couple of minutes due to the precipitation of the pyridine hydrochloride. After 2 hours, the reaction was complete, and the reaction mixture was partitioned between ethyl acetate and brine. The organic phase was washed, dried, and concentrated to give 2.882 g (101.9% yield) of crude product weighed. Rf: 0.38 (silica gel, EtOAc/hexane=1/4). $^1$H-NMR, CDCl$_3$, δ: 7.30 (d, 1H, amide), 6.0 (d, 1H, propenyl), 4.95 (d, 1H, position 1 on the sugar ring), 4.55 (m, 1H, propenyl), 4.13 (m, 1H, position 2 on the ring), 3.85-3.45 (3 groups of m), 3.35 (s, 2H, $CH_2$ between two carbonyls), 2.95 (bs, 1H, OH), 2.45 (t, 2H, $CH_2$ adjacent to carbonyl), 1.60 (d, 3H, propenyl), 1.5 (m, $CH_2$ on the side chain), 1.20 (bs, many $CH_2$ on the two side chains), 0.84 (m, 5 methyls), 0 (s, 2 methyls of TBDMS).

Step 5: Preparation of Compound 12

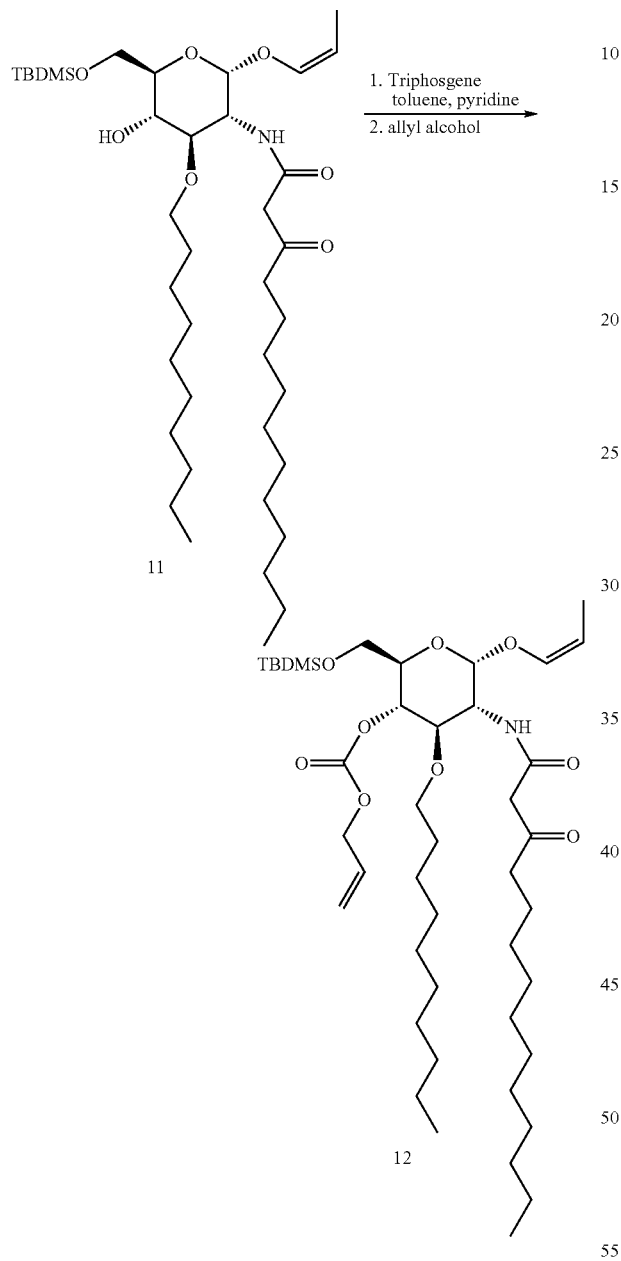

This reaction may be carried out in a similar fashion as for the preparation of compound 11 in example 3 above. An exemplary procedure is as follows:

Pyridine (250 ml, 3095 µmol, 6.32 eq.) was injected into a solution of compound 11 (341.7 mg, 489.5 µmol, 1 eq.) in toluene (1 ml) at room temperature. The solution was cooled in an ice/water bath. A solution of triphosgene (99.4 mg, 335 µmol, 2.05 eq.) in toluene (0.4 ml) was added at 0-5° C. [a 20& phosgene solution in toluene) was tried as well but did not show any improvement in yield]. After 2 hours, the bath temperature was raised to 8° C. over 35 min. The reaction mixture was then cooled down to 2° C., and allyl alcohol (350 µL, 298 mg, 5,150 µmol, 10.5 eq.) was injected in. After stirring for 40 minutes, the bath temperature was raised to 16° C., and the reaction mixture was stirred at 10° C. for 2.5 hours. The reaction mixture was quenched with aqueous $NaHCO_3$, and was partitioned between ethyl acetate and brine. The organic phase was washed with water, dried and evaporated to give 395.4 mg of crude product. Its TLC looked like only one spot (silica gel, EtOAc/Hexane=1/4, Rf, 0.48). 143.8 mg (36.4% of the total) of the crude product was chromatographed (silica gel 9.87 g, solvent EtOAc/hexane=1/6, isocratic). The desired product 12 was obtained in 62% yield (86.6 mg), along with 22.9 mg (18.4%) of starting material. Total corrected yield: 77%.

Step 6: Preparation of Compound 13

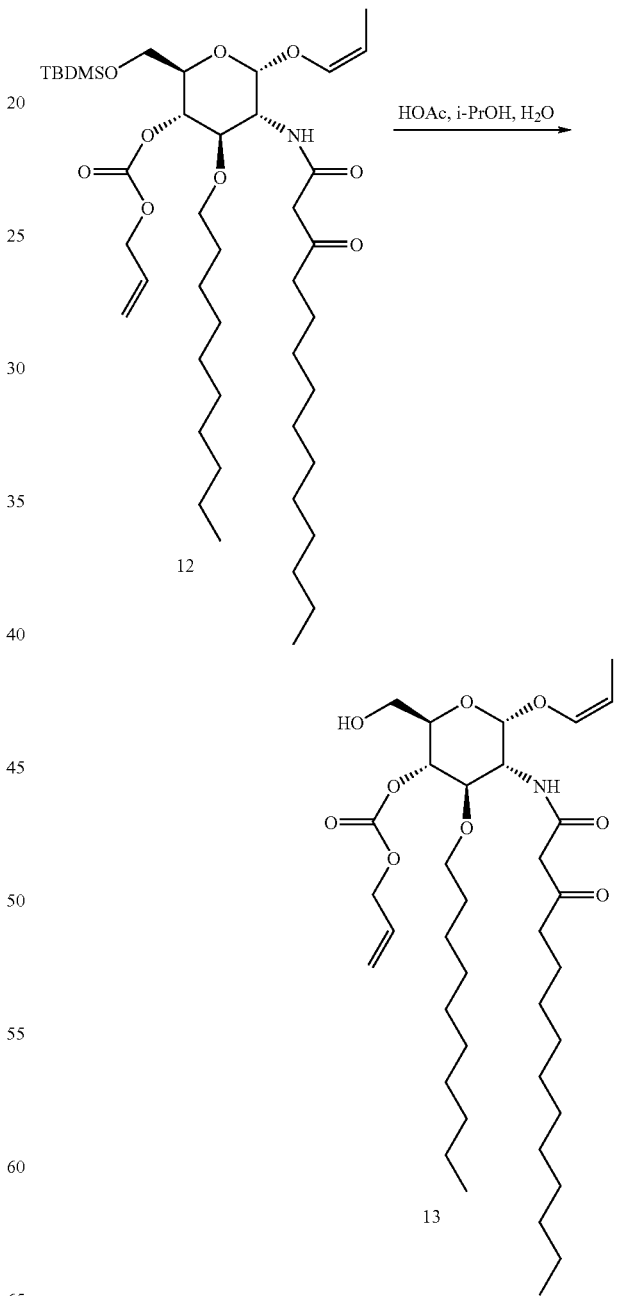

Removal of the TBDMS protecting group may be effected by treating saccharide 12 with HOAc in iPrOH/H$_2$O.

Alternatively, deprotection may be effected by treatment of compound 12 with HF in a suitable solvent (e.g., CH$_2$Cl$_2$). An exemplary procedure is as follows:

To a solution of 48% aqueous hydrofluoric acid, 11 mL, in acetonitrile 293 mL, was added 4.6 g of silica gel, followed by a solution of saccharide 12, 146.7 g, in methylene chloride, 147 mL. After one half-hour, the mixture was diluted with water, 975 mL, and extracted with methylene chloride. The organic layer was separated and the aqueous layer re-extracted with methylene chloride. The combined organic layers were washed with aqueous sodium bicarbonate solution, dried, and the solvent was removed under reduced pressure. The residue was chromatographed on silica. Gradient elution (hexane:ethyl acetate 5:1 to 0:1) gave 110.4 g of an off-white waxy solid.

Alternatively, removal of the TBDMS protecting group may be effected with TBAF.

Example 5

Exemplary Preparation of B1287

Step 1: Preparation of Compound 14

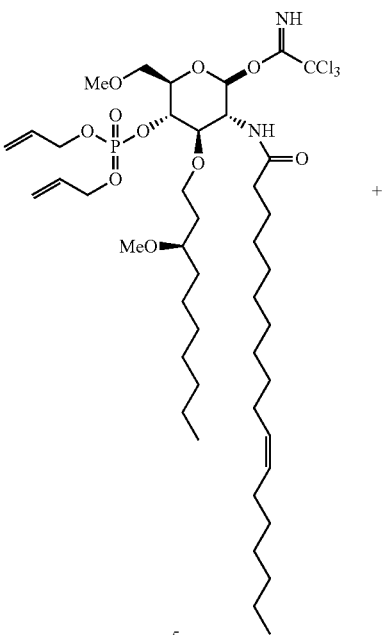

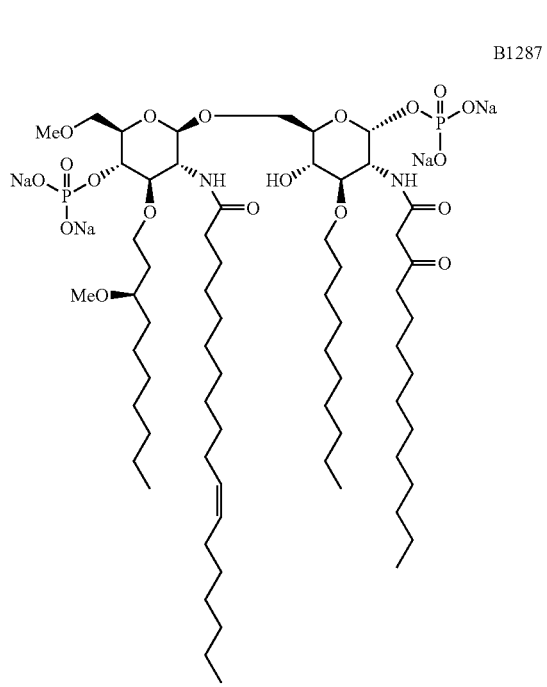

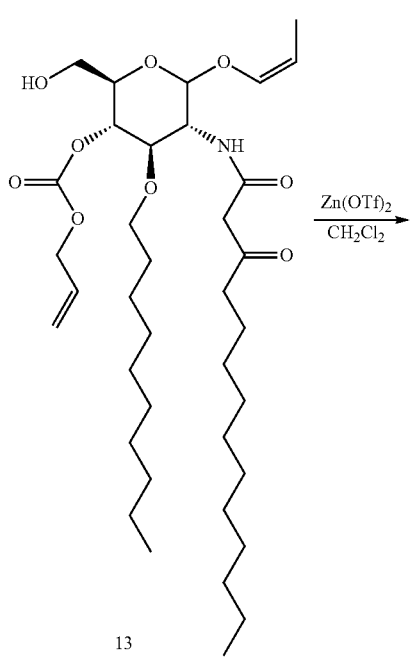

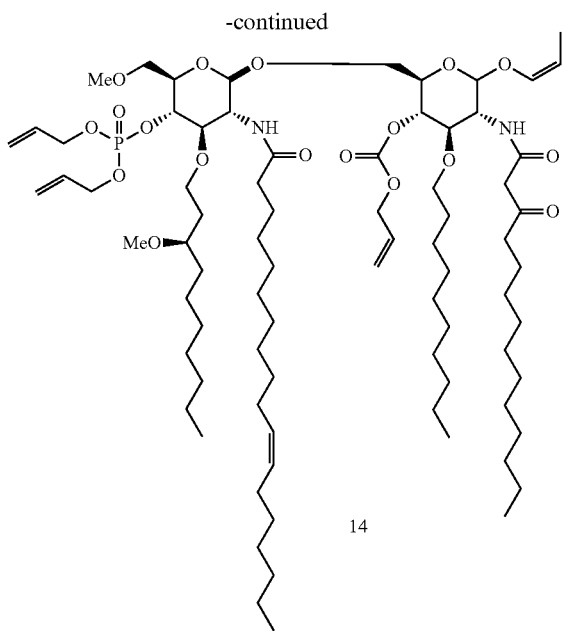

14

The coupling reaction may be carried out using Zn(OTf)$_2$. An exemplary procedure is as follows:

Zinc trifluoromethanesulfonate (0.060 kg) was weighed out in a dry-box into a new clean 3 L flask fitted with a mechanical stirrer and nitrogen gas inlet The flask was placed in a hood and acetonitrile (anhydrous, 1.04 kg) was added to the flask. This was stirred at room temperature until the solid completely dissolves (at least 30 minutes). Meanwhile, compound 13 (3.42 kg, 97.6%, 5.0 moles) was charged to a cleaned 50 L reactor rinsed with methylene chloride and flushed with nitrogen. After inserting the reactor, methylene chloride (anhydrous, 15.22 kg) was added and this was stirred until the solid dissolved. The solution of Zn(OTf)$_2$ in Acetonitrile was added to the reactor. Acetonitrile (0.35 kg, anhydrous) was used to rinse the reactor, and the rinse was added to the reaction mixture. A solution of compound 5 (7.44 kg, 83% wt/wt, 7.33 moles) in methylene chloride (anhydrous, 7.40 kg) was prepared. [Note: the initial assay completed on the kilo lab batch of 5 was reported as 83% wt/wt. After a data review, it was found that only the major alfa anomer was included in this assay. Stoichiometry for the coupling reaction was based on assay that combines both anomers. Therefore, the amount of 5 used in this coupling was 10 to 15% higher than anticipated.] The solvent was added to the oily product in a rotary evaporator bulb and the bulb was rotated until the oil dissolved. This solution was added to the 50 L reactor over 135 minutes using a small Teflon metering pump. Reaction temperature remained between 16 and 18° C. throughout the addition. The equipment and metering pump were rinsed with methylene chloride (anhydrous, 2.0 kg). A sample was removed and analyzed by HPLC. [Note: Sample preparation is to dissolve enough reaction mixture to give about 5 mg of compound 14/mL of acetonitrile. The sample was analyzed using test method TM-450. TLC was also used to monitor the reaction. The TLC solvent system used was 50% ethyl acetate/hexanes. The stationary phase was High Performance Silica Gel plates made by E. Merck. Spots were visualized by charring a plate dipped in p-anisaldehyde/sulfuric acid.] The amount of unreacted 13 was 0.32 area % (target <1%), so the reaction was worked-up. First, the reaction mixture was transferred to a 100 L reactor. The equipment and pump were rinsed with methylene chloride (ACS, 8.9 kg). A sodium chloride/sodium bicarbonate solution (1.06 kg NaCL, ACS plus 0.64 kg NaHCO$_3$, ACS plus 22.0 kg process water) was added slowly to prevent excess foaming. Process water (2.0 kg) was used to rinse the equipment. After stirring for 10 minutes, methanol (ACS, 8.4 kg) was added. This was stirred for 10 to 15 minutes, agitation was stopped and the solution was allowed to settle for 20 to 30 minutes. The bottom organic layer was removed, followed by the top aqueous solution (pH 9 to 10, strip). After charging the top organic layer to the reactor, the equipment was washed with methylene chloride (ACS, 5.0 kg). A solution of 5% sodium bicarbonate (17.1 process water plus 0.88 kg sodium bicarbonate) was added, followed by methanol (ACS, 11.4 kg). After stirring and settling, the bottom organic layer was drained into a clean, tared vessel. The total weight of the organic layer was 42.7 kg, which was sample and found to contain 11.5% wt/wt of desired compound 14 (4.9 kg, 72.7% yield). The top aqueous layer was drained and the pH measured as 7 (strip). The organic layer was transferred from the vessel to a 100 L reactor and the equipment was rinsed with methylene chloride 92.2 kg). Solvents were removed under vacuum (jacket set at 30 to 35° C. and full house vacuum) to give crude 14 as a thick paste. Methanol (ACS, 39.4 kg) was charged and the solution was cooled to −2 to 2° C. over 35 minutes. Process water (7.46 kg) was added slowly over 70 minutes using a metering pump. After stirring the suspension for one hour at −2 to 2° C., the solid was filtered using a centrifuge in two loads. Each load was washed twice with −20° C. methanol/water (85/15), 15.1 kg. A white solid (13.08 kg) was loaded into a tumble dryer and was dried at full house vacuum (22 to 23° C.). The product went from a tacky white solid to a yellow heterogenous clumpy solid. Most of the product was eventually scraped off the dryer to give 6.25 kg of solid. The material stuck to the walls was dissolved in THF (5.4 kg, then 5.3 kg). This was concentrated to dryness on a rotary evaporator to give 0.56 kg of oil. In order to get a homogeneous sample of 14 to determine the yield, the 6.25 kg and 0.56 kg were dissolved in THF (15 kg and 3.0 kg respectively). Solvents were removed by vacuum distillation (bath 20 to 22° C., full house vacuum) using a rotary evaporator. Additional THF (15.3 kg) was added to the oil, which was concentrated to dryness under vacuum (bath 20 to 22° C., full house vacuum). The final product weight was 9.21 kg. This was sampled top, middle and bottom for wt/wt % of 14. The results showed large variability (4 to 27%) in the level of THF, so an isolated product yield was not determined.

Alternatively, the coupling reaction may be carried out using AgOTf. An exemplary procedure is as follows:

To a suspension of monosaccharide 5 (12.32 g) and monosaccharide 13 (4.14 g) in toluene (8.28 mL) and heptane (8.28 mL) was added methanesulfonic acid (0.25 mL). The mixture was stirred vigorously under nitrogen atmosphere for 19 hr at 25° C. The reaction mixture was dissolved in ethyl acetate (300 mL) and the resulting organic mixture was washed with water (300 mL), saturated aqueous sodium bicarbonate (150 mL) and 10% brine (300 mL). The organic layer was separated and concentrated under reduced pressure to give crude product (17.89 g). The crude product (5 g) was dissolved in methanol (65 mL). Water (5.4 mL) was added and the mixture was stirred for 1.5 hr at −25° C. The resulting precipitate was collected by filtration and was dried under high vacuum to give the desired disaccharide 14 (2.45 g) as a yellowish white powder.

Step 2: Preparation of Compound 15

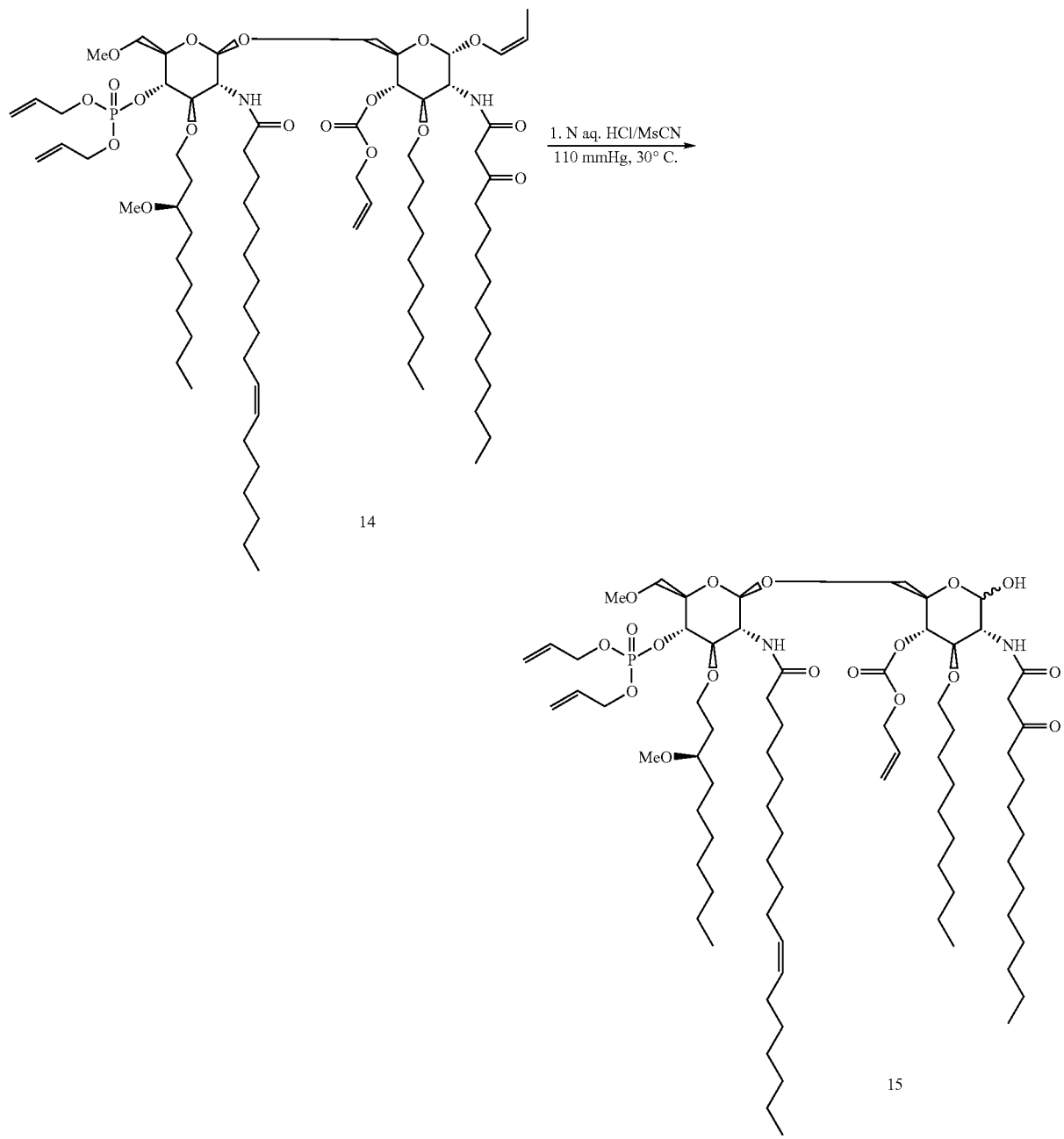

A toluene solution of 14 (68.7 kg) was charged to a 400 L reactor and the solvent was evaporated under full vacuum. [Notes: The quality of 14/toluene solution was 11.44 w/w % purity, 94.7 area % purity, 0.02% water content. Toluene (4.6 kg) was used to rinse residual amounts of 14 into the bulb. The jacket temperature was between 46.4° C. and 20.6° C.) Acetonitrile (28.3 kg) was charged to the reactor and solvent evaporation continued. After the first acetonitrile charge, the toluene content of the liquid phase from the resulting suspension was 29.4 w/w % and the acetonitrile content was 55.1 w/w %. During the first chase, the jacket temperature was between 24.2° C. and 45.6° C. The acetonitrile chase (28.3 kg) was repeated. After the second acetonitrile charge, the toluene content of the liquid phase from the resulting suspension was 12.2 w/w % and the acetonitrile content was 78.5 w/w %. During the second chase, the jacket temperature was between 45.6° C. and 26.3° C. Acetonitrile (28.2 kg) was added to the residue in the bulb and the mixture was well stirred to give a suspension. After the third acetonitrile charge, the toluene content of the liquid phase from the resulting suspension was 4.8 w/w % and the acetonitrile content was 7.76 w/w %. Aqueous 1 N HCl was added, the reaction pressure was reduced, heating was applied, ad the distillate was collected in a 200 L reactor. The reaction condition are listed below:

| Time (min) | Pressure | Reaction Temperature | Jacket Temperature | Total Solvent Distilled out |
|---|---|---|---|---|
| 0 | Start | 27.0° C. | 35.1° C. | 0 |
| 30 | 116 mmHg | 30.9° C. | 35.1° C. | About 2 L |
| 42 | Sampling | 34.9° C. | 34.9° C. | About 3 L |
| 72 | 113 mmHg | 30.8° C. | 35.0° C. | About 10 L |
| 82 | 200 mmHg | 31.6° C. | 35.0° C. | About 10 L |

The reaction was monitored by HPLC, and was determined to be complete after 1 hour 12 minutes of heating. HPLC analysis results are tabulated below:

| Time (min) | (α- + β-15)/14 | α-15/β-15 |
|---|---|---|
| 42 | 95.1/4.9 | 87.5/12.5 |
| 72 | 98.7/1.3 | 87.0/13.0 |

After the reaction was compete, most of the solvent was evaporated under full vacuum (jacket temperature: 35.1° C.; the volume of the reaction mixture was reduced down to 20 L). Toluene (10.6 kg) was added to dissolve the organic material. Eight percent aqueous sodium bicarbonate solution was added to adjust the pH value of the reaction mixture to between 6 and 9 (the pH value of the organic phase was 8-9, as indicated by wet pH paper). The solvent was evaporated under full vacuum, and the residue was chased with toluene (2×28.0 kg) to reduce water content to 0.5%. After each chase, an aliquot was analysed for α-15/β-15 ratio and water content. The results are tabulated below:

| Toluene solution | α-15/β-15 | Water content |
|---|---|---|
| After first 28.0 kg toluene addition | 87.5/12.5 and 89.0/11.0 from two tests | Not measured |
| After second 28.0 kg toluene addition | 89.6/10.4 | 0.055% |

The resulting mixture was filtered through Celite [Celite 545 (2.1 kg) was rinsed with 4.5 kg of toluene before use]. Toluene was used to rinse the residual product out of Celite and the filtrate and the four rinses were combined. The batch produced 54.4 kg toluene solution of 15 (74.0% actual yield of α-15) as a brown liquid.

Alternatively, the reaction may be carried out using HF in a suitable solvent (e.g., acetonitrile). An exemplary procedure is as follows:

A solution of disaccharide 14, 161.3 g, in methylene chloride, 215 mL, in a Teflon bottle was added to a solution of 48% hydrofluoric acid, 150 mL, in acetonitrile, 474 mL. After four hours, the mixture was poured onto 500 mL of water. The mixture was extracted twice with methylene chloride. The combined organic layers were washed with aqueous saturated sodium bicarbonate, dried, and the solvent was removed under reduced pressure. The residue was chromatographed on silica. Gradient elution (methylene chloride:ethyl acetate:methanol 500:500:20 to 500:500:160) gave a yellow waxy gum.

Step 3: Preparation of Compound 16

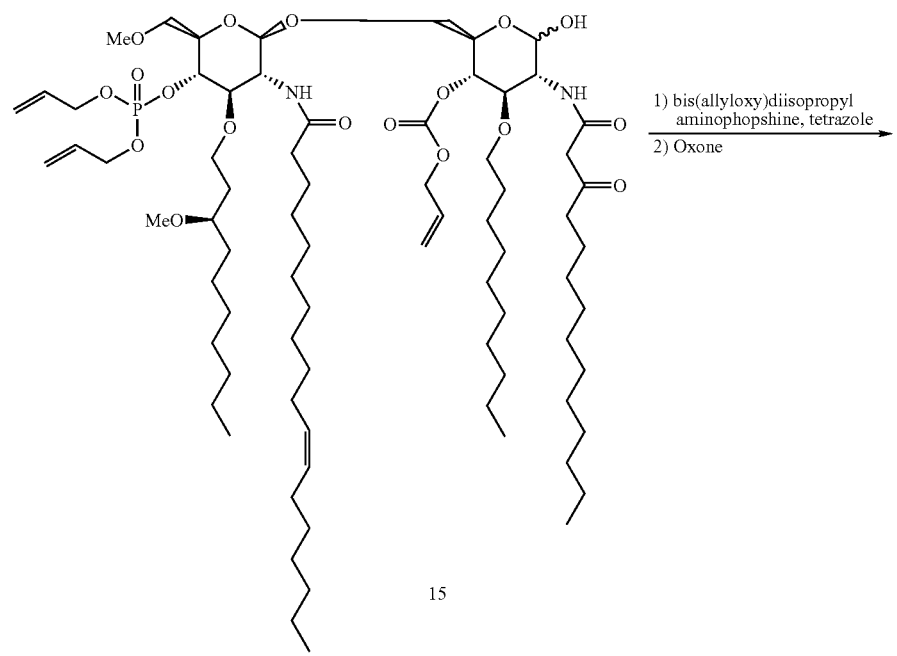

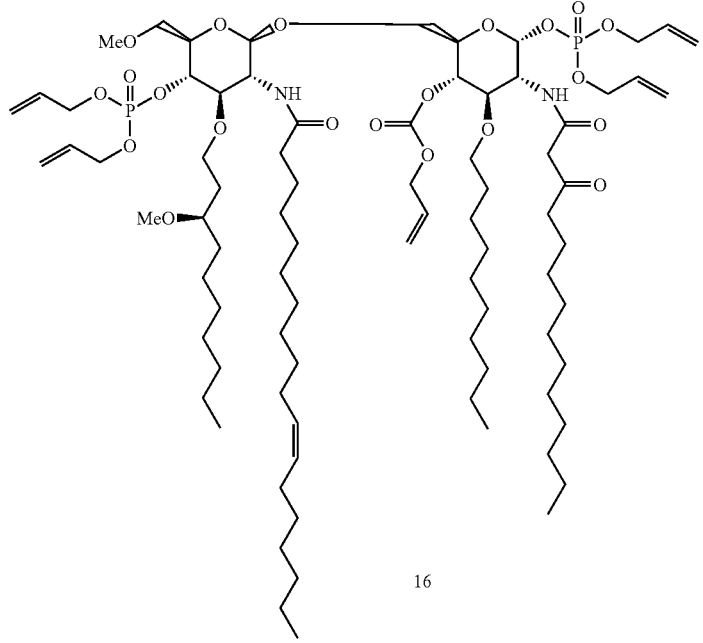

16

Disaccharide 15, 719 mg, was dissolved in methylene chloride and sodium sulfate (1.4 g) was added. Diallyldiisopropylphosphoramidite (189 µL) and tetrazole (162 mg) were added, the mixture stirred for 10 minutes, and then cooled to −78° C. A solution of m-chloroperoxybenzoic acid (192 mg) in methylene chloride (4 mL) was added dropwise. The mixture was washed with aqueous sodium thiosulfate and with aqueous sodium bicarbonate, dried (sodium sulfate), and the solvent removed under reduced pressure; The residue was chromatographed to give 660 mg.

Step 4: Preparation of B1287

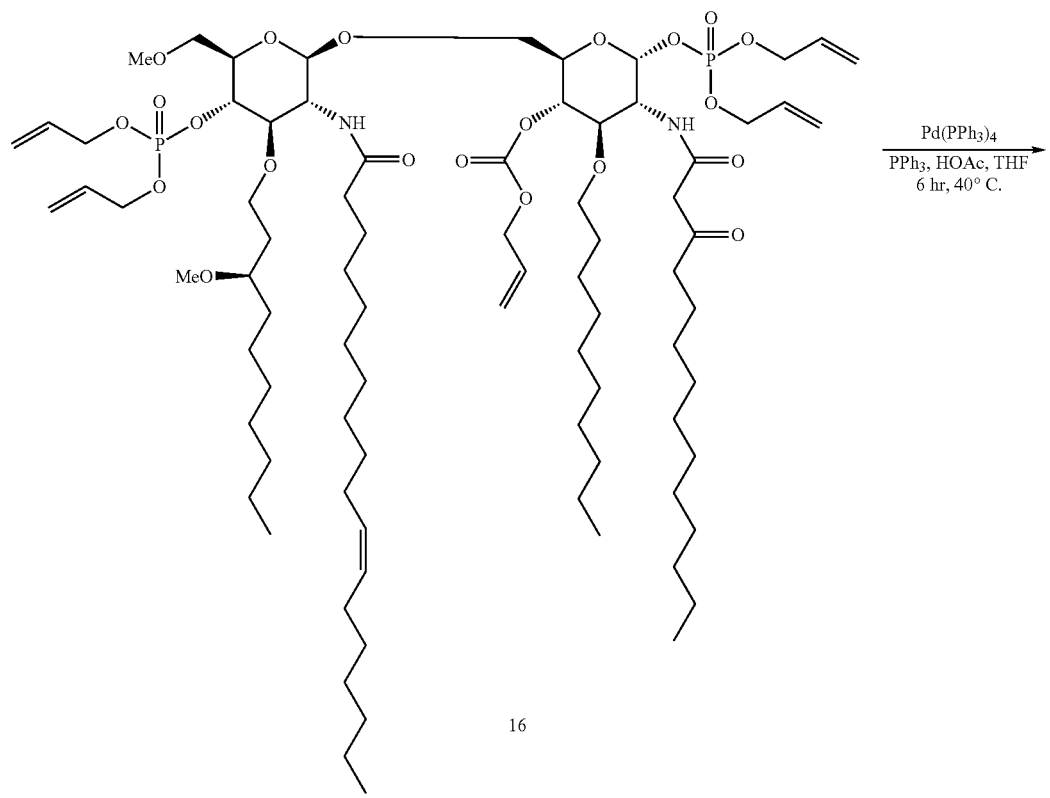

16

-continued

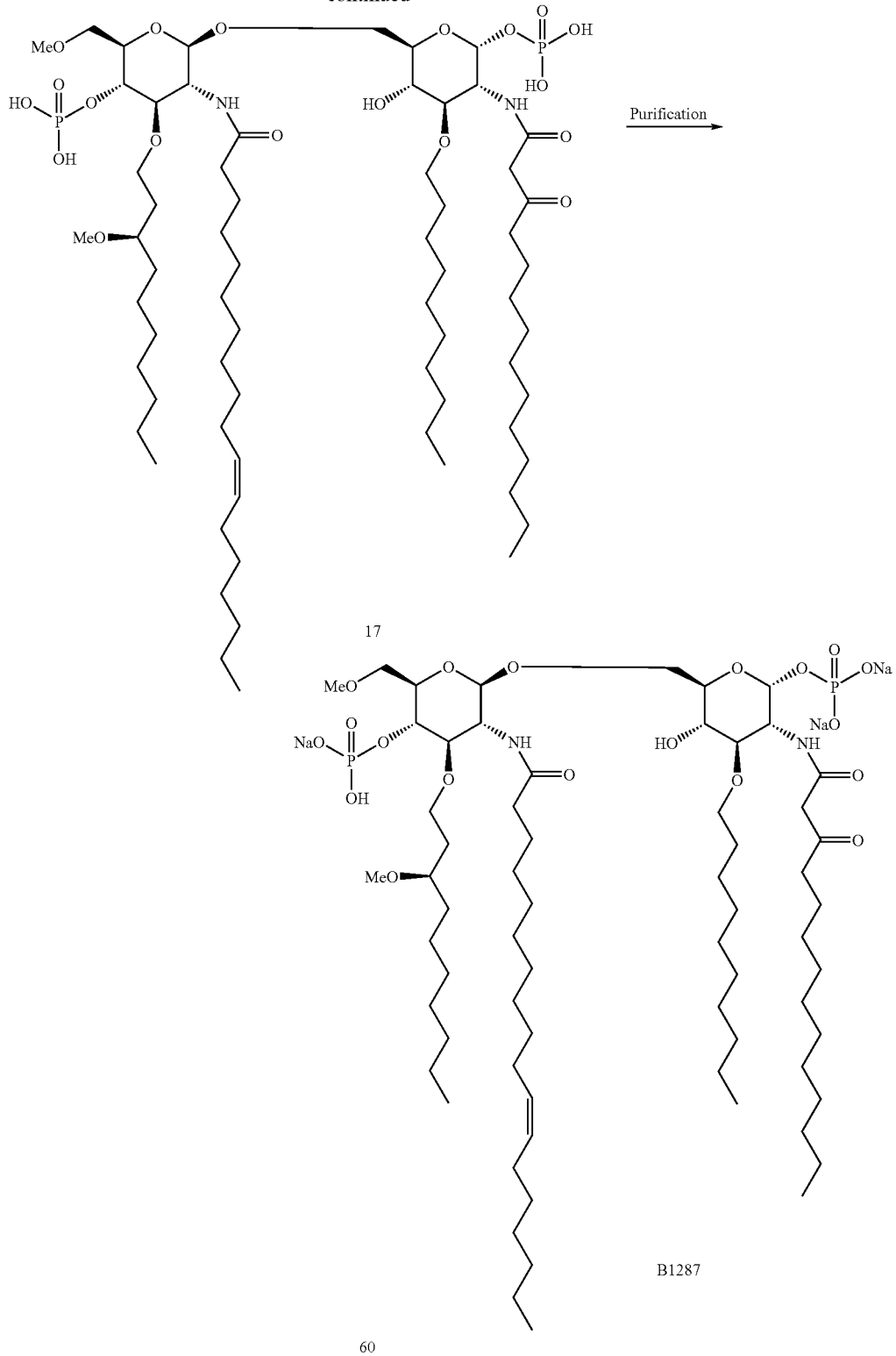

A 100 L, glass-lined, iconel reactor equipped with a mechanical stirrer and blanketed with nitrogen gas was prepared for use by flushing the reactor through pumping process water into the bottom drain valve while exiting through the top of the valve tree. The flushing process was maintained for five minutes, after which time the flush was stopped and the water present in the reactor was checked for impurities. The water was drained. Methanol was pumped through the reactor in a similar fashion as that described above for the water flushing process. The wash methanol was drained to waste. THF was pumped through the reactor in a similar fashion as that described above for the water flushing process. The wash THF was drained to waste. The reactor was then charged approximately half full with fresh THF. The THF was refluxed through the condenser system for 30 minutes, after which time the THF was drained to waste. The reactor was then placed under a vacuum of <50 Torr for 40 minutes. The reactor when then flushed with nitrogen gas.

A solution of compound 16 in low-water THF was prepared by mixing 8.80 kg of THF with 13.90 kg of product iol from the previous reaction. Solid triphenylphosphine (2.22 kg, 8.46 mol) was added to a 100 L glass-lined reactor. Tetrakis(triphenylphosphine)palladium (3.22 kg, 2.79 mol) was transferred into the reactor by use of a nitrogen-purged glove bag affixed to the port of the reactor. The reactor was then charged with 13.30 kg of low-water THF, and the mechanical stirrer was stated. After stirring for one hour, 15.21 kg of double-distilled acetic acid was added. The addition of the solution of compound 16 in THF was then started at such a rate as to allow addition over a period of approximately one hour. Starting at 25° C., the internal reaction temperature was 33.8° C. at the end of the addition one hour later [This was accomplished by leaving the reactor jacket circulation off during the early phase of the 15/THF addition. At a time of 50 minutes into the addition, the jacket temperature was then set to 40° C. in preparation for the subsequent reaction period]. The reaction was then allowed to warm to 40-42° C. The reaction solution was sampled periodically for HPLC analysis. After 6 hours, the reaction was judged to be complete. Vacuum distillation at 10 Torr was conducted with a jacket temperature of 25-35° C. After two hours of distillation, there remained 27.03 kg of brown oil. This oil was split into seven parts by draining into seven, tared rotary evaporation bulbs for disbursement in the first stage of purification. The oil contained 18.41% (4.98 kg) of desired product 17 by weight, as determined by HPLC. It also contained 1.92% (0.52 kg) of THF and 29.40% (7.95 kg) of HOAc, both by weight, as determined by GC. An overall yield of 69% (3.79 mol) of compound 17 was obtained from compound 14 (5.47 mol). Compound 17 was further purified to give the final product B1287. In certain embodiments, the purification process includes (i) ion exchange chromatography, (ii) POROS 50 R2, methanol, and (iii) treatment with aqueous NaOH.

B1287

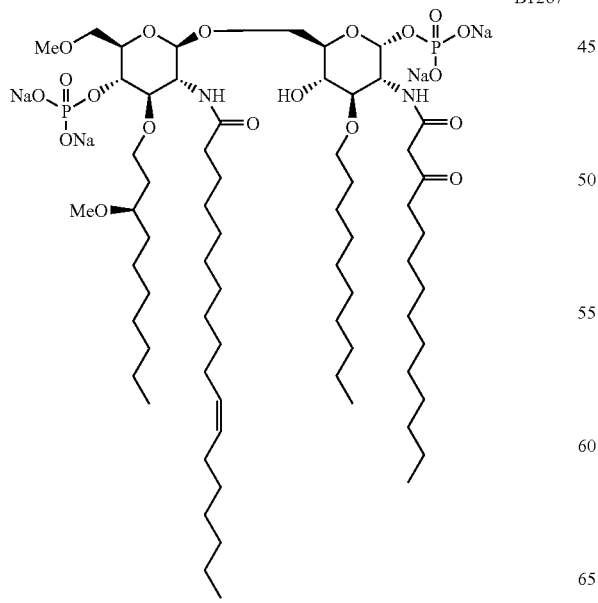

What is claimed is:

1. A compound having the structure:

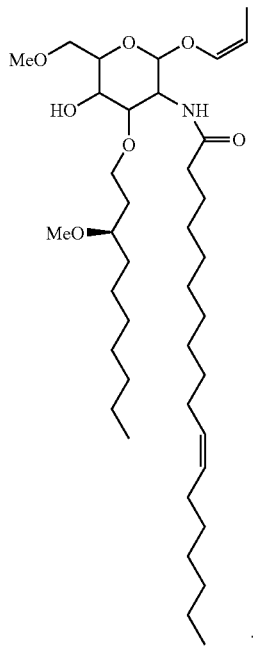

2. A compound having the structure:

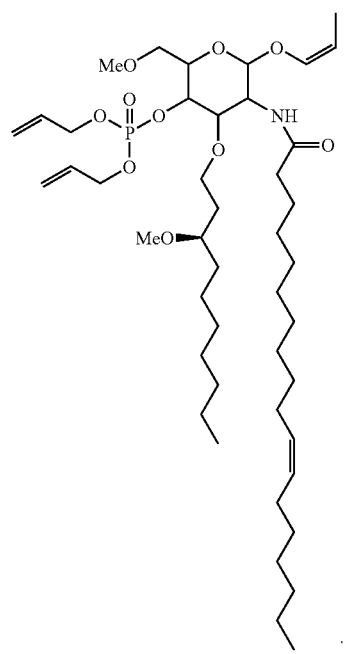

3. A compound having the structure:
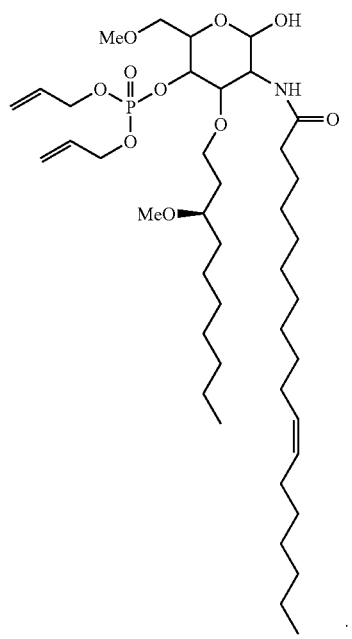
4. A compound having the structure:
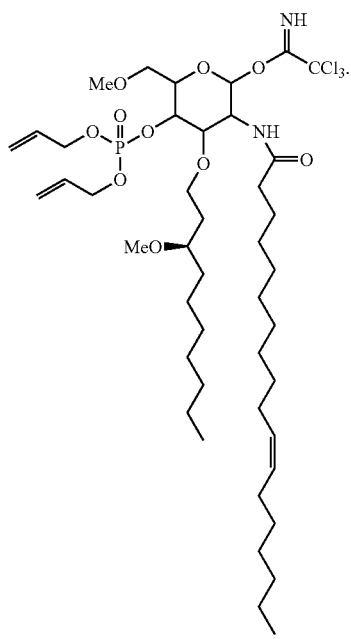
5. A compound having the structure:
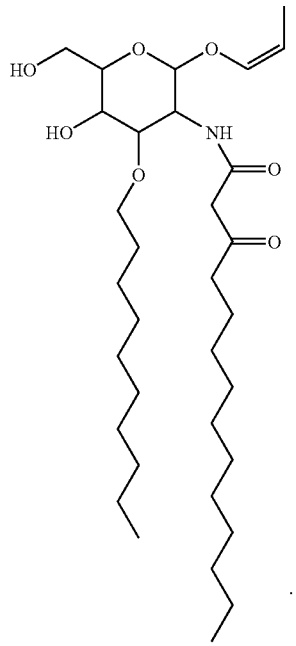
6. A compound having the structure:
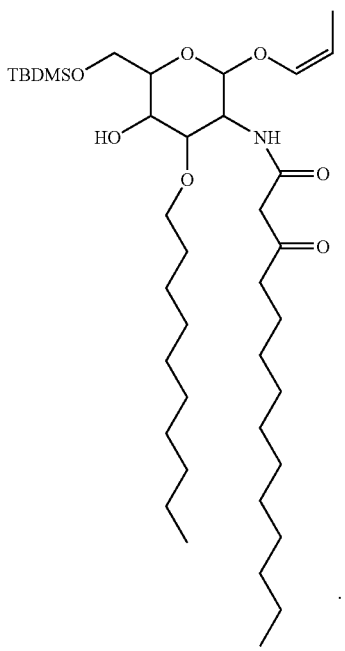

7. A compound having the structure:
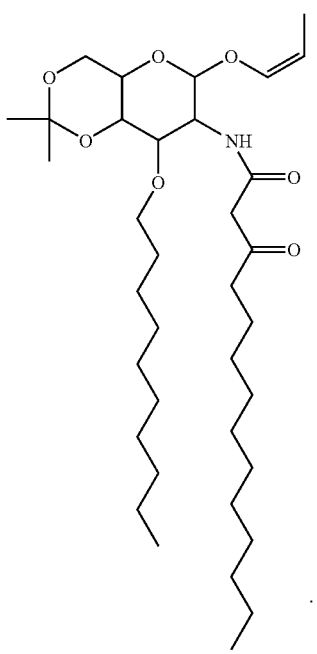
8. The compound of claim 1 having the structure:
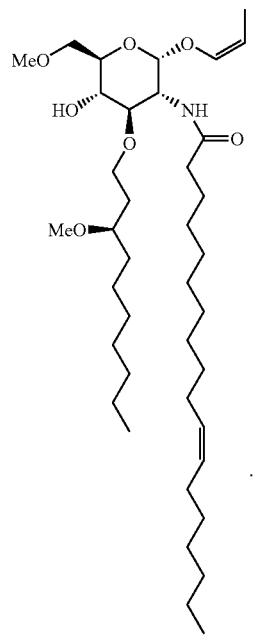
9. The compound of claim 2 having the structure:
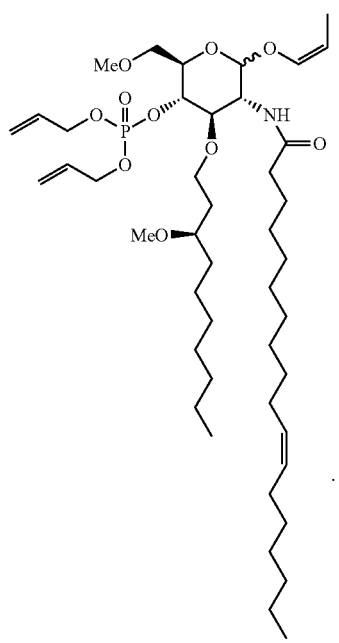
10. The compound of claim 3 having the structure:
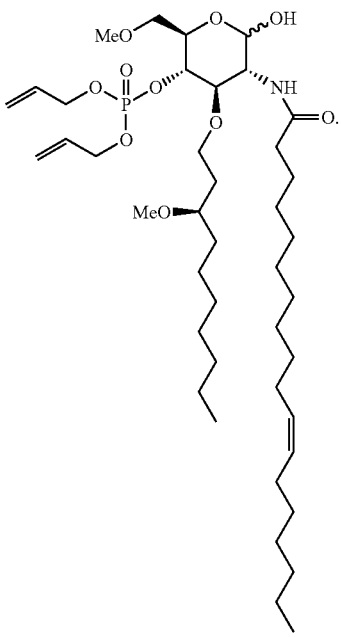

11. The compound of claim 4 having the structure:
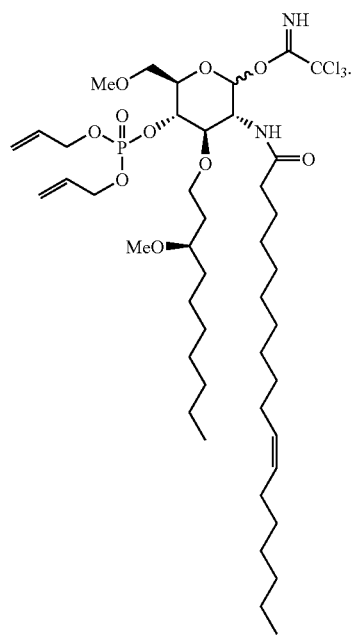
13. The compound of claim 6 having the structure:
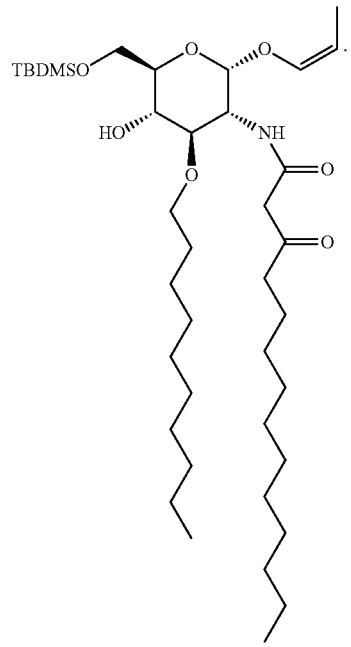
12. The compound of claim 5 having the structure:
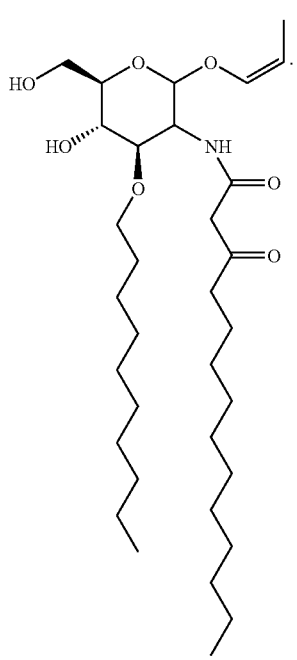
14. The compound of claim 7 having the structure:
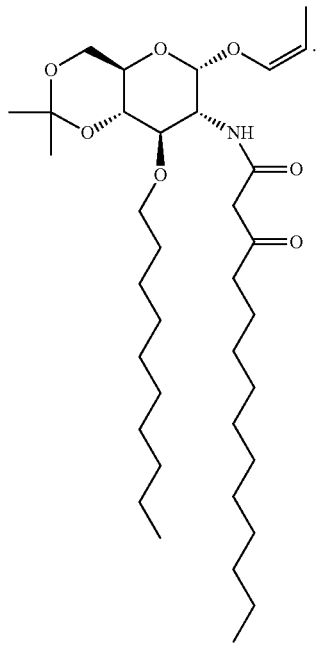
* * * * *